US007932027B2

(12) United States Patent
Fassbender et al.

(10) Patent No.: US 7,932,027 B2
(45) Date of Patent: Apr. 26, 2011

(54) METHOD FOR DETERMINING THE METHYLATION PATTERN OF A POLYNUCLEIC ACID

(75) Inventors: Anne Fassbender, Berlin (DE); Ralf Lesche, Berlin (DE); Juergen Distler, Berlin (DE); Christian Piepenbrock, Berlin (DE); Tamas Rujan, Berlin (DE); Kurt Berlin, Stahnsdorf (DE); Thomas Koenig, Berlin (DE)

(73) Assignee: Epigenomics AG, Berlin (DE)

( * ) Notice: Subject to any disclaimer, the term of this patent is extended or adjusted under 35 U.S.C. 154(b) by 787 days.

(21) Appl. No.: 11/355,417

(22) Filed: Feb. 16, 2006

(65) Prior Publication Data
US 2006/0204988 A1 Sep. 14, 2006

Related U.S. Application Data

(60) Provisional application No. 60/710,556, filed on Aug. 23, 2005, provisional application No. 60/735,349, filed on Nov. 10, 2005, provisional application No. 60/771,350, filed on Feb. 7, 2006.

(51) Int. Cl.
*C12Q 1/68* (2006.01)
(52) U.S. Cl. ............................ 435/6; 435/91.1; 435/91.2
(58) Field of Classification Search ........................ None
See application file for complete search history.

(56) References Cited

U.S. PATENT DOCUMENTS

| 6,124,120 | A | 9/2000 | Lizardi | |
|---|---|---|---|---|
| 6,605,432 | B1 | 8/2003 | Huang | |
| 7,153,671 | B2 * | 12/2006 | Berlin | ............... 435/91.2 |
| 2004/0203032 | A1 | 10/2004 | Lander | |
| 2005/0032095 | A1 | 2/2005 | Wigler | |
| 2005/0032102 | A1 | 2/2005 | Shigeta | |

FOREIGN PATENT DOCUMENTS

| DE | 10013847 | 9/2001 |
|---|---|---|
| DE | 10019173 | 10/2001 |
| DE | 10019058 | 12/2001 |
| DE | 10032529 | 2/2002 |
| DE | 10037769 | 2/2002 |
| DE | 10043826 | 3/2002 |
| DE | 10054972 | 6/2002 |
| DE | 10054974 | 6/2002 |
| DE | 10061338 | 6/2002 |
| DE | 10164501 | 6/2003 |
| DE | 10161625 | 7/2003 |
| DE | 20121966 | 11/2003 |
| DE | 20121961 | 12/2003 |
| DE | 20121963 | 12/2003 |
| DE | 20121965 | 12/2003 |
| DE | 20121967 | 12/2003 |
| DE | 20121968 | 12/2003 |
| WO | WO 00/26401 | 5/2000 |
| WO | WO 02/018632 | 3/2002 |
| WO | WO 02/077272 | 10/2002 |
| WO | WO 02/086163 | 10/2002 |
| WO | WO 03/014388 | 2/2003 |
| WO | WO 03/044226 | 5/2003 |
| WO | WO 03/052135 | 6/2003 |
| WO | WO 03/072812 | 9/2003 |
| WO | WO 03/087774 | 10/2003 |
| WO | WO 2004/035803 | 4/2004 |
| WO | WO 2004/113564 | 12/2004 |
| WO | WO 2005/001141 | 1/2005 |

OTHER PUBLICATIONS

Kaneda et al., Methylation-sensitive representational difference analysis and its application to cancer Research, Annals of the New York Academy of Sciences 983:131-141, 2003.
De Montera et al., Genetic identity of clones and methods to explore DNA, Cloning and Stem Cells 6(2):133-139, 2004.
Frigola et al., Methylome profiling of cancer cells by amplification of inter-methylated sites (AIMS), Nucl. Acids Res. 30(7):e28, 2002.
Toyota et al., Identification of differentially methylated sequences in colorectal cancer by methylated CpG island amplification, Cancer Res. 59(10) 2307-2312, 1999.
Yan et al., Dissecting complex epigenetic alterations in breast cancer using CpG island microarrays, Cancer Res. 61(23):8375-8380, 2001.
Bishop et al., A model for restriction fragment length distributions, Am. J. Human Genetics, University of Chicago Press, 35(5):795-815, 1983.
Wijsman, Optimizing selection of restriction enzymes in the search for DNA variants, Nucl. Acids Res. 12(23):9209-9226, 1984.
Yan et al., Applications of CpG island microarrays for high-throughput analysis of DNA methylation, J. Nutrition 132(8) Suppl: 2430S-2434S, 2002.
Lucito et al., Genetic analysis using genomic representations, Proc. Natl. Acad. Sci. 95(8):4487-4492, 1998.
Smith, Ligation-mediated PCR of restriction fragments from large DNA molecules, PCR Methods and Applications 2(1):21-27, 1992.
U.S. Appl. No. 60/118,760, filed Feb. 5, 1999, Huang.
U.S. Appl. No. 60/710,556, filed Aug. 23, 2005, Fassbender et al.
U.S. Appl. No. 60/735,349, filed Nov. 10, 2005, Fassbender et al.
U.S. Appl. No. 60/771,350, filed Feb. 7, 2006, Konig et al.

(Continued)

*Primary Examiner* — Heather Calamita
(74) *Attorney, Agent, or Firm* — DLA Piper LLP (US)

(57) ABSTRACT

Particular aspects relate to a method for determining the methylation pattern of a polynucleic acid, comprising: a) preparing a solution comprising a mixture of fragments of the polynucleic acid; b) coupling the fragments with a substance being detectable with a detection method; c) contacting a solution comprising the fragments of b) with a DNA microarray having a plurality of different immobilized oligonucleotides, each comprising at least one methylation site, at respectively assigned different locations thereon, the contacting under conditions affording hybridization of fragments with correlated immobilized oligonucleotides under defined stringency, and wherein the immobilized oligonucleotides have a length of less than 200 bases; d) optionally performing a a washing step; and e) detecting, using the physical detection method, such immobilized nucleic acids to which solution fragments are hybridized and/or to which solution fragments are not hybridized.

21 Claims, 13 Drawing Sheets

OTHER PUBLICATIONS

Bolstad et al., "A comparison of normalization methods for high density oligonucleotide array data based on variance and bias," Bioinformatics, 2003, pp. 185-193, vol. 19, No. 2.

Cheung et al., "Whole genome amplification using a degenerate oligonucleotide primer allows hundreds of genotypes to be performed on less than one nanogram of genomic DNA," Proceedings of the National Academy of Sciences, Dec. 1996, pp. 14676-14679, vol. 93.

Cross et al., "Purification of CpG islands using a methylated DNA bindign column," Nature Genetics, Mar. 1994, pp. 236-244, vol. 6.

Dean et al., "Comprehensive human genome amplification using multiple displacement amplification," Proceedings of the National Academy of Sciences, Apr. 16, 2002, pp. 5261-5266, vol. 99, No. 8.

Eads et al., "MethyLight: A high-throughput assay to measure DNA methylation," Nucleic Acids Research, 2000, pp. e32 (i-viii), vol. 28, No. 8.

Fisher et al., "Characterization of cytosine methylated regions and 5-cytosine DNA methyltransferase (Ehmeth) in the protozoan parasite *Entamoeba histolytica*," Nucleic Acids Research, 2004, pp. 287-297, vol. 32, No. 1.

Frank-Kamenetskii, "Triplexes and Biotechnology," Chapter 21 of *Triple Helix Forming Oligonucleotides*, editors: Malvy et al., Kluwer Academic Publishers, 1999.

Gardiner-Garden et al., "CpG Islands in Vertebrate Genomes," Journal of Molecular Biology, 1987, pp. 261-282, vol. 196.

Gitan et al., "Methylation-Specific Oligonucleotide Microarray: A New Potential for High-Throughput Methylation Analysis," Genome Research, 2001, pp. 158-164, vol. 12.

Gonzalgo et al., "Identification and Characterization of Differentially Methylated Regions of Genomic DNA by Methylation- sensitive Arbitrarily Primed PCR," Cancer Research, Feb. 15, 1997, pp. 594-599, vol. 57.

Gretch et al., "The Use of Biotinylated Monoclonal Antibodies and Streptavidin Affinity Chromatography to Isolate Herpesvirus Hydrophobic Proteins or Clycoproteins," Analytical Biochemistry, 1987, pp. 270-277, vol. 163.

Hawkins et al., "Whole genome amplification—applications and advances," Current Opinion in Biotechnology, 2002, pp. 65-67, vol. 13, No. 1.

Heisler et al., "CpG Island microarray probe sequences derived from a physical library are representative of CpG Islands annotated on the human genome," Nucleic Acids Research, 2005, pp. 2952-2961, vol. 33, No. 9.

Hendrich et al., "The methyl-CpG binding domain and the evolving role of DNA methylation in animals," Trends in Genetics, 2003, pp. 269-277, vol. 19, No. 5.

Huang et al., "Methylation profiling of CpG islands in human breast cancer cells," Human Molecular Genetics, 1999, pp. 459-470, vol. 8, No. 3.

Janknecht et al., "Rapid and efficient purification of native histidine-tagged protein expressed by recombinant *vaccinia* virus," The Proceedings of the National Academy of Sciences, Oct. 1991, pp. 8972-8976, vol. 88.

Jørgensen et al., "Mbd1 is Recruited to both Methylated and Nonmethylated CpGs via Distinct DNA Binding Domains," Molecular and Cellular Biology, Apr. 2004, pp. 3387-3395, vol. 24, No. 8.

Kapranov et al., "Large-Scale Transcriptional Activity in Chromosomes 21 and 22," Science, May 3, 2002, pp. 916-919, vol. 296.

Lewin et al., "Quantitative DNA methylation analysis based on four-dye trace data from direct sequencing of PCR amplificates," Bioinformatics, 2004, pp. 3005-3012, vol. 20, No. 17.

Lippman et al., "Profiling DNA methylation pattersn using genomic tiling microarrays," Nature Methods, Mar. 2005, pp. 219-224, vol. 2, No. 3.

Lucito et al., "Detecting Gene Copy Number Fluctuations in Tumor Cells by Microarray Analysis of Genomic Representations," Genome Research, 2000, pp. 1726-1736, vol. 10.

Matarazzo et al., "In vivo analysis of DNA methylation patterns recognized by specific proteins: coupling ChIP and bisulfite analysis," BioTechniques, 2004, pp. 666-673, vol. 37, No. 4.

Rakyan et al., "DNA Methylation Profiling of the Human Major Histocompatibility Complex: A Pilot Study for the Human Epigenome Project," PloS Biology, 2004, pp. 2170-2182, vol. 2, Issue 12.

Shiraishi et al., "Methyl-CpG binding domain column chromatography as a tool for the analysis of genomic DNA methylation," Analytical Biochemistry, 2004, pp. 1-10, vol. 329.

Telenius et al., "Degenerate Oligonucleotide-Primed PCR: General Amplification of Target DNA by a Single Degenerate Primer," Genomics, 1992, pp. 718-725, vol. 13.

Weber et al., "Chromosome-wide and promoter-specific analyses identify sites of differential DNA methylation in normal and transformed human cells," Nature Genetics, Aug. 2005, pp. 853-862, vol. 37, No. 8.

Wei et al., "Methylation Microarray Analysis of Late-Stage Ovarian Carcinomas Distinguishes Progression-free Survival in Patients and Identifies Candidate Epigenetic Markers," Clinical Cancer Research, Jul. 2002, pp. 2246-2252. vol. 8.

Weinmann et al., "Isolating human transcription factor targets by coupling chromatin immunoprecipitation and CpG island microarray analysis," Genes & Development, 2002, pp. 235-244, vol. 16.

Yan et al., "Dissecting Complex Epigenetic Alterations in Breast Cancer Using CpG Island Microarrays," Cancer Research, Dec. 1, 2001, pp. 8375-8380, vol. 61.

Zhang et al., "Whole genome amplification from a single cell: Implications for genetic analysis," Proceedings of the National Academy of Sciences, Jul. 1992, pp. 5847-5851, vol. 89.

* cited by examiner

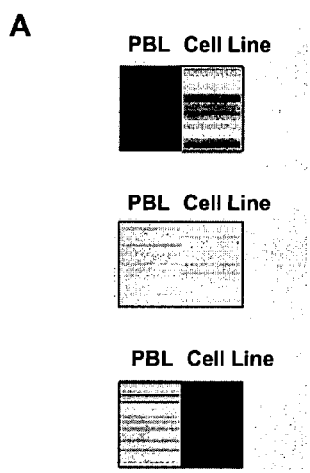 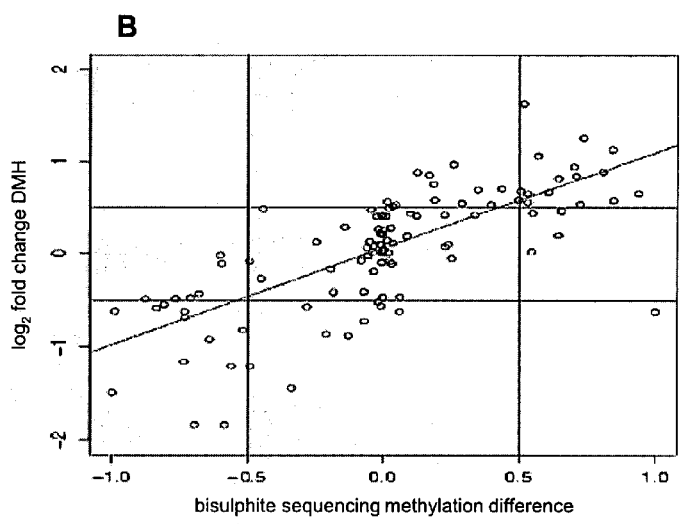
FIG. 6

SEQUENCE LISTING

<160> NUMBER OF SEQ ID NOS: 2

<210> SEQ ID NO 1
<211> LENGTH: 24
<212> TYPE: DNA
<213> ORGANISM: artificial sequence
<220> FEATURE:
<223> OTHER INFORMATION: Adapter oligonucleotide H24

<400> SEQUENCE: 1
aggcaactgt gctatccgag ggat                                          24

<210> SEQ ID NO 2
<211> LENGTH: 12
<212> TYPE: DNA
<213> ORGANISM: artificial sequence
<220> FEATURE:
<223> OTHER INFORMATION: Adapter oligonucleotide H12

<400> SEQUENCE: 2
taatccctcg ga                                                       12

METHOD FOR DETERMINING THE METHYLATION PATTERN OF A POLYNUCLEIC ACID

CROSS-REFERENCE TO RELATED APPLICATIONS

This application claims the benefit of priority to U.S. Provisional Patent Application Nos. 60/710,556, filed 23 Aug. 2005; 60/735,349, filed 10 Nov. 2005; and 60/771,350, filed 7 Feb. 2006, and additionally claims the benefit of priority to German Patent Application Nos: DE 102005007185.6, filed 16 Feb. 2005; DE 102005023055.5, filed 13 May 2005; DE 102005025240.0, filed 31 May 2005; and DE 102005036500.0, filed 28 Jul. 2005, all of which are incorporated by reference herein in their entireties.

FIELD OF THE INVENTION

Aspects of the present invention relate generally to determining the methylation pattern of a polynucleic acid.

BACKGROUND

Many diseases, in particular cancer diseases, are accompanied by modified gene expression. This may be related to a mutation of the genes themselves, which leads to an expression of modified proteins or to an inhibition or over-expression of the proteins or enzymes. A modulation of gene expression may, however, also occur by epigenetic modifications, and in particular by DNA methylation. Such epigenetic modifications do not alter the actual DNA coding sequence, but nonetheless have substantial health implications, and it is clear that knowledge about methylation processes and modifications of methylation related metabolism and DNA methylation are essential for understanding, prophylaxis, diagnosis and therapy of diseases.

The precise control of genes, which themselves represent but a small part of the complete mammalian genome, is a question of regulation in consideration of the fact that the bulk of genomic DNA in non-coding. The existence of such non-coding 'trunk' DNA containing introns, repetitive elements and potentially actively transposable elements, necessitates effective mechanisms for their durable suppression (silencing). Cytosine methylation by S-adenosylmethionine (SAM)-dependent DNA methyltransferases, which forms 5-methylcytosine, represents one such mechanism for modification of DNA-protein interactions. Genes can be transcribed by methylation-free promoters, even when adjacent transcribed or non-transcribed regions are widely methylated. This permits the use and regulation of promoters of functional genes, whereas the trunk DNA including the transposable elements is suppressed. Methylation is also involved in the long-term suppression of X-linked genes, and may lead to either a reduction or an increase of the degree of transcription, depending on where the methylation in the transcription unit occurs.

Nearly the complete natural DNA methylation in mammals is restricted to cytosine-guanosine (CpG) dinucleotide palindrome sequences, which are controlled by DNA methyl transferases. CpG dinucleotides represent about 1 to 2% of all dinucleotides and are concentrated in so-called CpG islands. A generally accepted definition of CpG islands means a DNA region of about 200 bp having a CpG content of at least 50%, and where the ratio of the number of observed CG dinucleotides and the number of the expected CG dinucleotides is larger than 0.6 (Gardiner-Garden, M., Frommer, M. (1987) J. Mol. Biol. 196, 261-282). Typically, CpG islands have at least 4 CG dinucleotides in a sequence having a length of 100 base pairs.

If CpG islands are present in promoter areas, they often have a regulatory function for the expression of the respective gene. If the CpG island is hypomethylated, expression can take place. Hypermethylation often leads to the suppression of the expression. In the normal state, a tumor suppressor gene is hypomethylated. If a hypermethylation takes place, this will lead to a suppression of the expression of the tumor suppressor gene, which is frequently observed in cancer tissues. In contrast thereto, oncogenes are hypermethylated in healthy tissue, whereas in cancer tissue they are frequently hypomethylated.

Cytosine methylation typically prevents the binding of proteins regulating transcription. This leads to a modification of associated gene expression. In the context of cancer, for example, the expression of cell division regulating genes is thereby affected (e.g., the expression of apoptosis genes is down-regulated, whereas oncogene expression is up-regulated). DNA hypermethylation also has a long-term influence on gene regulation. Via cytosine methylation, histone de-acetylation proteins can bind to the DNA by their 5-methyl cytosine-specific domain. Consequently, histones are de-acetylated, leading to a tighter DNA compaction, whereby regulatory proteins are precluded from DNA binding.

Consequently, the efficient detection of DNA methylation patterns is an important tool for developing new approaches for prevention, diagnosis and treatment of diseases and for target screening. In particular, individualized methylation profiles can be prepared, and a tailored therapy thereby deduced. Additionally, the effects of a therapy can be monitored.

There is, therefore, a pronounced need in the art for novel and efficient methods for identifying and characterizing unknown methylation patterns.

Differential Methylation Hybridization (DMH; Huang et al, *Hum Mol Genet*, 8:459-470, 1999; U.S. patent application Ser. No. 09/497,855, both incorporated by reference in their entirety) is an art-recognized method for determining methylation patterns or for determining hypermethylated CpG islands. In DMH applications, DNA fragments obtained by digestion with restriction enzymes are hybridized on a DNA microarray that carries cloned CpG islands. DNA, originating from a tissue sample, is initially cut with a single non-methylation-specific restriction enzyme (e.g., MseI). The resulting fragments are then ligated with linkers, and the linker-ligated fragment mixture is cut with methylation-specific endonucleases (e.g., BstUI and/or HpaII), and amplified by means of PCR. The resulting amplified fragment mixtures are also referred to herein as DMH 'amplificates' or 'amplicons.' After a purification step, the amplicons (amplificates) are coupled with a fluorescence dye. Typically, the preceding steps are performed on the one hand with diseased tissue DNA and on the other hand with DNA from adjacent healthy tissue of the same tissue type, and the respective fragments are labeled with different fluorescence dyes. Both fragment solutions are then co-hybridized on a DNA microarray having immobilized CpG island sequences. After washing steps, a picture of the DNA microarray is taken with a commercial scanner that is sensitive to fluorescence radiation. The picture or pattern of fluorescent dots visible therein is analyzed to determine differences in methylation between and among CpG clones (see, e.g., Wei et al, *Clinical Cancer Research*, 8:2246-2252, 2002; Yan et al, *Cancer Res*. 61:8375-80, 2001; see also WO 2003/087774 (PCT/US03/11598), and U.S. Pat. No. 6,605,432).

In DMH applications, the immobilized nucleic acids are composed of clones from so-called "CpG island libraries (CGI libraries)"; that is, from libraries of clones having typical lengths of 200-700 base pairs and being enriched for CpG islands. Typically, clones including repeat sequences are also present (see, e.g., WO 2003/087774 (PCT/US03/11598)). Unfortunately, the relatively high production expenses of the CGI clone libraries are an inherent drawback of the method.

Additionally, to a significant extent the utility of DMH is limited to general genome analysis (discovery analysis), where only a broad analysis of the the genome sequence is desired. This is because of: (i) the number of coupling positions on the microarray is limited; (ii) the presence of repeat sequences unfortunately reduces the capacity of the DNA microarray; and (iii) the limited number of coupling positions on the microarray is therefore not used in an optimum manner by different partial sequences.

Further drawbacks of DMH are that: sequences may be redundantly present in CGI clone libraries; that cross contamination of the clones leads to a mixing of the library; and the possibility of cross-hybridizations, and the large expenses for production. Sequence redundancy can be explained by the presence of partially overlapping clones, or by multiple recurrences of the same clone. Additionally, because of the length of the clones, the possibility of cross-hybridization events cannot be excluded, and with increasing length, the probability of repeats becomes higher. The large 'production expenses' are caused, among other factors, by the necessity to sequence all clones of the library.

A further problem in DMH applications is that the number of fragments to be tested is enormously complex, leading to unstable signals, increased cross-hybridization and increased occurrence of non-specific hybridization. The theoretical reason for the high complexity relates to the fact that, in the art-recognized DMH method, all fragments that are not cut by methylation-specific restriction enzymes are amplified in the last step. Because the number of fragments that simultaneously have a restriction recognition sequence and are down-methylated is very small, the complexity of the mixture is extremely high, and effectively reflects amplification of a substantial portion of the entire genome. Therefore, a specific reduction of fragment complexity would be particularly desirable here, because a very large number of different fragments leads to comparatively small amplification factors; that is, individual fragments per se are only slightly amplified, and the difference in the copy-number between methylated and unmethylated fragments is small. Even if the amplification factor could be increased, detection of individual fragments from a very large population of different fragments would not be possible or would be substantially problematic, because of cross hybridization effects. With regard to such excessive complexity, reference is made to the document Lucito, et al., *Genetic Research* (2000).

There is, therefore, a pronounced need in the art for more simplified methods to effectively reduce the complexity of the obtained DNA fragment solutions obtained in DMH applications, and preferably where such methods simultaneously afford obtaining potentially interesting fragments.

A method referred to as "MSO," has also been described by Gitan, et al (Gitan R. S., Shi H., Yan P. S., Huang T. H-M., Methylation-specific oligonucleotide microarray: A new potential for high-throughput methylation analysis. *Genome Res.*, 12:158-164, 2001). The Gitan implementation describes the investigation of methylation sites within a defined region, such as a specific CpG island.

The drawbacks of methods based on analysis of bisulfite-transformed DNA are the additional expenses for the method, and the relatively high loss of DNA that occurs during the bisulfite treatment. Further, the design of the requisite oligos becomes more difficult, because the complexity of the investigated nucleic acids became less by the substantial elimination of the cytosines (by conversion of the unmethylated cytosines into thymines).

Furthermore, the detection of SNPs (single nucleotide polymorphisms) is considerably more difficult and sensitive for/vulnerable to cross hybridizations.

In other contexts, microarrays carrying oligonucleotides are in principle known, and these oligonucleotides can be synthesized on the substrate of the microarray, which makes this kind of detection generally advantageous for high-throughput methods.

SUMMARY OF ASPECTS OF THE INVENTION

Particular aspects provide an efficient method for identifying unknown methylation patterns that is more effective and powerful than prior art methods Additional aspects provide simplified methods to more effectively reduce the complexity of the DNA fragment solutions obtained in DMH applications, while simultaneously providing for obtaining potentially interesting fragments.

Particular aspects provide a method for detecting methylation differences, which on the one hand permits the use of genomic DNA and need not be based on a previous transformation such as the bisulfite treatment, and on the other hand simultaneously affords investigation of as many different CpG positions (CG dinucleotides) as possible, where the employed DNA microarray is optimized with regard to the complexity for a comprehensive methylation analysis, and is adapted to the steps distinguishing the methylation patterns.

In particular aspects, the inventive methods reduce the complexity of the fragment mixture in the DMH method and thus lead to a significantly increased efficiency of the DMH method. This reduction of complexity may be achieved in different ways: on the one hand by using at least one methylation-specific restriction enzyme without previous addition of a non-methylation-specific restriction enzyme and subsequent amplification of fragments of a certain size range; and on the other hand by using at least two non-methylation-specific restriction enzymes in a first step, and after an amplification step by using at least one methylation-specific restriction enzyme in a second digestion step.

Further, oligoarrays may be used for the method according to the invention, in lieu of the known CpG island arrays. This leads to additional advantages:

i) by an "in silico" definition of the oligonucleotides, regions of the genome with repeats can be excluded, and thereby at last the capacity of the microarray can be optimized;

ii) by using oligonucleotides on the microarray, the microarray can be prepared at little cost, namely by direct synthesis on the chip surface;

iii) by using oligonucleotides on the microarray, a higher flexibility of the design and higher densities are achieved;

iv) by using oligonucleotides on the array, methylation differences can still be detected in regions that have a CG density of only 2% (conventional DMH methods typically detect CpG islands, which have a CG density of at least 4%;

v) by using oligonucleotides on the array, it is possible to examine a substantially larger number of potentially interesting methylation sites, than this was possible with a CGI clone array, and thereby the whole genome can be tested for different methylation in a single hybridization step with a corresponding array;

vi) because the sequence of the oligonucleotides is known, and they are specifically synthesized, sequencing as in the case of the clones of a conventional array is not necessary;

vii) because the sequence of the oligonucleotides is known, and they are specifically synthesized, a redundancy (as in conventional arrays) of the chips can be prevented; and viii) by using oligonucleotides that are only up to 80 bp long, cross hybridization events (a problem with conventional array) are effectively excluded.

Oligoarrays may also be used in a combination with other non-DMH methods for producing fragments. In particular, it is possible to specifically enrich methylated or unmethylated fragments, and to then analyze them by means of oligonucleotide arrays. The use of oligonucleotide arrays in discovery applications leads to many advantages compared to the prior art. A method for determining methylation patterns, which uses immobilized oligonucleotides in lieu of immobilized clones has been previously described. However, amplification of the nucleic acids before hybridization thereof with these oligo arrays is a requirement of such methods. Therefore, such oligos, typically used in pairs, are only suitable to detect methylation in converted/treated/transformed nucleic acids (e.g., subjected to bisulfite treatment). In such applications, the epigenetic difference (is there a methyl group at the cytosine or not) becomes obvious only after the treatment, such that it will be maintained and thus detectable as a sequence difference (thymines or cytosines) after an amplification (e.g., by PCR). The methylation degree in the tested and amplified sample can then be determined by using CG-specific and TG-specific oligos. This technology is, for example, described in more detail in WO 01/38565 (U.S. Ser. No. 10/148,140) and WO 02/18632 (U.S. Ser. No. 10/363,345).

Particular aspects provide a method for determining the methylation pattern of a polynucleic acid, comprising:

a) obtaining a solution comprising a nucleic acid, and obtaining therefrom a solution comprising a mixture of fragments of the polynucleic acid, wherein the composition of the fragment mixture depends on the methylation pattern of the polynucleic acid;

b) the fragments of step a) are optionally amplified and coupled with a substance being detectable with an optionally physical detection method, wherein optionally an amplification of the fragments may occur;

c) a solution comprising the fragments of step b) is contacted with a DNA microarray having a plurality of different immobilized nucleic acids, in particular oligonucleotides, under conditions where hybridization of fragments occurs with correlated immobilized nucleic acids under a defined stringency, wherein the immobilized nucleic acids are selected from nucleic acids, which are specific for fragments of a genome, preferably the human genome, and are localized on the DNA microarray at different respectively assigned positions on the DNA microarray;

e) optionally, a washing step is performed;

d) such immobilized nucleic acids, to which fragments of the solution are hybridized and/or to which fragments of the solution are not hybridized, are detected using the detection method, f) optionally, from the detected hybridizations and/or detected non-hybridizations according to step e) the methylation pattern of the polynucleic acid being the educt of step a) is derived.

Further, aspects relate to: a test kit for performing one of the above methods; a method for preparing such a DNA microarray suitable for determining the methylation pattern of a polynucleic acid; the use of such a method for determining the methylation pattern of a polynucleic acid for identifying an indication-specific marker or a target or a modulator for such a target, the use of such a modulator for preparing a pharmaceutical composition having the specific indication, and the use of such a method or test kit for diagnosing and/or prognosticating a disease.

BRIEF DESCRIPTION OF THE DRAWINGS

FIG. 1 shows the results substantially according to the prior art, using a non-methyltion-specific restriction enzyme (MseI) and two methylation-specific restriction enzymes (BstU1, HapII).

FIG. 2 shows the results of the method according to the invention, i.e. using several non-methylation-specific restriction enzymes, namely MseI, Bfa1 and Csp6, and several methylation-specific restriction enzymes, namely BstU1, HapII, HpyCH4IV and HinP1.

FIG. 3 illustrates the differences of the working procedures (workflow) of the preparation of a mixture of methylated fragments of a sample containing DNA.

FIG. 6 shows validation of the technology by direct bisulfite sequencing. Validation of marker candidates found by an optimized DMH workflow and an array hybridization. A) Examples of direct bisulfite sequencing results generated by analysis by the proprietary ESME software (Joern, L. et al;

2004). Yellow and blue indicate unmethylated and methylated CpG's, respectively. B) Correlation of methylation state of the 111 analyzed fragments determined by bisulfite sequencing with log ratio as determined by DMH.

Figure 7:
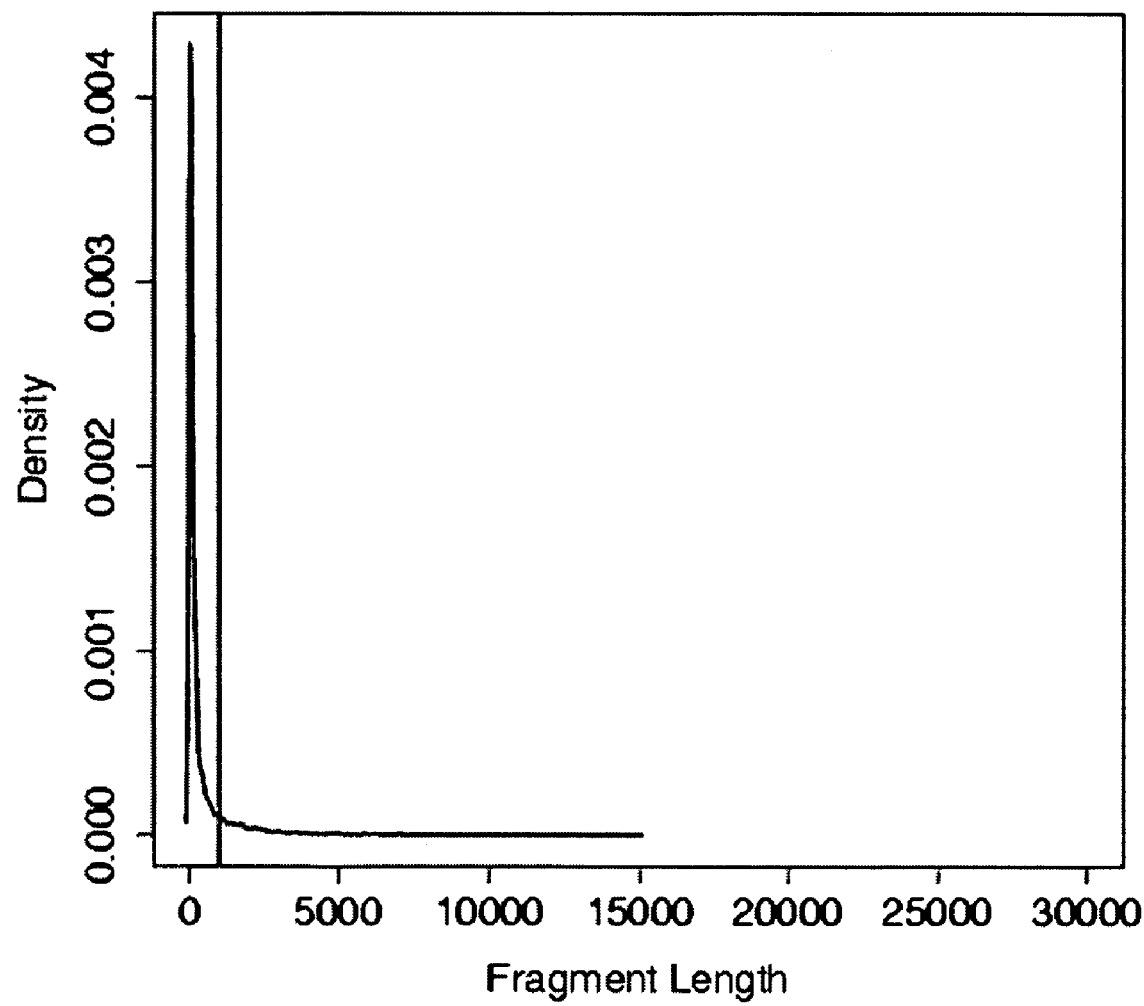
Figure 8:
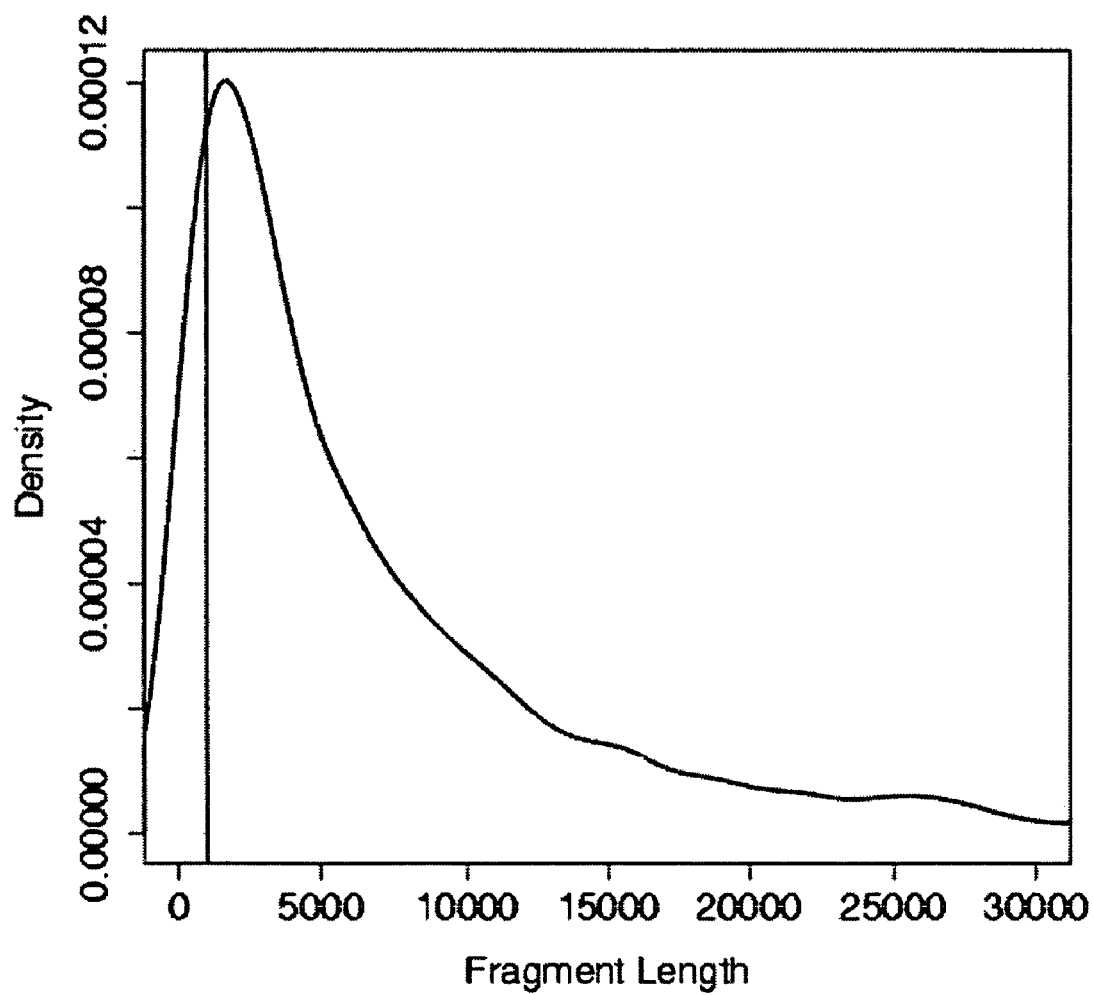

FIG. 7 shows fragment length distribution after "in silico" digestion with BstU for DNA sections with a share of CpG islands of more than 0.3. FIG. 8 shows a fragment/length histogram after "in silico" digestion with BstU for DNA sections with a share of CpG islands of at most 0.3.

Figure 9:
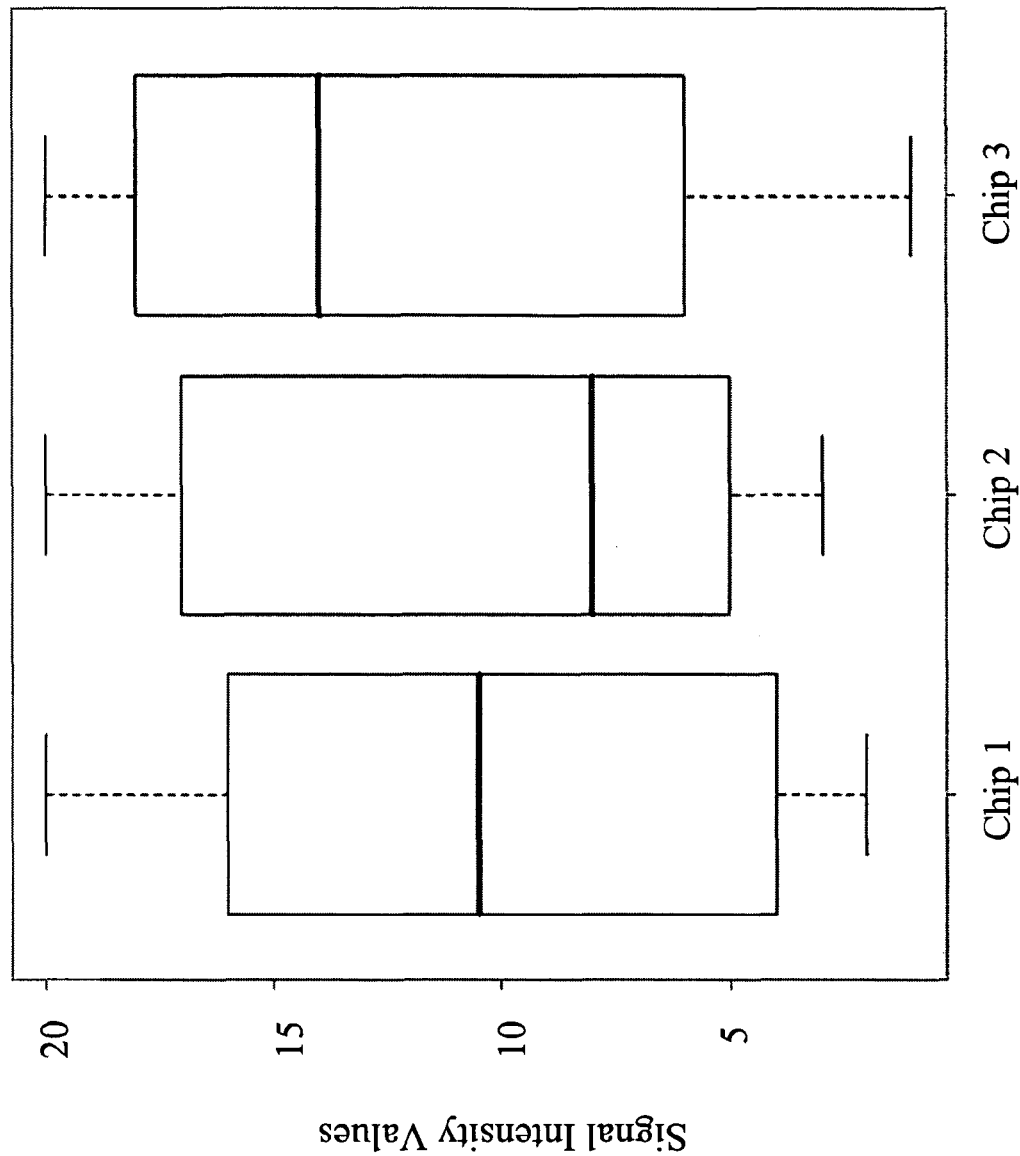

FIG. 9 shows boxplots of signal intensity values as presented in Table 3 (y-axis) for three microarray-chips (x-axis, chips 1, 2, 3).

Figure 10:
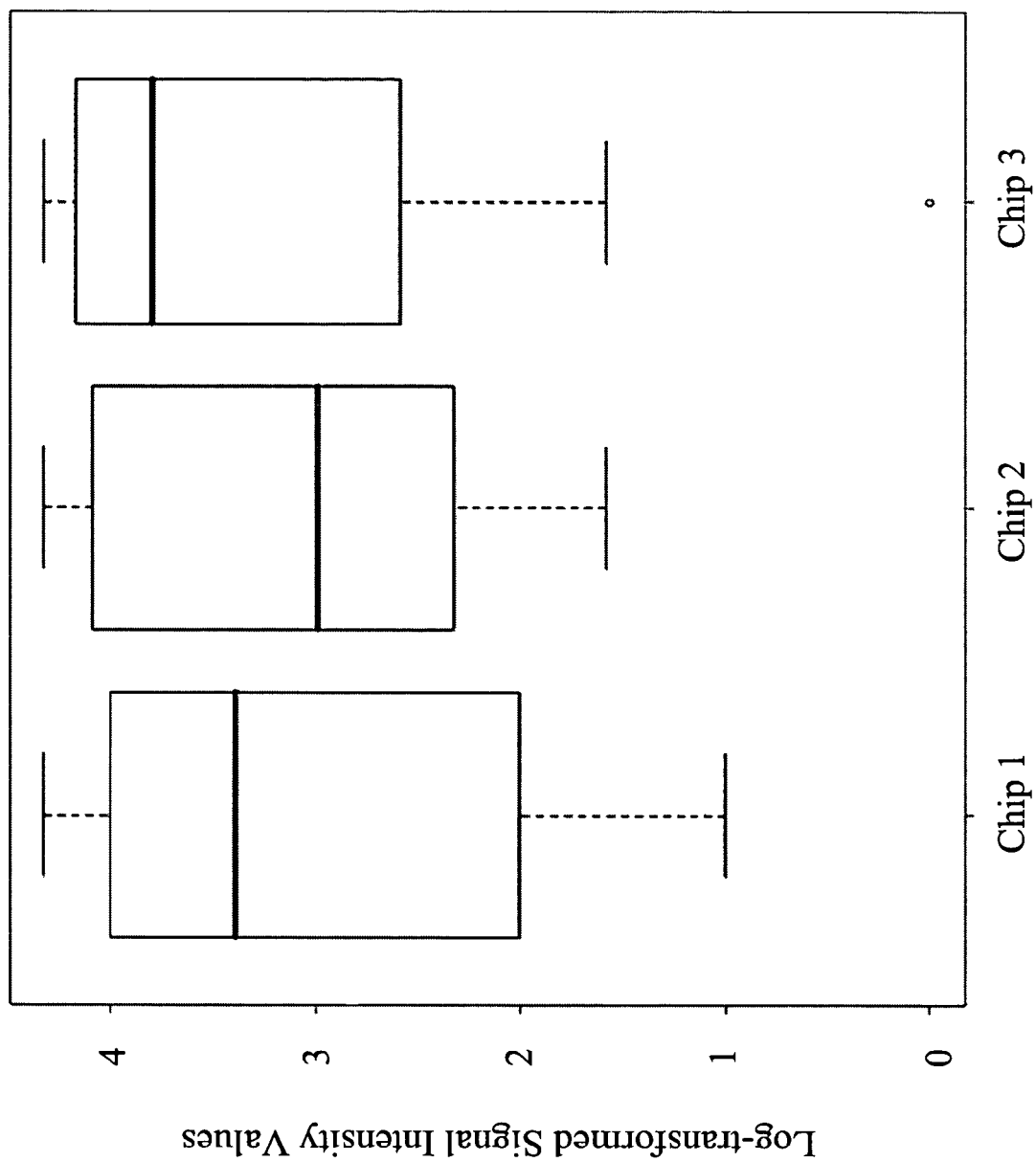

FIG. 10 shows boxplots of signal intensity values as presented in Table 4 (y-axis) after "log$_2$ transformation" for the same three microarray-chips as FIG. 9 (x-axis, chips 1, 2, 3).

Figure 11:
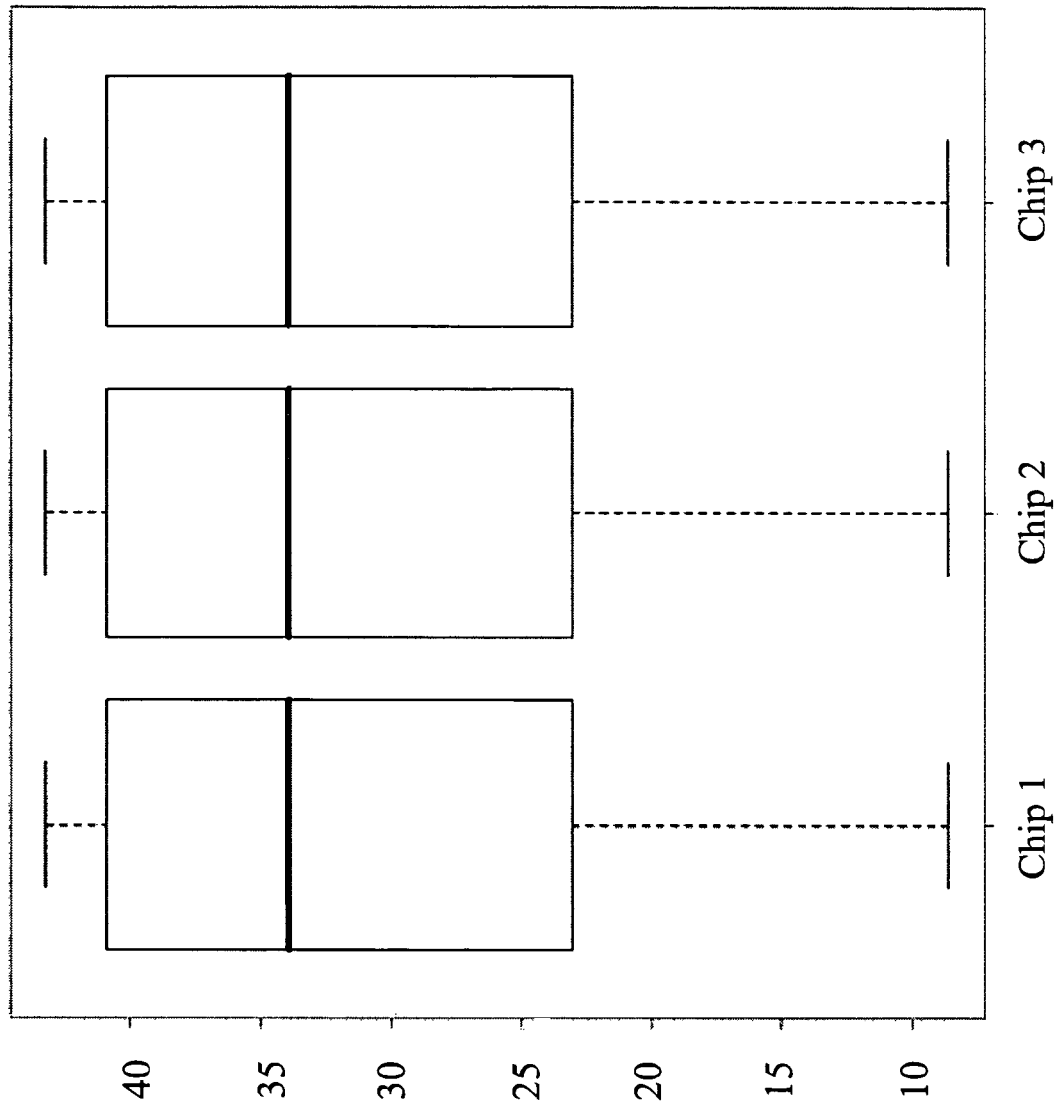

FIG. 11 shows boxplots of signal intensity values as presented in Table 8 (y-axis) after "log$_2$ transformation" and "Quantile Normalization" for the same three microarray-chips as FIG. 9 (x-axis, chips 1, 2, 3).

Figure 12:
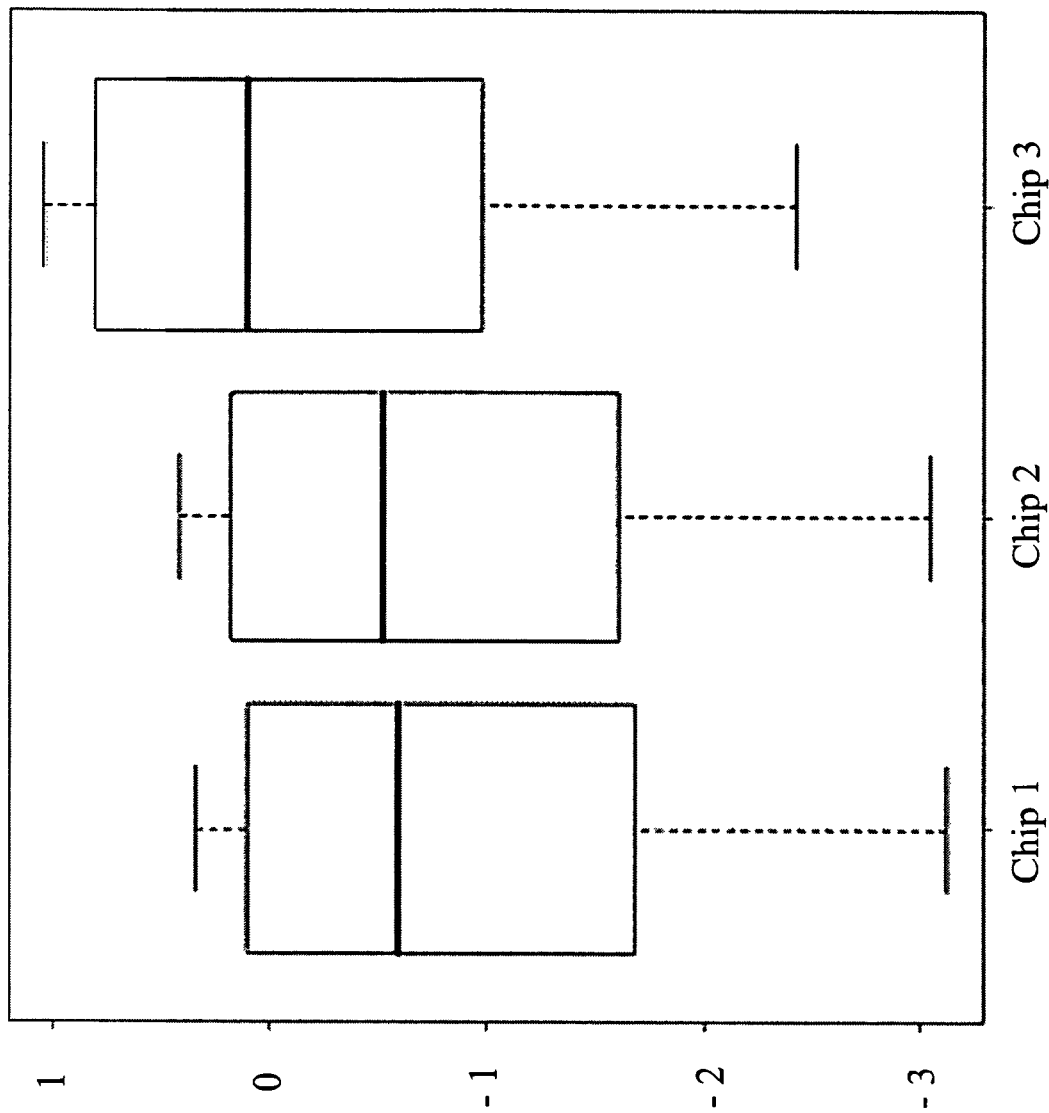

FIG. 12 shows boxplots of signal intensity values as presented in Table 9 after "log$_2$ transformation", "Quantile Normalization" and "Baseline shift" for the same three microarray-chips as FIG. 9 (x-axis, chips 1, 2, 3).

Figure 13:
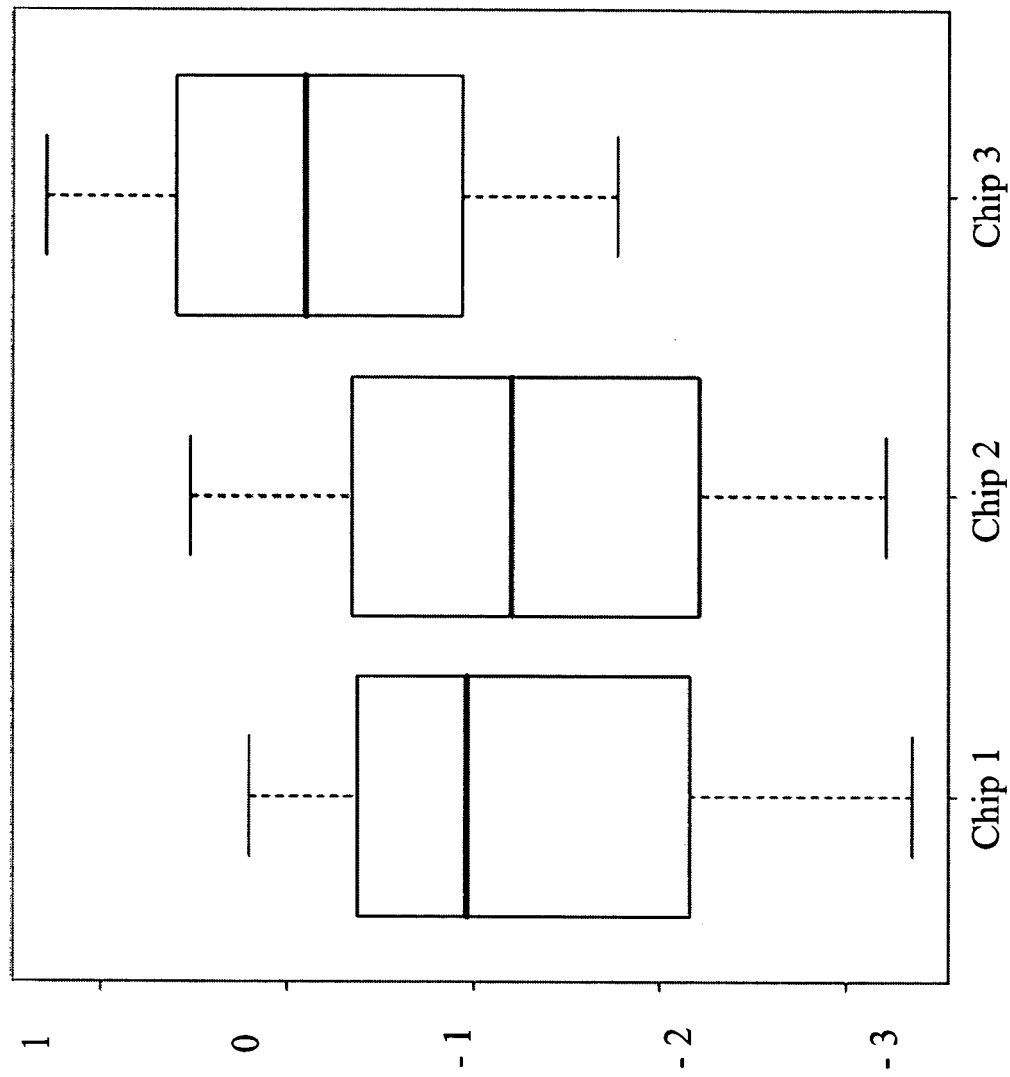

FIG. 13 shows boxplots of signal intensity values as presented in Table 10 after "log$_2$ transformation", "Quantile Normalization", "Baseline shift" and generation of representative values by selecting a median value for the same three microarray-chips as FIG. 9 (x-axis, chips 1, 2, 3).

DETAILED DESCRIPTION

For achieving various technical objects, particular aspects of the invention teach and provide a method for determining the methylation pattern of a polynucleic acid with the following steps:

a) a solution comprising a mixture of fragments of the polynucleic acid is made from a solution comprising the polynucleic acid, e.g. a solution comprising genomic DNA, wherein the composition of the fragment mixture depends on the methylation pattern of the polynucleic acid, b) the fragments of step a) are coupled with a substance being detectable with an optionally physical detection method, wherein optionally an amplification of the fragments may occur, c) a solution comprising the fragments of step b) is contacted with a DNA microarray, which carries a plurality of different immobilized nucleic acids, in particular oligonucleotides, under conditions, at which a hybridization of fragments occurs with correlated immobilized nucleic acids under defined stringency, wherein the immobilized nucleic acids are selected from nucleic acids, which are specific for fragments of a genome, preferably the human genome, and are localized on the DNA microarray at different respectively assigned positions, d) optionally, a washing step is performed;

e) such nucleic acids, to which fragments of the solution are hybridized and/or to which fragments of the solution are not hybridized, are detected using the detection method;

f) optionally, from the detected hybridizations and/or non-hybridizations according to step e) the methylation pattern of the polynucleic acid being the educt of step a) is derived.

Significantly, the method according to the invention may be performed in particular without a bisulfite treatment in step a) or before step a).

I. First Preferred Embodiment

Complexity Reduction by Using Methylation-Specific Restriction Enzymes

A first particularly preferred embodiment of a method according to the invention for achieving the technical object provides a method for making a mixture of fragments of a polynucleic acid, comprising:

a) a solution comprising a polynucleic acid is prepared;

b) optionally, a processing step is performed, in which substances that are not polynucleic acids, are depleted, or the polynucleic acid is enriched;

c) a methylation-specific restriction enzyme is added to the solution in the absence of prior addition of (e.g., digestion with) a non-methylation-specific restriction enzyme, wherein the polynucleic acid is cut to fragments at cutting sites, which are capable of being methylated, but are not methylated; and d) the fragments obtained in step c) are subjected to an amplification step after adapter ligation, and fragments having a length in the range from 50 bases to 5,000 bases are selectively enriched.

In an alternate embodiment of the invention, fragments after adapterligation are subject to a digestion with the same restriction enzyme or enzymes as used in c) before amplification. This has the advantage that religated fragments are digested while fragment-adapter ligations remain unaffected.

Therefore, in particular aspects, a solution with a mixture of fragments of a polynucleic acid is obtained, which is for instance suitable for DMH analysis. By not using a non-methylation-specific restriction enzyme in connection with selective amplification of the specified length window, a reduction of complexity of the mixture by a factor greater than 100 is achievable; that is, by a factor 100 better than in prior art DMH applications/implementations. This is also based on the fact that methylated sequence regions and sequence regions without cgcg elements (recognition sites for methylation sites) are not cut, and consequently form fragments, the length of which is usually above the upper limits of the amplification window. By contrast, regions with recognition sites, as far as not methylated, are cut and form fragments with a length below the upper limit of the amplification window. Further, no potentially interesting fragments are cut non-methylation-specifically, and thus reduced to a length below the lower limit of the window. Consequently, all interesting fragments (i.e., those with potentially hypermethylated or hypomethylated sites) are available for subsequent analyses. Finally, the overall process is simplified, because different restriction enzymes are used at a lesser degree. It is, for example, possible to perform all reactions up to the hybridization on a DMH chip in one vessel (one tube process). Consequently, processing is simplified and considerably faster. Finally, the number of potential error sources in the process is substantially reduced.

It is, therefore, particularly preferred that there is not used a non-methylation-specific restriction enzyme in any of the steps.

In principle, every methylation-specific restriction enzyme can be used for the purpose of the invention. Preferably the methylation-specific restriction enzyme is selected from the group consisting of BisI, BstUI, BshI236I, AccII, BstFNI, McrBC, GlaI, MvnI, HpaII (HapII), HhaI, AciI, SmaI, HinP1I, HpyCH4IV, and mixtures of two or more of said enzymes.

In particular aspects, the polynucleic acid used is a naturally occurring DNA. Preferably, genomic DNA is used (e.g, human genomic DNA).

Preferably, in d), fragments with a length of 80 to 5,000 bases, preferably 100 to 2,000 bases, and most preferably 100 to 1,000 bases, are selectively enriched, and optimal complexity reduction is achieved, while simultaneously preserving and/or enriching the presence of potentially interesting fragments.

A further complexity reduction can be achieved, if the fragments are purified by physical methods (e.g., by gel electrophoresis, size exclusion chromatography, filtration, etc.) before or after the amplification.

The invention further relates to a method for determining the methylation pattern of a polynucleic acid, in particular that of a genomic DNA from a tissue sample of a patient, the method comprising:
  a) a process according to one embodiment of the invention is performed;
  b) thereafter the selectively amplified fragments are coupled with a substance being detectable in a physical detection method;
  c) a solution comprising the fragments of step b) is contacted with a DNA microarray having a plurality of different immobilized nucleic acids with at least one methylation site each at different, respectively assigned locations on the microarray, wherein a hybridization of fragments with correlated immobilized nucleic acids takes place with defined stringency;
  d) optionally, a washing step is performed; and
  e) such nucleic acids, to which fragments of the solution are hybridized, are detected using the physical detection method.

The detectable substance may, for example, be a fluorescence dye, wherein the detection method comprises selective scanning for the fluorescence radiation transmitted by the fluorescence dye (one-dimensional or two-dimensional, depending on the arrangement of the different immobilized nucleic acids on the chip). The fluorescence dye may be, for example, Cy3 and/or Cy5. As recognized by those of ordinary skill in the relevant art, many other fluorescence dyes would be suitable for the present purposes.

The inventive methods can be used for various purposes. On the one hand, DMH applications can be carried out as explained in further detail herein below. The inventive methods can, however, also be used for diagnostic purposes. In the latter case, the immobilized nucleic acids contain, for example, nucleic acid sequences, the methylation sites of which are not methylated compared to the normal state, if a defined disease occurs. In this context, fragments of the tested DNA hybridizing therewith will indicate that a disease occurs, because the fragments are exclusively those fragments that are not methylated in the tested DNA. Of course, immobilized nucleic acids may also or additionally be used, which are methylated in case of a disease. Then, by non-hybridization, exclusion information is obtained. Further, it is possible to generate the immobilized nucleic acids by digestion with methylation-specific restriction enzymes, which cut the DNA, if a cytosine methylation exists.

According to alternate aspects of the invention, various DNA arrays can be used. In a preferred embodiment, arrays are used, as they are known from conventional methods. In particular aspects, these arrays comprise cloned CpG islands.

In a particularly preferred embodiment, oligo chips are used, and these are described below in more detail. Explicit reference to these applications is made.

For this variant, the DNA microarray may in principle carry immobilized nucleic acids, the methylation or non-methylation of which is correlated with a plurality of different defined diseases. Accordingly, the DNA of the patient is thereby simultaneously tested for the plurality of different diseases. Because of the complexity of such examinations, it is preferred that the DNA microarray carries nucleic acids containing either exclusively methylated or exclusively not methylated sequences, compared to the normal state.

In conjunction with such variants, the invention further provides a test kit for performing the inventive method, the kit comprising: i) a single restriction enzyme component, which comprises exclusively a methylation-specific restriction enzyme or several of such enzymes, and ii) a DNA microarray, which carries a plurality of different immobilized nucleic acids with a methylation site each at respectively assigned different locations on the DNA microarray, and the nucleic acids may contain at least one methylation site. The nucleic acids further contain nucleic acid sequences, which are not methylated or are methylated for a plurality of different defined diseases or a single defined disease, compared to the normal state. The defined disease may for instance be a specific cancer disease. A specific cancer disease is, for example, an organ-specific cancer disease, such as lung cancer, ovary cancer, scrotal cancer, prostate cancer, pancreas cancer, cancer of an organ of the digestive tract, etc. Suitable sequences with regard to all aspects of the invention are for example, described in the documents DE 20121979 U1, DE 20121978 U1, DE 20121977 U1, DE 20121975 U1, DE 20121974 U1, DE 20121973 U1, DE 20121972 U1, DE 20121971 U1, DE 20121970 U1, DE 20121969 U1, DE 20121968 U1, DE 20121967 U1, DE 20121966 U1, DE 20121965 U1, DE 20121964 U1, DE 20121963 U1, DE 20121961 U1, DE 20121960 U1, DE 10019173 A1, DE 10019058 A1, DE 10013847 A1, DE 10032529 A1, DE 10054974 A1, DE 10043826 A1, DE 10054972 A1, DE 10037769 A1, DE 10061338 A1, DE 10245779 A1, DE 10164501 A1, DE 10161625 A1, DE 10230692, DE 10255104, EP 1268855, EP 1283905, EP 1268857, EP 1294947, EP 1370685, EP 1395686, EP 1421220, EP 1451354, EP 1458893, EP 1340818, EP 1399589, EP 1478784, WO 2004/035803, and WO 2005/001141, all of which are incorporated by reference herein in their entirety.

In the test kit, one or several of the following components may in addition be included: i) a linker or several linkers, if applicable in a suitable solution, ii) substances or solutions for performing a PCR, iii) a dye or several dyes, if applicable with a coupling reagent, if applicable in a solution, iv) substances or solutions for performing a hybridization, and/or v) substances or solutions for performing a washing step.

II. Second Preferred Embodiment

The Use of Additional Non-Methylation-Specific Restriction Enzymes

A second particularly preferred embodiment of the inventive method for achieving the technical object, the reduction of complexity, the invention teaches and provides a method for making a mixture of fragments of a polynucleic acid, the method comprising:
  a) a solution comprising a polynucleic acid is prepared;
  b) optionally, a processing step is performed, in which substances that are not polynucleic acids are depleted, and/or the polynucleic acid is enriched;
  c) at least two different non-methylation-specific restriction enzymes are added to the solution, wherein the polynucleic acid is cut at restriction sites, for which the restriction enzymes are specific;
  d) fragments with a length of less than 50 bases are separated from the solution obtained in step c);

e) linkers are ligated to the fragments obtained in step d);

f) then one or at least two methylation-specific restriction enzymes are added to the solution obtained in step e), wherein the fragments are cut at cutting sites, which are capable of being methylated, but are not methylated; and g) the fragments obtained in step f) are subjected to an amplification step, wherein those fragments are amplified, which have not been cut in step f).

Preferably, fragments having a length in the range from 50 bases to 5,000 bases are selectively enriched.

Accordingly, a solution with a mixture of fragments of a polynucleic acid is obtained, which is particularly suitable for DMH. Surprisingly, despite the increase of the number of cuts, an increase of the number of interesting fragments (i.e., fragments comprising CpG islands) is achieved by using several different non-methylation-specific restriction enzymes, and the complexity (i.e., the number of the amplified fragments in the mixture and thus of the nucleic acids is simultaneously reduced).

Prior art methods, by contrast, have tried to reduce the complexity and to obtain interesting fragments by as few steps as possible with non-methylation-specific restriction enzymes. By means of the instant invention, a reduction of the complexity of the mixture (number of amplifiable nucleic acids in the mixture) up to a factor 10 is achievable (i.e., by a factor of maximum 10 better) relative to the prior art methods.

Preferably, in step c) three different non-methylation-specific restriction enzymes are added. It is additionally preferred, that at least one, and preferably all non-methylation-specific restriction enzymes cut recognition sequences having a length of four bases, and in particular recognition sequences that do not contain CG dinucleotide sequences. Using restriction enzymes with recognition sequences having a length of four bases facilitates the generation of fragments that are short and that are separable by purification, which reduces the complexity. Simultaneously, by using restriction enzymes with recognition sequences having a length of four bases, the number of potentially interesting fragments (i.e., fragments, which possibly comprise CpG islands, or amplifiable size fragments having a density of CG dinucleotides that is increased relative to the average CG density in the genome) is increased.

Advantageously, at least one, preferably all non-methylation-specific restriction enzymes generate sticky ends, in particular sticky ends with an overhang containing TA. Particularly preferred is the use of non-methylation-specific restriction enzymes, which cut a recognition sequence of four bases to sticky ends, and all restriction enzymes produce the same overhangs.

Alternatively, one or several non-methylation-specific restriction enzymes that produce sticky ends can be used in conjunction with one or several non-methylation-specific restriction enzymes that produce blunt ends, since a ligation of a fragment with a sticky end with a fragment with a blunt end is also possible.

Of course it is also possible to use only non-methylation-specific restriction enzymes that produce blunt ends, because in this case a ligation is also possible.

The non-methylation-specific restriction enzymes are preferably selected from at least two, and preferably three from the group consisting of "MseI, BfaI, Csp6I, Tru1I, Tvu1I, Tru9I, Tvu9I, MaeI and XspI". Particularly preferred is the use of a combination of MseI, BfaI and Csp6I.

In principle, step c) may be performed with common (i.e., simultaneous) addition of all non-methylation-specific restriction enzymes to the solution. Alternately, it is possible to add the restriction enzymes sequentially during step c).

In principle, for step f), every methylation-specific restriction enzyme can be used. This may be enzymes, which cut methylation-specific unmethylated DNA, or enzymes, which cut methylation-specific methylated DNA. Preferably, the methylation-specific restriction enzyme is selected from the group consisting of BisI, BstUI, BshI236I, AccII, BstFNI, McrBC, GlaI, MvnI, HpaII (HapII), HhaI, AciI, SmaI, HinP1I, HpyCH4IV, EagI and mixtures of two or more of the above enzymes. Preferred is a mixture containing the restriction enzymes BstUI, HpaII, HpyCH4IV and HinP1I.

In particular aspects, the inventive method is employed with a polynucleic acid that is a naturally occurring DNA. Preferably, this is a genomic DNA (e.g., a human genomic DNA).

Preferably, fragments with a length from 100 bases to 1,000 bases are selectively enriched in step e). Thereby, the optimum reduction of complexity is achieved, and wherein simultaneously effectively all potentially interesting fragments are preserved and/or enriched.

The invention further relates to a method for determining the methylation pattern of a polynucleic acid, in particular a genomic DNA from a tissue sample of a patient, the method comprising:

a) a method according to one embodiment of the invention is performed;

b) thereafter the selectively amplified fragments are coupled with a substance being detectable in a physical detection method;

c) a solution comprising the fragments of step b) is contacted with a DNA-microarray, which carries a plurality of different immobilized nucleic acids with at least one methylation site each at different, respectively assigned locations, under conditions, at which a hybridization of fragments with correlated immobilized nucleic acids takes place with defined stringency;

d) optionally, a washing step is performed;

e) such nucleic acids, to which fragments of the solution are hybridized, are detected using the physical detection method.

In such applications, the detectable substance may be a fluorescence dye, wherein the detection method then comprises selectively scanning for the fluorescence radiation transmitted by the fluorescence dye (one-dimensional or two-dimensional, depending on the arrangement of the different immobilized nucleic acids on the chip). The fluorescence dye may, for instance, be Cy3 and/or Cy5. A person of ordinary skill in the relevant art would recognize that many other suitable fluorescence dyes could be used.

Such inventive embodiments may be used for various purposes. On the one hand, DMH can be carried out, and further applications are given and described elsewhere in this application.

Alternatively, however, the inventive methods are used for diagnostic purposes. In the latter case, the immobilized nucleic acids contain, for example, nucleic acid sequences, the methylation sites of which are not methylated compared to the normal state, if a defined disease occurs. Accordingly, fragments of the tested DNA hybridizing therewith will indicate that a disease does not exist, because the fragments are exclusively those fragments that are methylated in the tested DNA (and therefore not cut, and are consequently amplifiable). Of course, immobilized nucleic acids may also or additionally be used, which are not methylated in case of a disease. Then, by non-hybridization, exclusion information is obtained.

In various aspects, different DNA arrays can be used. In a preferred embodiment, arrays are used, as they are known from conventional methods. In particular aspects, these arrays comprise cloned CpG islands.

In a particularly preferred embodiment, oligo chips are used, and these are described below in more detail. Explicit reference to these applications is made.

For this variant, the DNA microarray may in principle carry immobilized nucleic acids, the methylation or non-methylation of which is correlated with a plurality of different defined diseases. Accordingly, the DNA of the patient is simultaneously tested for the plurality of different diseases. Because of the complexity of such examinations, it is preferred that, with respect to each single defined disease, the DNA microarray exclusively carries nucleic acids containing either nucleic acid sequences that are methylated, or not methylated compared to the normal state for any single defined disease. Corresponding considerations apply for the case of the examination for response.

In conjunction with such variants, the invention further provides a test kit for performing the inventive method, the kit comprising: i) a first restriction enzyme component, which comprises at least two different non-methylation-specific restriction enzymes; ii) a second restriction enzyme component, which comprises exclusively a methylation-specific restriction enzyme or several of such enzymes; and iii) a DNA microarray, which carries a plurality of different immobilized nucleic acids at respectively assigned different locations on the DNA microarray, and the nucleic acids may comprise at least one methylation site. Preferably, the nucleic acids comprise nucleic acid sequences that, for a plurality of different defined diseases or a single defined disease, are either not methylated, or are methylated compared to the normal state. The defined disease may for instance be a specific cancer disease.

The test kit, may further comprise one or more of the following: i) a linker or several linkers, optionally in a suitable solution; ii) a ligase, optionally in a suitable solution; iii) substances or solutions for performing a PCR; iv) a dye or several dyes, optionally with a coupling reagent, optionally in a solution; v) substances or solutions for carrying out a hybridization; and/or vi) substances or solution for carrying out a washing step.

III. Third Particularly Preferred Embodiment

Combination of Complexity Reduction and Use of Oligochips

In both above embodiments, it is particularly preferred that oligochips are used. For achieving the technical object, the invention teaches a method for determining the methylation pattern of a polynucleic acid on the basis of an oligochip with the following steps:

a) a solution comprising a mixture of fragments of the polynucleic acid is made from a solution comprising a polynucleic acid (e.g. a solution comprising genomic DNA) using a non-methylation-specific restriction enzyme or several non-methylation-specific restriction enzymes and after adapter ligation, optionally using a methylation-specific restriction enzyme or a selection of methylation-specific restriction enzymes, wherein the composition of the fragment mixture depends on the methylation pattern of the polynucleic acid;

b) the fragments are amplified and coupled with a substance being detectable with an optionally physical detection method;

c) a solution comprising the fragments of step b) is contacted with a DNA microarray, which carries a plurality of different immobilized oligonucleotides, under conditions, at which a hybridization of fragments occurs with correlated immobilized nucleic acids under defined stringency, wherein the immobilized nucleic acids are selected from nucleic acids, which are specific for fragments of a genome, preferably the human genome, of a gene bank, wherein the fragments of the genome are obtainable by means of the restriction enzymes used in step a), and are localized on the DNA microarray at different respectively assigned positions;

d) optionally, a washing step is performed;

e) such immobilized nucleic acids, to which fragments of the solution are hybridized and/or to which fragments of the solution are not hybridized, are detected using the detection method;

F) optionally, from the detected hybridizations and/or non-hybridizations according to step E) the methylation pattern of the polynucleic acid being the educt of step A) is derived.

Significantly, the method according to the invention may be performed without a bisulfite treatment in step a) or before step a).

In a preferred embodiment, the immobilized nucleotides have a length of less than 200 bases. Therefore, in the following they are referred to as oligonucleotides.

By using oligonucleotides on the microarray, the microarray can be produced at relatively low expenses, namely by direct synthesis on the chip surface. The oligonucleotides may however also be prepared outside the chip surface, and may then be applied to the chip surface by a variety of art-recognized means. This procedure has the advantage that the identity and quality of the oligonucleotides can be investigated before using them, which will lead to very reproducible experiments. On the other hand, by this method, the same densities cannot be obtained as by the synthesis on the chip. In total, immediate advantages of the oligonucleotide arrays result thereby compared to the DNA array types used in the literature, not to speak of the flexibility of the design.

For oligo chip preparation, initially the desired different sequences of the oligonucleotides have to be defined. A spot on the substrate of the microarray is then assigned to each of the defined oligonucleotides. Then, at such spots, optionally the synthesis of the associated oligonucleotide is performed. It is in particular advantageous that by the preferred method according to the invention, the definition of the desired oligonucleotides can be made "in silico". In particular, regions of the genome with repeats can be excluded when defining the sequences of the oligonucleotides, and thus at last the capacity of the microarray can be optimized.

Further, in the context of current commercially available oligonucleotide microarrays or oligonucleotide chips, it is possible to examine a substantially larger number of potentially interesting methylation sites, than this was possible with a CGI clone array. Thus, by a single hybridization step with a corresponding array, nearly the full genome can be investigated for different methylation. By using a method for the matching oligo selection as described below, methylation differences can be detected by the above method even in regions, which have a CG density of 2% only. Therein, too, it is different from the known DMH method typically limited to the analysis of CpG islands having a CG density of at least 4% (Heisler L E, Torti D, Boutros P C, Watson J, Chan C, Winegarden N, Takahashi M, Yau P, Huang T H, Farnham P J, Jurisica I, Woodgett J R, Bremner R, Penn L Z, Der S D. CpG Island microarray probe sequences derived from a physical library are representative of CpG Islands annotated on the human genome (*Nucleic Acids Res.* 33:2952-61, 2005).

The oligonucleotides preferably have a length of 15 to 80 bases, in particular 20 to 30 bases.

The sequences of the oligonucleotides can in particular be defined by the following steps:

a) the genome of an organism is tested for first partial sequences, which are limited by cutting sites of the used non-methylation-specific restriction enzymes and have a length of 100 to 1,200 base pairs, and said first partial sequences are selected;

b) from the first partial sequences, are excluded those that contain more than 50% repeats, preferably partial sequences are excluded that contain more than 20% repeats, whereby a group of second partial sequences is formed, and where the steps a) and b) can be performed in any order.

For the case that methylation-specific restriction enzymes are further used for preparing the mixture of fragments, in a further step c), the selected second partial sequences are tested for cutting sites of the methylation-specific restriction enzymes used, and as third partial sequences those second partial sequences are selected, which contain such cutting sites, and wherein the steps a) to c) can be performed in any order.

These partial sequences correspond to the sequences of the fragments obtained in step a). In a preferred embodiment, they are characterized in that they contain at least one CG position within a methylation-specific restriction cutting site. Arbitrarily or according to further defined criteria, oligonucleotide sequences are thereby selected, which hybridize to these partial sequences (or their counter strand) or are identical to them (in order to then hybridize to the counter strand).

It is preferred that these oligonucleotides are intended for the synthesis on the DNA microarray. The above steps can be performed by means of simple programs based on publicly accessible gene databases. It is further preferred that several used oligonucleotide sequences hybridize to a fragment to be detected. Herein it is preferred that 3 to 30 oligonucleotides hybridize to a fragment. It is particularly preferred that 5 to 25 oligonucleotides hybridize to a fragment, and it is most particularly preferred that 10 to 20 oligonucleotides hybridize to a fragment.

In particular aspects, these oligo sequences overlap in part.

In a preferred embodiment, from among the possible oligonucleotide sequences, those are selected that have the smallest signal/noise ratio and/or the smallest cross hybridization rate.

It is preferred that the detectable substance is a fluorescence dye, and wherein the detection method comprises a scanning selective for the fluorescence radiation transmitted by the fluorescence dye, one-dimensional or two-dimensional, depending on the arrangement of the different immobilized nucleic acids on the chip. The fluorescence dye may be selected from the group consisting of "Cy3 and Cy5". A person of ordinary skill in the relevant art is will be familiar with many other suitable fluorescence dyes.

In another preferred embodiment, the detectable substance may however also be a biotin, which in the detection method interacts with another substance and is detected thereby (see e.g., "Gene Chip Mapping Assay Manual" of Affymetrix Inc.). Fragments from different samples are separately hybridized on the microarrays, since they cannot be distinguished by the detectable substance, thus two identical arrays are needed, which have then to be standardized for the comparative evaluation.

The fragments detected with the immobilized oligonucleotides preferably contain nucleic acid sequences, the methylation sites of which are not methylated or are methylated compared to the normal state if a defined disease occurs. It is however not necessary that the oligonucleotide itself contains this methylation site. The use of such oligonucleotides containing this methylation site is a alternate embodiment of the method.

The DNA microarray may exclusively carry oligonucleotides, which detect nucleic acid sequences (by hybridization), which are not methylated or are methylated compared to the normal state if a single defined disease occurs. It is however also imaginable that on a microarray, different sets of oligonucleotides are immobilized, which can detect not only different fragments being specifically methylated for a disease, but also different sets of fragments, which in turn are specifically methylated for different diseases or other conditions of interest, and thus the occurrence of a plurality of diseases or other conditions of interest, which are characterized by a differential methylation, can simultaneously be determined.

Other conditions of interest are, for instance, the risk to suffer from a certain disease, the prognosis of a certain type of a disease or the susceptibility to side effects of a certain type of treatment. Also detectable are determinations/statements about the type or the aggressiveness or progress of a disease, for instance of a tumor disease, or about the efficiency of a therapy, if these determinations/statements are based on methylation differences.

Further it is possible to simultaneously perform SNP analyses on the same microarray by means of another oligo set, and thus to generate either further information about conditions based on genetic differences (SNP differentiation) or about the type or the aggressiveness or progress of a disease, for instance a tumor disease, or about the efficiency of a therapy, if these statements are based on SNP differences.

The invention also relates to oligonucleotide arrays, the oligonucleotides of which were selected according to the above criteria.

The invention moreover relates to a method for preparing such arrays suitable for the methylation analysis, which is characterized by that the oligonucleotides immobilized on the surface of the array are subject to a selection, which is based on the method described above.

The invention further relates to a test kit for performing a method according to the invention, comprising the following components: a restriction enzyme component or several different restriction enzyme components, the restriction enzymes of which are suitable for preparing the fragments, and a DNA microarray, which carries a plurality of different immobilized oligonucleotides at respectively assigned different places on the DNA microarray. The oligonucleotides are characterized in that they are not longer than 200 bp.

In another test kit, a methylation-specific restriction enzyme is additionally included, the oligonucleotides on the chip are characterized in that they hybridize to fragments, which contain a restriction cutting site of at least one of the employed methylation-specific restriction enzymes.

The oligonucleotides on the array can specifically hybridize to fragment sequences containing nucleic acid sequences, which are not methylated or are methylated compared to the normal state if a single defined disease occurs. Thereby, the test kit would be suitable for the diagnosis of a specific disease. The disease may be, for example, a specific cancer disease.

One or several of the following components, which usually are used for a DMH analysis, may be additionally included: a linker or several linkers, if applicable in a suitable solution; substances or solutions for performing a PCR; a dye or several dyes, if applicable with a coupling reagent, if applicable in a solution; substances or solutions for performing a hybridization; and/or substances or solutions for performing a washing step.

The preparation of the fragments of the polynucleic acid may be performed in a variety of ways, for instance corresponding to the document Huang et al. (for bibliography see elsewhere in this specification). For instance, the following steps may be provided:

a) a solution containing the polynucleic acid is prepared;

b) as an option a processing step is performed, in which substances not being polynucleic acids are depleted and/or the nucleic acid is enriched;

c) one or preferably at least two different non-methylation-specific restriction enzymes are added to the solution, the polynucleic acid being cut at cutting sites being specific for the restriction enzymes;

d) the solution obtained in step c) is purified while separating small fragments;

e) linkers are ligated to the fragments obtained in step d);

f) then one or preferably at least two methylation-specific restriction enzymes are added to the solution obtained in step e), the fragments obtained in step d) being cut at cutting sites, which are capable of being methylated, but are not methylated;

and g) the fragments obtained in step f) are subjected after a further purification step performed as an option to an amplification step, those fragments being amplified, which were not cut in step f).\

In a preferred embodiment, in step d) of the above method, fragments having a length of less than 40 bp, preferably less than 70 bp, and more preferably less than 100 bp are separated from the solution obtained in step c).

In a preferred embodiment, the amplification in step g) takes place by means of primer molecules, which hybridize to the linkers introduced in step e), and of a polymerase under suitable PCR conditions.

Preferably, fragments having a length in the range from 50 bases to 5,000 bases, preferably from 70 to 2,000 bases, and more preferably from 100 to 1,200 bases are thus selectively enriched.

Thereby, a solution with a mixture of fragments of a polynucleic acid is obtained, which is particularly suitable for the method according to the invention. For this method, it is particularly preferred that in step c) at least two non-methylation-specific restriction enzymes are used. In the case of at least two non-methylation-specific restriction enzymes, on the one hand the number of those fragments is reduced that have a size suitable for the amplification (e.g. larger than 70 bp), since many fragments are cut to such a small size that they are for instance selected out by the purification steps and are no longer in the size window of the amplifiable nucleic acids. On the other hand, the number of those fragments is increased, which have a size suitable for the amplification (that is, are not too large for an efficient PCR amplification); that is, those fragments are reduced, which due to their large size are not amplifiable anymore. Thereby, the number of potentially interesting and amplifiable fragments again increases.

Despite the increase in the number of non-methylation-specific cuts, on the one hand the complexity related to the number of the fragments in the mixture to be amplified is reduced, and on the other hand an increase of the number of potentially interesting fragments (i.e. those possibly containing CpG islands or containing fragments having a higher density of CG dinucleotides compared to the average in the genome) is achieved. Compared to the use of only one non-methylation-specific restriction enzyme, a reduction of the complexity of the mixture (number of the nucleic acids in the mixture) to 1/10 is obtained; that is, by a factor 10 better compared to use of only one non-methylation-specific restriction enzyme.

This is an essential and substantial advantage over prior art methods, because a high complexity (i.e. amount of different nucleic acids or fragments) in the solution, to be tested for the presence of specific nucleic acids, will lead to unstable signals, increased cross hybridization and increased occurrence of non-specific hybridization.

Therefore, this embodiment of the method for preparing fragments in particularly preferred in conjunction with the use of oligonucleotide arrays.

Another essential advantage, which is caused by the use of several non-methylation-specific restriction enzymes, is that generally fewer very long fragments are kept (remain) for the subsequent step with methylation-specific restriction enzymes. Where the object is to identify those fragments that are methylated over longer regions to cover several CG dinucleotides (so-called co-methylated regions, they are of particular interest for the regulation of expression), then this is not possible, if there is even a single methylation-specific restriction cutting site in an unmethylated condition in this fragment. In this case, the fragment is cut into pieces and cannot be amplified anymore in the subsequent steps. Since it is now known that the so-called 'co-methylation' is often not 100%, and individual unmethylated CG cutting sites regularly exist, it is advantageous to preliminarily reduce the size of the fragments.

It is preferred that in step c) three different non-methylation-specific restriction enzymes are added.

It is further preferred that at least one, preferably all non-methylation-specific restriction enzymes cut recognition sequences having a length of four bases, in particular recognition sequences, which do not contain CG. By using restriction enzymes with recognition sequences having a length of four bases, the generation of fragments being long and thus disadvantageous for the amplification is prevented or reduced. Advantageously, at least one, preferably all non-methylation-specific restriction enzymes generate sticky ends, in particular sticky ends with an overhang containing TA. Particularly preferred is the use of non-methylation-specific restriction enzymes, which cut a recognition sequence of four bases to sticky ends, and all restriction enzymes produce the same overhangs. Alternatively, one or several non-methylation-specific restriction enzymes that produce sticky ends can be used in conjunction with one or several non-methylation-specific restriction enzymes that produce blunt ends, because a ligation of a fragment with a sticky end with a fragment with a blunt end is also possible. Alternatively, It is also possible to use only non-methylation-specific restriction enzymes that produce blunt ends, since in this case a ligation is also possible. The non-methylation-specific restriction enzymes are preferably selected from at least two, better three elements of the group consisting of "MseI, BfaI, Csp6I, Tru1I, Tvu1I, Tru9I, Tvu9I, MaeI and XspI". Particularly preferred is the use of a combination of MseI, Bfa1 and Csp6. In principle, the step c) may be performed with common, (i.e., simultaneous) addition of all non-methylation-specific restriction enzymes to the solution. Alternatively, the restriction enzymes can be sequentially added during the step c). In principle, every methylation-specific restriction enzyme can be used. Preferably, the methylation-specific restriction enzyme is selected from the group consisting of "BisI, BstUI, BshI236I, AccII, BstFNI, McrBC, GlaI, MvnI, HpaII (HapII), HhaI, AciI, SmaI, HinP1I, HpyCH4IV, and mixtures of two or more of the above enzymes". Preferred, is a mixture containing the restriction enzymes BstUI, HpaII, HpyCH4IV and HinP1I.

The method according to the invention will normally be used for a polynucleic acid that is a naturally occurring DNA. Preferably, a genomic DNA is used (e.g., a human genomic DNA).

Herein, the DNA microarray will typically carry a plurality of different nucleic acids containing known methylation sites. These can for instance be obtained from gene databases.

In detail, the following can be made. A first solution with fragments of a polynucleic acid, which originates from a tissue sample with diseased tissue, is prepared. A second solution with fragments of a polynucleic acid, which originates from a tissue sample of the same tissue(s) type adjacent to the diseased tissue, however being healthy tissue, is prepared. The first solution and the second solution are simultaneously or successively contacted with the DNA microarray and then hybridized. Such immobilized nucleic acids, in particular oligonucleotides, are selected, to which exclusively the fragments of the first solution or of the second solution are hybridized or not hybridized. By such a selected nucleic acid, DNA fragments are identified, which comprise regulatory and/or coding regions of one or more genes. Thus, the corresponding proteins, peptides or RNAs are derived.

IV. Combination of Oligochips and Further Enrichment Methods

Additional embodiments provide for use of oligochips in conjunction with other enrichment methods, for instance a method analogous to the "NotI representation" method according to WO 02/086163 (incorporated by reference herein in its entirety) or the method of the MS AP-PCR (Methylation Sensitive Arbitrarily-primed Polymerase Chain Reaction; Gonzalgo et al., *Cancer Res.* 57:594-599, 1997). Furthermore, enrichment may be performed by methods, which use the selective binding of substances to methylated DNA. The enrichment may occur by means of proteins, which methylation-specifically bind to the DNA, these may be MeCP2, MBD1, MBD2, MBD4 and Kaiso, or any domain thereof or methylation-specific antibodies, e.g. anti-5-methylcytosine anti-bodies. Further, a chromatin immunoprecipitation (ChIP) may be performed for the enrichment. However, even further substances may be used for the enrichment, for instance triplex-forming PNA or DNA oligomers. The mentioned methods will be considered in detail hereunder.

Consequently, this inventive embodiment for determining the methylation pattern of polynucleic acids is characterized by the following steps:

a) a solution comprising a mixture of fragments of the polynucleic acid is made from a solution comprising the polynucleic acid, e.g. a solution comprising genomic DNA, wherein the composition of the fragment mixture depends on the methylation pattern of the polynucleic acid;

b) the fragments of step a) are coupled with a substance being detectable with an optionally physical detection method, wherein optionally an amplification of the fragments may occur;

c) a solution comprising the fragments of step b) is contacted with a DNA microarray, which carries a plurality of different immobilized oligonucleotides, under conditions, at which a hybridization of fragments occurs with correlated immobilized nucleic acids under defined stringency, wherein the immobilized nucleic acids are selected from nucleic acids, which are specific for fragments of a genome, preferably the human genome, and are localized on the DNA microarray at different respectively assigned positions;

d) optionally, a washing step is performed;

e) such nucleic acids, to which fragments of the solution are hybridized and/or to which fragments of the solution are not hybridized, are detected using the detection method;

f) optionally, from the detected hybridizations and/or non-hybridizations according to step e) the methylation pattern of the polynucleic acid being the educt of step a) is derived.

Oligoarray.

The structure and preparation of the oligonucleotide arrays are described in detail above. Explicit reference is made to the corresponding applications.

The oligonucleotides preferably have a length of 15 to 80 bases, in particular 20 to 30 bases.

In a preferred embodiment, oligochips are used in combination with fragment enrichment methods, which comprise a digestion with non-methylation-specific restriction enzymes, or which comprise a first digestion with non-methylation-specific restriction enzymes and a second digestion with methylation-specific restriction enzymes (in detail see above).

The sequences of the oligonucleotides can in particular be defined by the following steps:

a) the genome of an organism is tested for first partial sequences, which are limited by cutting sites of the used non-methylation-specific restriction enzymes and have a length of 100 to 1,200 base pairs, and said first partial sequences are selected;

b) from the first partial sequences, those are excluded, which contain more than 50% repeats, preferably such partial sequences are excluded, which contain more than 20% repeats, whereby a group of second partial sequences is formed, and wherein the steps a) and b) can be performed in any order.

For the case that methylation-specific restriction enzymes are further used for preparing the fragments, preferably in another step c), the selected second partial sequences are tested for cutting sites of the used methylation-specific restriction enzymes, and as third partial sequences those second partial sequences are selected, which contain such cutting sites, and wherein the steps a) to c) can be performed in any order.

In another preferred variant of execution, oligochips are used in combination with fragment enrichment methods, which only comprise a digestion with methylation-specific restriction enzymes. Herein, the sequences of the oligonucleotides may in particular be defined by the following steps:

a) the genome of an organism is tested for first partial sequences, which are limited by cutting sites of the used methylation-specific restriction enzymes and have a length of 100 to 1,200 base pairs, and said first partial sequences are selected;

b) such partial sequences are excluded from the first partial sequences, which comprise more than 50% repeats, preferably, such partial sequences are excluded, which contain more than 20% repeats, whereby a group of second partial sequences is formed, and wherein the steps a) and b) can be performed in any order.

In another preferred variant of execution, oligochips are used in combination with fragment enrichment methods, wherein fragments are enriched by a digestion with a first restriction enzyme and simultaneously comprise a cutting site for a second restriction enzyme. Herein, the sequences of the oligonucleotides may in particular be defined by the following steps:

a) the genome of an organism is tested for first partial sequences, which are limited by cutting sites of one or several of the first used restriction enzymes and have a length of 100 to 1,200 base pairs, and said first partial sequences are selected;

b) such partial sequences are excluded from the first partial sequences, which comprise more than 50% repeats, preferably such partial sequences are excluded, which contain more than 20% repeats, whereby a group of second partial sequences is formed, and wherein the steps a) and b) can be performed in any order;

c) the selected second partial sequences are tested for cutting sites of the restriction enzymes used secondly, and as third partial sequences those second partial sequences are selected, which contain such cutting sites, and wherein the steps a) to c) can be performed in any order.

In principle, it is also possible to combine every oligochip with oligonucleotides defined by one of the three above methods with each enrichment method.

The partial sequences obtainable by the three mentioned methods may correspond to the sequences of the fragments obtained in step a). In a preferred embodiment, they are characterized in that they contain at least one CG position within a methylation-specific restriction cutting site. Arbitrarily or according to further defined criteria, oligonucleotide sequences are now selected, which hybridize to these partial sequences (or their counter strand) or are identical to them (in order to then hybridize to the counter strand).

It is preferred that these oligonucleotides are intended for the synthesis on the DNA microarray. The above steps can be performed by means of simple programs based on publicly accessible gene databases. It is further preferred that several oligonucleotide sequences used hybridize to a fragment to be detected. Herein it is preferred that 3 to 30 oligonucleotides hybridize to a fragment. It is particularly preferred that 5 to 25 oligonucleotides hybridize to a fragment, and it is most particularly preferred that 10 to 20 oligonucleotides hybridize to a fragment.

Alternately, said oligo sequences overlap in part.

In a preferred embodiment, exclusively oligonucleotide sequences are used for preparing the microarray, which hybridize in identical defined distances to the complementary DNA to be tested. In this way, a so-called "tiling array" is created, as described for instance in Kapranov P, Cawley S E, Drenkow J, Bekiranov S, Strausberg R L, Fodor S P, Gingeras T R. Large-scale transcriptional activity in chromosomes 21 and 22 (*Science* 296:916-9, 2002). Thereby it is possible, in contrast to the detection with specific fragments, to analyze the complete region of a very large partial sequence, and thus conclusions can be drawn with regard to the presence or absence of a comethylation.

In a preferred embodiment, among the possible oligonucleotide sequences those are selected, which have the smallest signal/noise ratio and/or the smallest cross hybridization rate.

Labeling.

It is preferred that the detectable substance is a fluorescence dye, and wherein the detection method comprises a selective scanning for the fluorescence radiation transmitted by the fluorescence dye, one-dimensional or two-dimensional, depending on the arrangement of the different immobilized nucleic acids on the chip. The fluorescence dye may be selected from the group consisting of "Cy3 and Cy5". A person of ordinary skill in the art will be familiar with many other suitable fluorescence dyes.

In another preferred embodiment, the detectable substance may however also be a biotin, which in the detection method interacts with another substance and is detected thereby (see e.g. "Gene Chip Mapping Assay Manual" of Affymetrix Inc.). Fragments from different samples are separately hybridized on the microarrays, because they cannot be distinguished by the detectable substance, thus two identical arrays are needed, which have then to be standardized for the comparative evaluation.

In a preferred embodiment of the invention, labeling is performed with the detectable substance by amplification of the fragments. According to particular aspects, so-called whole genome amplification methods are used (WGA—whole genome amplification, survey in: Hawkins et al.: Whole genome amplification—applications and advances. *Curr Opin Biotechnol.* 2002 Feb.; 13(1):65-7). In these methods, the fragments are amplified by means of a DNA polymerase and primers. The primers may be linker-specific primers, random primers or degenerated primers.

Up to now, different WGA methods are described. In the so-called primer extension preamplification (PEP), the amplification is performed by means of a random mixture of oligonucleotide primers having a length of approx. 15 nucleotides (Zhang et al.: Whole genome amplification from a single cell: implications for genetic analysis. *Proc Natl Acad Sci USA* 89:5847-51, 1992). In the DOP-PCR (degenerate oligonucleotide primed polymerase chain reaction), however, only a degenerate primer is used (cf: Telenius et al.: Degenerate oligonucleotide-primed PCR: general amplification of target DNA by a single degenerate primer; *Genomics* 13: 718-25, 1992). Another WGA method is the so-called linker/adaptor-PCR. Therein, linkers are ligated to fragments. In the subsequent amplification, primers are used, which specifically bind to the linkers (survey in: Cheung and Nelson: Whole genome amplification using a degenerate oligonucleotide primer allows hundreds of genotypes to be performed on less than one nanogram of genomic DNA. *Proc Natl Acad Sci USA.* 93:14676-9, 1996). The above WGA methods based on PCR have several drawbacks, however. For instance a generation of unspecific amplification artifacts may occur. Further, often an incomplete coverage only of all genome regions will take place. Further, in part short DNA fragments with lengths of less than 1 kB only are generated. (cf: Dean et al.: Comprehensive human genome amplification using multiple displacement amplification. *Proc Natl Acad Sci USA.* 99:5261-6, 2002). The most powerful method for a whole genome amplification is therefore at present the isothermal "Multiple Displacement Amplification" (MDA, cf: Dean et al. 2002 as above; U.S. Pat. No. 6,124,120). The DNA is reacted with random primers and a DNA polymerase. Polymerases are used here, which are capable to displace the non-template strand of the DNA double strand during the amplification (e.g. a φ29 polymerase). The displaced strands in turn serve as a matrix for the extension of further primers. By using this method, an amplification by more than 5,000 is possible. The average product length is more than 10 kB, and the amplification is distributed rather uniformly over the complete pool of fragments. Commercial kits for the MDA are at present available from two suppliers ("GenomiPhi" from Amersham Biosciences, www4.amershambiosciences.com; "Repli-g" from Molecular Staging, www.molecularstaging.com).

Execution of the Array.

The fragments detected with the immobilized oligonucleotides preferably comprise nucleic acid sequences, the methylation sites of which are not methylated or are methylated compared to the normal state, if a defined disease exists.

For this purpose, it not necessary that the oligonucleotide itself comprises this methylation site. The use of such oligonucleotides, which comprise said methylation site, is one possible example of execution of the method.

The DNA microarray may exclusively carry oligonucleotides, which detect nucleic acid sequences (by hybridization), which are not methylated or are methylated compared to the normal state, if a defined disease exists. It is however also imaginable that on a microarray different sets of oligonucleotides are immobilized, which cannot only detect different fragments, which are specifically methylated for a disease, but also different sets of fragments, which in turn are specifically methylated for different diseases or other conditions of interest, and thus the existence of a plurality of diseases or other conditions of interest characterized by a differential methylation can simultaneously be determined.

Other conditions of interest are for instance the risk to suffer from a certain disease, the prognosis of a certain type of a disease or the susceptibility to side effects of a certain type of treatment. Also detectable are statements/determinations about the type or the aggressiveness or progress of a disease, for instance of a tumor disease, or about the efficiency of a therapy, if these statements/determinations are based on methylation differences.

Further it is possible to simultaneously perform SNP analyses on the same microarray by means of another oligo set, and thus to generate either further information about conditions based on genetic differences (SNP differentiation) or about the type or the aggressiveness or progress of a disease, for instance a tumor disease, or about the efficiency of a therapy, if these statements are based on SNP differences.

The invention moreover relates to a method for preparing such arrays suitable for the methylation analysis, which is characterized by that the oligonucleotides immobilized on the surface of the array are subject to a selection, which is based on the method described above.

Test Kits.

The invention further relates to a test kit for performing a method according to the invention, comprising a container and a DNA microarray component, which carries a plurality of different immobilized oligonucleotides at respectively assigned different places on the DNA microarray, and the oligonucleotide may contain at least one methylation site. The oligonucleotides are further characterized by that they are not longer than 200 bp.

Additional components of the test kit may be one or several of the following components:

a restriction enzyme component or several different restriction enzyme components, the restriction enzymes of which are suitable for preparing the fragments;

preferably a single restriction enzyme component, which comprises exclusively one methylation-specific restriction enzyme or several of such enzymes, preferably of a first restriction enzyme component, which comprises at least two different non-methylation-specific restriction enzymes;

a second restriction enzyme component, which comprises exclusively one methylation-specific restriction enzyme or several of such enzymes;

a protein component, the effective component of which binds DNA methylation-specifically; and/or a triplex-forming component, the effective component of which distinguishes between methylated and non-methylated DNA.

Another test kit additionally comprises a methylation-specific restriction enzyme, wherein the oligonucleotides on the chip are characterized in that they hybridize to fragments, which comprise a restriction cutting site of at least one of the used methylation restriction enzymes.

The oligonucleotides on the array can specifically hybridize to fragment sequences, which comprise nucleic acid sequences, which are not methylated or are methylated compared to the normal state, if a single defined disease exists. Thereby the test kit would be suitable for the diagnosis of a specific disease. The disease may be a specific cancer disease.

One or several of the following components, which usually are employed for a DNA enrichment, may in addition be comprised: a linker or several linkers, if applicable in a suitable solution; substances or solutions for performing a ligation; substances or solutions for performing a column chromatography; substances or solutions for performing an immunoprecipitation; substances or solutions for performing a PCR; a dye or several dyes, if applicable with a coupling reagent, if applicable in a solution; substances or solutions for performing a hybridization; and/or substances or solutions for performing a washing step.

The invention further relates to a test kit for performing a method according to the invention, comprising a container and a DNA microarray component, which carries a plurality of different immobilized nucleic acids at respectively assigned different places on the DNA microarray, wherein the nucleic acids may comprise at least one methylation site.

Additional components of the test kit may be one or several of the following components:

one restriction enzyme component or several different restriction enzyme components, the restriction enzymes of which are suitable for preparing the fragments;

preferably one single restriction enzyme component, which comprises exclusively one methylation-specific restriction enzyme or several of such enzymes, preferably of a first restriction enzyme component, which comprises at least two different non-methylation-specific restriction enzymes;

a second restriction enzyme component, which comprises exclusively one methylation-specific restriction enzyme or several of such enzymes;

a protein component, the effective component of which binds DNA methylation-specifically; and/or a triplex-forming component, the effective component of which distinguishes between methylated and non-methylated DNA.

In another test kit, in addition a methylation-specific restriction enzyme is comprised, the nucleic acids on the chip are characterized by that they hybridize to fragments, which comprise a restriction cutting site of at least one of the used methylation restriction enzymes.

The nucleic acids on the array can specifically hybridize to fragment sequences, which comprise nucleic acid sequences, which are not methylated or are methylated compared to the normal state, if a single defined disease exists. Thereby the test kit would be suitable for the diagnosis of a specific disease. The disease may be a specific cancer disease.

One or several of the following components, which usually are employed for a DNA enrichment, may in addition be comprised: a linker or several linkers, if applicable in a suitable solution; substances or solutions for performing a ligation; substances or solutions for performing a column chromatography; substances or solutions for performing an immunoprecipitation; substances or solutions for performing a PCR; a dye or several dyes, if applicable with a coupling reagent, if applicable in a solution; substances or solutions for performing a hybridization; and/or substances or solutions for performing a washing step.

Preparation of the Fragments.

The preparation of the fragments of the polynucleic acid may be performed in the most various ways. According to the invention, an enrichment of methylated or not methylated fragments is performed. The enrichment may be made in various ways. Substantially, on the one hand, an enrichment occurs methylation-specifically by targeted treatment of the DNA with restriction enzymes, and on the other hand, by bringing the DNA into contact with substances specifically binding methylated or unmethylated sequences.

Preparation of the Fragments by Restriction Enzyme Treatment.

According to the invention, several methods can be used for the enrichment by specific treatment of the DNA with restriction enzymes. Several methods have already been described above.

Method I):

In a preferred embodiment, the enrichment of methylated or unmethylated fragments occurs by digestion of the DNA with at least one methylation-specific restriction enzyme without previous addition of a non-methylation-specific restriction enzyme. For instance, the following steps may be provided:

a) a solution comprising the polynucleic acid is prepared;

b) optionally, a processing step is performed, in which substances that are not polynucleic acids, are depleted, and/or the polynucleic acid is enriched;

c) a methylation-specific restriction enzyme or several methylation-specific restriction enzymes are added to the solution without previous addition of a non-methylation-specific restriction enzyme, wherein the polynucleic acid is cut to fragments at restriction sites, which are capable of being methylated, but are not methylated; and d) the fragments obtained in step c) are subjected to an amplification step, and fragments having a length in the range from 50 bases to 5,000 bases are selectively enriched.

After the restriction, adapters are ligated to the fragments. Then an amplification of the fragmented DNA is performed, and simultaneously a labelling of the fragments by means of a detectable substance can be performed.

Optionally, fragments after adapter ligation are subject to a digestion with the same restriction enzyme or enzymes as used in step c) before amplification. This has the advantage that religated fragments are digested while fragment-adapter ligations remain unaffected.

As methylation-specific restriction enzymes, enzymes may be used that only cut if their recognition sequence is unmethylated. A person of ordinary skill in the art is familiar with the respective restriction enzymes. Examples for the used enzymes are: BstUI, BshI236I, AccII, BstFNI, MvnI, HpaII (HapII), HhaI, AciI, SmaI, HinP1I, HpyCH4IV, or combinations of one or more of said enzymes are used. According to particular aspects, such restriction enzymes may also be used that only cut if a methylated recognition sequence exists. A person or ordinary skill in the art will be familiar with the respective restriction enzymes. Here, as examples only, McrBC (New England Biolabs) and the recently identified BisI (SibEnzyme Ltd., www.science.sibenzyme.com/article8_article_7_1.phtml) and GlaI (SibEnyzme Ltd., www.science.sibenzyme.com/article8_article_11_1.phtml) are mentioned. The use of further enzymes not yet identified is imaginable, as far as they methylation-specifically cut, if methylated or unmethylated recognition sequences exist. Of course also a mixture of said enzymes is applicable.

By this method, fragments having a length in the range from 50 bases to 5,000 bases, preferably however from 50 to 2,000 bases, more preferably from 80 to 2,000, most preferably from 100 to 2,000 bases, and in particular from 100 to 1,000 bases are selectively enriched.

In the specified length window, thus a reduction of the complexity by a factor greater than 100 is achievable. This is also based on the fact that methylated sequence regions (or in another case unmethylated sequence regions) and sequence regions without recognition sequences of the methylation-specific restriction enzymes used are not cut and consequently form fragments, the length of which is regularly above the upper limits of the amplification window. In contrast thereto, regions with unmethylated recognition sites (restriction enzyme, which cuts, if an unmethylated recognition sequence exists) are cut and form fragments having a length below the upper limit of the amplification window. The same will of course happen in the case of restriction enzymes, which only cut if their recognition sequences are methylated. Further, no potentially interesting fragments are non-methylation-specifically cut and thereby reduced to a length below the lower limit of the window. Consequently, all interesting fragments, i.e. those with potentially hypermethylated or hypomethylated sites, are available for the following analyses. Finally, the full process is simplified, since less restriction enzymes are used. It is even possible to perform all reactions up to the hybridization on a DMH chip in one vessel (one tube process). Consequently, processing is simplified and considerably faster. Finally, the number of potential error sources in the process is substantially reduced.

Method II.

In a preferred embodiment, the enrichment of methylated or unmethylated fragments occurs by digestion with non-methylation-specific restriction enzymes and after ligation of adapters to the fragments, if applicable with methylation-specific enzymes. For instance, the following steps may be provided:

a) a solution comprising the polynucleic acid is prepared;

b) optionally, a processing step is performed, in which sustances that are not polynucleic acids, are depleted, and/or the polynucleic acid is enriched;

c) one or preferably at least two different non-methylation-specific restriction enzymes are added to the solution, wherein the polynucleic acid is cut at cutting sites being specific for the restriction enzymes;

d) the solution obtained in step c) is purified while separating small fragments;

e) linkers are ligated to the fragments obtained in step d);

f) then one or preferably at least two methylation-specific restriction enzymes are added to the solution obtained in step e), the fragments obtained in step d) being cut at cutting sites, which are capable of being methylated, but are not methylated, or the fragments obtained in step d) being cut at cutting sites, which are capable of being methylated and are actually methylated; and g) the fragments obtained in step f) are subjected after a further purification step performed as an option to an amplification step, those fragments being amplified, which were not cut in step f).

In a preferred embodiment, in step d) of the above method, fragments having a length of less than 40 bp, preferably less than 70 bp, particularly preferably less than 100 bp are separated from the solution obtained in step c).

In a preferred embodiment, the amplification in step g) takes place by means of primer molecules, which hybridize to the linkers introduced in step e) and of a polymerase under suitable PCR conditions.

Preferably, thus fragments having a length in the range from 50 bases to 5,000 bases, preferably however from 70 to 2,000 bases, and in particular from 100 to 1,200 bases are selectively enriched.

Thereby, a solution with a mixture of fragments of a polynucleic acid is obtained, which is particularly suitable for the method according to the invention. For this method, it is particularly preferred that in step c) at least two non-methylation-specific restriction enzymes are used. In the case of at least two non-methylation-specific restriction enzymes, on the one hand the number of those fragments is reduced, which have a size suitable for the amplification (e.g. larger than 70 bp), since many fragments are cut to such a small size that they are for instance selected out by the purification steps and are no longer in the size window of the amplifiable nucleic acids. On the other hand, the number of those fragments is increased, which have a size suitable for the amplification (that is, are not too large for an efficient PCR amplification), i.e. those fragments are reduced, which due to their large size are not amplifiable anymore. Thereby, the number of potentially interesting and amplifiable fragments again increases.

Despite the increase in the number of non-methylation-specific cuts, on the one hand the complexity related to the number of the fragments in the mixture to be amplified is reduced, and on the other hand an increase of the number of potentially interesting fragments (i.e. possibly containing CpG islands or containing fragments having a higher density of CG dinucleotides compared to the average in the genome) is achieved. Compared to the use of only one non-methylation-specific restriction enzyme, a reduction of the complexity of the mixture (number of the nucleic acids in the mixture) to 1/10 is obtained (i.e. by a factor 10 better than when using only one non-methylation-specific restriction enzyme).

This is an essential advantage over prior art methods, since a high complexity (i.e. amount of different nucleic acids or fragments) in the solution, which is to be tested for the presence of specific nucleic acids, will lead to unstable signals, increased cross hybridization and increased occurrence of unspecific hybridization. Therefore, this embodiment of the method for preparing the fragments is particularly preferred in conjunction with the use of oligonucleotide arrays.

Another essential advantage, which is caused by the use of several non-methylation-specific restriction enzymes, is that generally fewer very long fragments are maintained for the step with methylation-specific restriction enzymes. Where the object is to identify those fragments, which are methylated over longer regions to several CG dinucleotides (so-called co-methylated regions, of particular interest for the regulation of the expression), then this is not possible if there is even a single methylation-specific restriction cutting site in an unmethylated condition in this fragment. In this case, the fragment is cut into pieces and cannot be amplified anymore in the following. Because it is now known that the so-called co-methylation is often not 100% and individual unmethylated CG cutting sites regularly exist, it is advantageous to preliminarily reduce the size of the fragments.

Preferably, in step c), three different non-methylation-specific restriction enzymes are added.

It is further preferred that at least one, preferably all non-methylation-specific restriction enzymes cut recognition sequences having a length of four bases, in particular recognition sequences, which do not contain CG. By using restriction enzymes with recognition sequences having a length of four bases, the generation of fragments being short and thus separable by purification is increased, which reduces the complexity. Simultaneously, by using restriction enzymes with recognition sequences having a length of four bases, the number of potentially interesting fragments (i.e. fragments, which possibly comprise CpG islands or fragments with a density of CG dinucleotides with an amplifiable size being increased compared to the average in the genome) is increased.

Advantageously, at least one, preferably all non-methylation-specific restriction enzymes generate sticky ends, in particular sticky ends with an overhang containing TA. Particularly preferred is the use of non-methylation-specific restriction enzymes, which cut a recognition sequence of four bases to sticky ends, and all restriction enzymes produce the same overhangs. Alternately, one or several non-methylation-specific restriction enzymes that produce sticky ends are used in conjunction with one or several non-methylation-specific restriction enzymes that produce blunt ends, since a ligation of a fragment with a sticky end with a fragment with a blunt end is also possible. Of course it is also possible to use only non-methylation-specific restriction enzymes, which produce blunt ends, since in this case, too, a ligation is possible. The non-methylation-specific restriction enzymes are preferably selected from at least two, better three from of the group consisting of MseI, BfaI, Csp6I, Tru1I, Tvu1I, Tru9I, Tvu9I, MaeI and XspI. Particularly preferred is the use of a combination of MseI, Bfa1 and Csp6. In principle, the step c) may be performed with common (i.e. simultaneous) addition of all non-methylation-specific restriction enzymes to the solution. It is also possible to add the restriction enzymes sequentially to the solution during the step c). In principle, every methylation-specific restriction enzyme can be used. Preferably, the methylation-specific restriction enzyme is selected from the group consisting of BisI, BstUI, BshI236I, AccII, BstFNI, McrBC, GlaI, MvnI, HpaII (HapII), HhaI, AciI, SmaI, HinP1I, HpyCH4IV, and mixtures of two or more of the above enzymes. Preferred is a mixture containing the restriction enzymes BstUI, HpaII, HpyCH4IV and HinP1I.

Method III):

In a preferred embodiment, the enrichment of the unmethylated fragments may substantially occur by means of the method of the "NotI representation" method according to WO 02/086163 (incorporated by reference herein in its entirety). In the "NotI representation" method, genomic DNA is digested with suitable restriction enzymes or with BamHI and BgIII. After inactivation of the enzymes, the fragments are circularized by self-ligation. The circularized DNA is then subjected to another digestion with the methylation-specific restriction enzyme NotI. This enzyme cuts the DNA only if its recognition sequence is unmethylated. Therefore, the majority of all circularized fragments is not digested and continues being circularized, since the fragments either do not contain a NotI cutting site, or they contain a methylated NotI cutting site. Only fragments with an unmethylated NotI cutting site are linearized by this step. To said fragments linearized again, NotI-specific linkers (adapters) are ligated, by means of which the fragments can be amplified in a subsequent PCR. In this way it is possible to enrich fragments, which have unmethylated cutting sites.

As mentioned above (prior art), CpG dinucleotides are concentrated in CpG islands. a person skilled in the art is familiar with that normally all CpG dinucleotides within a CpG island have the same methylation state (co-methylation), i.e. they are either all methylated or all unmethylated (for comparison see Eads C A, Danenberg K D, Kawakami K, Saltz L B, Blake C, Shibata D, Danenberg P V, Laird P W. MethyLight: a high-throughput assay to measure DNA methylation. Nucleic Acids Res. 2000 Apr. 15; 28(8); or Raykan V K, Hildmann T, Novik K L, Lewin J, Tost J, Cox A V, Andrews T D, Howe K L, Otto T, Olek A, Fischer J, Gut I G, Berlin K, Beck S. DNA methylation profiling of the human major histocompatibility complex: a pilot study for the human epigenome project. PLoS Biol. 2004 December; 2(12)). By the enrichment of fragments with unmethylated NotI cutting sites, thus unmethylated fragments are enriched.

Method IV:

In a preferred embodiment, the enrichment of the unmethylated fragments may essentially occur according to the MS AP-PCR (Methylation Sensitive Arbitrarily-primed Polymerase Chain Reaction). a person of ordinary skill in the art will be familiar with this method, which was initially described by Gonzalgo et al., Cancer Res. 57:594-599, 1997. In this method, genomic DNA is digested with one or several restriction enzymes, for instance HpaII. The fragments thus obtained are used in a PCR amplification, and the used primers arbitrarily bind to the DNA (random primers) and further are CG-rich. By using such arbitrary CG-rich primers, preferably DNA sections are amplified that contain CG dinucleotides.

Enrichment of DNA by Means of Substances, which Bind to Methylated DNA.

In a preferred variant, the enrichment of the methylated or not methylated fragments may occur by using substances, which selectively bind to methylated or not methylated DNA. The binding may take place in a sequence-specific manner as well as in a sequence-unspecific manner. After binding to the substances, the bound DNA can be separated from the unbound DNA. Depending on whether the DNA to be detected is methylated or unmethylated, the bound or the unbound fraction can further be analyzed.

For the method according to the invention, different substances methylation-specifically binding to the DNA may be used.

Enrichment of DNA by Means of Proteins:

In a preferred embodiment, the enrichment occurs by means of proteins or their domains methylation-specifically binding to the DNA. Several such proteins are known, inter alia MeCP2, MBD1, MBD2, MBD4 and Kaiso (survey in: Shiraishi et al. Methyl-CpG binding domain column chromatography as a tool for the analysis of genomic DNA methylation. *Anal Biochem.* 329:1-10, 2004; incorporated by reference herein in its entirety; Henrich et Tweedie: The methyl-CpG binding domain and the evolving role of DNA methylation in animals. *Trends Genet.* 19:269-77, 2003; both incorporated by reference herein in its entirety).

By means of proteins methylation-specifically binding to the DNA, a methylation-specific enrichment may occur in various ways. It is for instance possible to use proteins specifically binding methylated DNA as well as proteins specifically binding unmethylated DNA. Further, it is possible to bind that DNA that is to be detected later. For this purpose, first the unbound DNA is separated, and then the bound DNA is removed from the protein. It is also possible to bind the background DNA to the protein and to remove it then from the reaction batch. As well, a combination of proteins is possible, wherein a protein specifically binds methylated DNA, and another protein specifically binds unmethylated DNA. This has the advantage that simultaneously unmethylated DNA and methylated DNA are enriched, whereas DNA with no or few CpG positions are separated.

The protein binding and the separation of the bound and unbound DNA may take place in various ways. It is for instance possible to bind the proteins to a solid surface, for instance in the form of beads for the separation in the batch method or in the form of a column (cf: Cross et al., *Nature Genetics* 6:236-244, 1994). The unbound DNA can then be removed by washing steps. Further it is possible to have the binding to the proteins take place in the solution, and then to separate the DNA protein complexes by usual methods such as centrifugation or chromatography from the unbound DNA. a person skilled in the art is familiar with biochemical methods to be used, for instance by using biotinylated proteins or proteins provided with Histidine-tag (for instance Gretch et al. *Anal Biochem* 163:270-7, 1987; Janknecht et al. *Proc. Natl Acad Sci USA* 88:8972-6, 1991).

In a particularly preferred embodiment, the enrichment occurs by the so-called MDB column chromatography, which is described in detail by Shiraishi et al., 2004, ibid. Explicit reference is made to this publication.

The methyl-CpG-binding domain of the MeCP2 protein can be used for this purpose, said domain specifically binding methylated, not however unmethylated or hemimethylated cytosines. The corresponding domain expressing in vitro may for instance be bound to a modified agarose surface by additional histidine residues. The domain detects sequence-unspecifically methylated CpG positions. The binding of the methylated DNA to the column occurs in dependence on the methylation degree and the density of the CpG positions. The bound methylated DNA molecules can then be eluted by increasing the salt concentration and subsequently analyzed (see in detail: Shiraishi et al. 2004, ibid.). Besides that, it is also possible to analyze the unbound, unmethylated fraction.

Besides that, it is also possible to enrich methylated and unmethylated DNA by means of the CXXC-3 domain of the MBD1 protein. This domain can sequence-unspecifically bind to unmethylated CpG positions (Jørgensen, H. F., Ben-Porath, I., Bird, A. P. *Molecular and Cellular Biology,* 3387-3395, 2004). The corresponding domain expressed in vitro may for instance be bound by additional histidine residues to a modified agarose surface. The binding of the unmethylated DNA to the column occurs in dependence on the methylation degree and the density of the CpG positions. The bound unmethylated DNA molecules can then be eluted by increasing the salt concentration and subsequently analyzed.

Additionally, it is also possible to analyze the unbound, methylated fraction.

In a particularly preferred embodiment, the enrichment occurs by using several different proteins or protein domains in combination. In particular it is preferred to first enrich unmethylated DNA by means of a column, to which the CXXC-3 domain of the MBD1 protein is coupled. The non binding DNA may then be used to enrich methylated DNA. In this way, it is possible to simultaneously enrich unmethylated DNA and methylated DNA, and further DNA is separated, which has no or only few CpG positions.

Additionally, it is possible first to enrich methylated DNA and thereafter unmethylated DNA. In this case, too, DNA is separated, which has no or only few CpG positions.

According to the principle named above, other proteins or protein domains methylation-specifically binding to DNA may also be used for the enrichment, in particular proteins sequence-specifically binding to CpG positions, for instance by means of the kaiso protein, which detects symmetrically methylated CpGpCpG positions.

Besides the MDB proteins mentioned above, in principle further proteins methylation-specifically detecting DNA may also be used. Thereto belong for instance restriction enzymes or methyltransferases. It is imaginable that those parts of said enzymes, which are responsible for the methylation-specific binding, are used for an enrichment without the corresponding active center.

Enrichment of DNA by Means of Antibodies:

In another preferred embodiment, the enrichment occurs by methylation-specific antibodies. Anti-5-methylcytosine antibodies are known and commercially available since long times (www.abcam.com; Abcam Inc; One Kendall Square; Bldg. 200, 3$^{rd}$ Floor; Cambridge, Mass. 02139). These antibodies may also be bound to a column or be bound in a solution to the DNA by the known methods. Details thereof are known to a person skilled in the art (for instance Fisher et al. *Nucleic Acids Res.* 32:287-97, 2004).

Moreover, an immunoprecipitation may be performed with anti-5-methylcytosine antibodies. The DNA antibody complexes are precipitated in a suitable way, for instance with corresponding secondary antibodies. The fragments thus enriched are released from the proteins, for instance, by proteinase K digestion.

In one embodiment, the DNA may be preliminarily randomly or not randomly fragmented, and this can take place in an art-recognized manner. As a random fragmentation method, the treatment with ultrasound or shearing is particularly preferred. As a non-random fragmentation method, a fragmentation with methylation-specific restriction enzymes is particularly preferred. In principle, every methylation-specific restriction enzyme can be used. Preferably, the methylation-specific restriction enzyme is selected from the group consisting of BisI, BstUI, BshI236I, AccII, BstFNI, McrBC, GlaI, MvnI, HpaII (HapII), HhaI, AciI, SmaI, HinP1I, HpyCH4IV and mixtures of two or more of said enzymes.

Enrichment of DNA by Chromatin Immunoprecipitation:

In a preferred embodiment, a chromatin immunoprecipitation (ChIP) is performed for the enrichment. (Details of this method are known to persons skilled in the art and can for instance be found in: Matarazzo et al. In vivo analysis of DNA methylation patterns recognized by specific proteins: coupling CHIP and bisulfite analysis. Biotechniques. 37:666-8, 670, 672-3, 2004). An immunoprecipitation with antibodies is performed, which are directed against 5-methylcytosine-binding proteins. Said proteins are the proteins mentioned above already: inter alia MeCP2, MBD1, MBD2, MBD4 and Kaiso (survey in: Shiraishi et al., ibid.).

Essentially, this method is based on the fact that in the presence of protease inhibitors, a fixation of the proteins to the DNA takes place, for instance by formaldehyde. After an ultrasonic treatment, the immunoprecipitation is performed with antibodies, which specifically detect methylation-specific proteins. This may for instance be made with anti-MeCP2 antibodies (Santa Cruz Biotechnology, Santa Cruz, Calif., USA). The DNA/protein complexes are then precipitated with protein A sepharose or suitable secondary antibodies. The separation of the protein from the DNA occurs in a conventional way, e.g. by heating or adding proteinase K.

In a preferred variant, the DNA is purified and fragmented in a suitable way by restriction digestion. Thereafter, an incubation with the 5-methylcytosine binding proteins is performed. Then the immunoprecipitation takes place as described above.

In another preferred variant, the DNA/protein complexes are isolated before the second precipitation step by suitable physical methods such as ultracentrifugation. A respective kit is already commercially available (Panomics, Inc., Redwood City, Calif., USA), and may be used for the method according to the invention.

In one embodiment, the DNA may be randomly or not randomly fragmented. (e.g., in any suitable art-recognized manner). As a random fragmentation method, the treatment with ultrasound or shearing is particularly preferred. As a non-random fragmentation method, a fragmentation with methylation-specific restriction enzymes is particularly preferred. In principle, every methylation-specific restriction enzyme may be used. Preferably, the methylation-specific restriction enzyme is selected from the group consisting of BisI, BstUI, BshI236I, AccII, BstFNI, McrBC, GlaI, MvnI, HpaII (HapII), HhaI, AciI, SmaI, HinP1I, HpyCH4IV and mixtures of two or more of said enzymes.

Enrichment of DNA by Means of Triplex-Forming Molecules:

Besides proteins, according to the invention, further substances may also be used that are capable of methylation-specific binding to the DNA (e.g, triplex-forming PNA or DNA oligomers). Corresponding oligomers are described in detail, for example, in the patent application PCT/EP04/06534 (applicant: Epigenomics AG), and the literature is replete with descriptions as to how triplex-binding molecules can be used for isolating methylated DNA.

In an additional embodiment, triplex formation is used for separating methylated DNA from unmethylated DNA. The DNA is brought into contact with a triplex-forming molecule, whereupon the triplex-forming molecule preferably generates a triplex with the unmethylated DNA rather than with the methylated DNA, which is used for separation. Particularly preferred is the triple helix affinity chromatography (cf: Triplexes and biotechnology. In: Malvy, C., Harel-Bellan, A., Pritchard, L. L., eds: Triple helix-forming oligonucleotides. Kluwer Academic Publishers 1999, 285, 287f with further quotations).

In a further embodiment, the DNA may initially be randomly or non-randomly fragmented, by a suitable art-recognized method. As a random fragmentation method, the treatment with ultrasound or shearing is particularly preferred. As a non-random fragmentation method, a fragmentation with methylation-specific restriction enzymes is particularly preferred. In principle, every methylation-specific restriction enzyme may be used. Preferably, the methylation-specific restriction enzyme is selected from the group consisting of BisI, BstUI, BshI236I, AccII, BstFNI, McrBC, GlaI, MvnI, HpaII (HapII), HhaI, AciI, SmaI, HinP1I, HpyCH4IV and mixtures of two or more of said enzymes.

General:

The inventive methods will normally be used for a polynucleic acid that is a naturally occurring DNA. Preferably, a genomic DNA is used (e.g., a human genomic DNA).

In a preferred embodiment, the polynucleic acid is derived from paraffin-embedded tissue. In an alternate preferred embodiment, the polynucleic acid is derived from formalin-fixed tissue. According to particular aspects, tissues which were treated with other fixatives may also be used as a source of the polynucleic acid. In general, the polynucleic acid of any tissue which was subject to any chemical or physical treatment may be used according to the invention. In a preferred embodiment, the polynucleic acid is derived from a fresh-frozen tissue.

In a particularly preferred embodiment, inventive results obtained with methylated DNA are compared to inventive results obtained with unmethylated DNA. For this purpose, the methylated DNA and the unmethylated DNA are initially enriched using one or more of the methods described. If necessary, the DNA is labelled and amplified before the methylated DNA is brought into contact with the inventive array, and the unmethylated DNA is brought into contact with the same inventive array. Such contacting respectively occurs under conditions affording a hybridization of the methylated or unmethylated fragments with correlated immobilized nucleic acids under a defined stringency. After an optional washing step, the spatially resolved detection of such nucleic acids, to which fragments of the solution are hybridized and/or to which fragments of the solution are not hybridized, takes place. By comparison of the detected hybridizations and/or the detected non-hybridizations obtained for the originally methylated DNA with the detected hybridizations and/or the detected non-hybridizations obtained for the originally unmethylated DNA, the methylation pattern of the DNAs used can be derived. This embodiment has the advantage of a very high sensitivity.

Further, the inventive method can also be used in combination with an array, wherein the immobilized nucleic acids consist of more than 80 bases. These nucleic acids may for instance be fragments containing at least one CpG dinucleotide.

Therein, the DNA microarray will typically carry a plurality of different nucleic acids, which comprise known methylation sites. These are for instance obtainable from gene databases.

In detail, the following can be made. A first solution with fragments of a polynucleic acid, which originates from a tissue sample with diseased tissue, is prepared. A second solution with fragments of a polynucleic acid, which originates from a tissue sample of the same tissues type adjacent to the diseased tissue, however with healthy tissue, is prepared. The first solution and the second solution are simultaneously or successively contacted with the DNA microarray and then hybridized. Such immobilized nucleic acids, in particular oligonucleotides, are selected, to which exclusively the fragments of the first solution or of the second solution are hybridized or not hybridized, thereby identifying DNA fragments that comprise regulatory and/or coding regions of one or several genes. Accordingly, the respective proteins, peptides or RNAs are also derived.

Further it is possible to use the inventive oligonucleotide arrays for identifying so-called expressed CpG islands sequence tags (ECIST). For a detailed description of this method, reference is made to U.S. Ser. No. 60/118,760 and the quotations therein (incorporated by reference in its entirety). According to the invention, the hybridization of two different samples on the same DNA array is compared. The one sample was generated from genomic DNA, and the other one originates from mRNA. By hybridization with the sample originating from genomic DNA, regions of the genome that are subject to a differential methylation are determined. By means of the second sample, regions that are expressed can be determined. Since in both cases, the same DNA chip is used, a simple comparison reveals which regions of the genome are subject to such a differential methylation and are simultaneously expressed in a reciprocal differential manner.

V. Preprocessing of Signal Intensities

In particular preferred embodiments, as is familiar in the art, detected signal intensities are used directly for statistical analysis without any prior signal preprocessing. This is in particular the case: i) if only signal intensities which are derived from the same microarray-chip are compared with each other; ii) if controls distributed over the microarray-chip have the same signal intensities; and iii) or both. The controls are thereby characterized in that they have the same degree of methylation and they are distributed randomly, evenly or randomly and evenly over the entire microarray-chip.

In another preferred embodiment, different sets of controls are used, wherein each set is characterized in that: i) each control within a set has the same degree of methylation as any other control of the same set; ii) the controls of different sets differ in their degree of methylation; and iii) the controls of a set are distributed randomly, evenly or randomly and evenly.

However, it may also be favourable in certain cases to 'preprocess' detected signal intensities. Such cases can be one or a combination of the following situations: i) signal intensities are derived from different microarray-chips and are compared with each other; ii) controls, as specified above, have different signal intensities; or iii) preprocessing of signal intensities leads to more reliable and reproducible results compared to the use of signal intensities without preprocessing.

According to a particular preferred embodiment, such preprocessing comprises a "Log Transformation." "Log Transformation" as used herein, stands for applying a logarithmic function for each signal intensity value, where the base can be any positive real number other than "1." In a preferred embodiment, the logarithm to the base X is applied for each signal intensity, whereby $X \in R^+$ other than "1", preferably X is "1.3756", "2", "$\pi$", "5", "5.14", "8.2754319", "10", "50.354", or "10,000". The logarithmic function is thereby of the following formula:

$$\log_x(\text{signal intensity value})$$

$X \in R^+$ other than 1, preferably X is 1.3756, 2, $\pi$, 5, 5.14, 8.2754319, 10, 50.354, or 10,000.

In a preferred embodiment, a "Log-transformed" signal intensity value is subject to further preprocessing. In an alternate preferred embodiment, the signal intensity value was already preprocessed before a "Log Transformation" is applied to it. In a particular preferred embodiment, a "Log-transformed" signal intensity value is directly used for subsequent analysis of the methylation status.

According to a preferred embodiment, the preprocessing comprises a "Quantile Normalization". After this mathematical operation, all microarray-chips considered have the same distribution of signal intensities. Suitable methods are well known in the art, and include, but are not limited to Bolstad et al., Bioinformatics 2003 (incorporated by reference herein in its entirety). In a particular embodiment, "Quantile Normalization" is carried out as exemplified in example 23.

Preferably, values obtained from "Quantile Normalization" of signal intensity values are subject to further preprocessing. Preferably, the signal intensity values were already preprocessed before the "Quantile Normalization" is applied. Alternately, values obtained from the "Quantile Normalization" of signal intensity values are directly used for subsequent analysis of the methylation status.

Preferably, preprocessing of signal intensity values comprises a "Baseline Shift". For this operation, the arithmetic mean value of signal intensity values of controls is subtracted from each signal intensity value of the considered microarray-chip. The controls are thereby characterized in one or a combination of the following: I) only controls are considered which are located on the same microarray-chip, and subsequently the calculated arithmetic mean value is subtracted form each signal intensity value of said microarray-chip; II) the controls are distributed randomly, evenly or randomly and evenly over the microarray chip; III) all considered controls comprise the same degree of methylation; IV) all considered controls comprise the same amount of DNA; and V) the ratio of control to non-control on a microarray-chip is at least 1/5,000, preferably this ratio is in the range of 1/1,000-1/1, more preferably this ratio is in the range of 1/250-1/5, and most preferably this ratio is in the range of 1/70-1/10, in particular it is preferred that this ratio is 1/50.

In a preferred embodiment, a value obtained from the "Baseline Shift" of a signal intensity value is subject to further preprocessing. In a particular embodiment, the signal intensity value was already preprocessed before the "Baseline Shift" is applied. In an alternate embodiment, a value obtained from the "Baseline Shift" of a signal intensity value is directly used for subsequent analysis of the methylation status.

According to a preferred embodiment, the preprocessing of signal intensity values comprises the generation of a representative value for the signal intensity values of a set of immobilized nucleic acids. Said set is characterized in that all immobilized nucleic acid of a set are located in the proximity of each other in the genome. Preferably, the immobilized nucleic acids are parts of a CpG island array clone. Preferably, the immobilized nucleic acids are oligonucleotides as described above (see description of oligonucleotide chips, in particular section III and IV). The set of immobilized oligonucleotides is characterized in that the oligonucleotides of said set are comprised by the same partial sequences or DNA fragments as they are obtained according to oligonucleotide design or enrichment (see description of oligonucleotide chips, in particular section III and IV; see section I and II).

In a preferred embodiment, the representative value for the signal intensity values of a set of immobilized nucleic acids is generated by selecting the median value from the signal intensity values of the nucleic acids within a set to be analysed. According to another preferred embodiment, the representative value is generated by another art-recognized mathematical function or operation. In a preferred embodiment, the representative value is generated by calculating the arithmetic mean value. In an alternate preferred embodiment, the representative value is generated by calculating the trimmed mean value. In a further preferred embodiment, the representative value is generated by calculating the weighted mean value. In a yet another preferred embodiment, the representative value is generated by applying any linear or non-linear function or any linear or non-linear mathematical operation which is able to be generated from a plurality of value one representative value(s).

In a particular preferred embodiment, a representative value for the signal intensity values of a set of immobilized nucleic acids is subject to further preprocessing. On one aspect, the signal intensity values were already preprocessed before a representative value for the signal intensity values of a set of immobilized nucleic acids is generated. In an alternate preferred aspect, a representative value for the signal intensity values of a set of immobilized nucleic acids is directly used for subsequent analysis of the methylation status.

In a particular preferred embodiment, the signal intensity values are preprocessed as described above according to the following order:
1. "Log-Transformation"
2. "Quantile Normalization"
3. "Baseline Shift"
4. Generation of a representative value for the signal intensity values of a set of immobilized nucleic acids.

In another preferred embodiment, the signal intensity values are preprocessed as described above according to the following order:
1. "Log-Transformation"
2. "Baseline Shift"
3. Generation of a representative value for the signal intensity values of a set of immobilized nucleic acids.

In yet another preferred embodiment, the signal intensity values are preprocessed as described above according to the following order:
1. "Log-Transformation"
2. "Quantile Normalization"
3. Generation of a representative value for the signal intensity values of a set of immobilized nucleic acids.

In a further preferred embodiment, the signal intensity values are preprocessed as described above according to the following order:
1. "Log-Transformation"
2. Generation of a representative value for the signal intensity values of a set of immobilized nucleic acids.

According to a particular embodiment, a detected signal intensity is preprocessed, wherein the preprocessing comprises one or a combination of the following:
"Log-Transformation";
"Quantile Normalization";
"Baseline Shift"; and
Generation of a representative value for the signal intensity values of a set of immobilized nucleic acids.

According to one embodiment, the preprocessing is carried out in the following order:
a) "Log-Transformation";
b) "Quantile Normalization"
c) "Baseline Shift"; and
d) Generation of a representative value for the signal intensity values of a set of immobilized nucleic acids.

According to an alternate embodiment, the preprocessing is carried out in the following order:
a) "Log-Transformation";
b) "Baseline Shift"; and
c) Generation of a representative value for the signal intensity values of a set of immobilized nucleic acids.

According to an additional preferred embodiment, the preprocessing is carried out in the following order:
a) "Log-Transformation";
b) "Quantile Normalization"; and
c) Generation of a representative value for the signal intensity values of a set of immobilized nucleic acids.

According to yet another preferred embodiment, the preprocessing is carried out in the following order:
a) "Log-Transformation";
b) Generation of a representative value for the signal intensity values of a set of immobilized nucleic acids.

Yet further embodiments comprise preprocessing of signal intensity values that takes into account other controls like nucleic acids encoding repeats or random sequences.

VI. Analysis of Copy-Number Changes

A preferred embodiment of the invention comprises:
deriving DNA from a test sample and/or a reference sample;
optionally, enriching DNA from the derived DNA, preferably methylated and/or unmethylated DNA is enriched;
labelling enriched DNA of the test sample and/or the reference sample identically or differentially with one or more physically detectable substances;
hybridizing labeled DNA on one or more DNA arrays, preferably on one or more arrays as described in one or more embodiments of the invention;
optionally, performing a washing step; and
performing a spacially resolved detection of signal intensities of those nucleic acids, to which fragments are hybridized and/or to which fragments are not hybridized;
comparing of the detected signal intensities of hybridizations and/or of non-hybridizations for DNA derived from a test sample and for DNA derived from a reference sample, wherein the percentage of methylation and/or the copy-number for said DNA is deduced.

In a preferred embodiment, an analysis of copy-number changes is carried out by means of comparative genomic hybridization (CGH) analysis. Therefore one or more oligonucleotide arrays according to the invention and/or DNA enrichment methods according to the invention are used. The methylation pattern and the copy-number of DNA in a genome are hereby analysed simultaneously.

For CGH analysis, DNA fragments derived from genomic DNA isolated from test and reference samples are labeled and hybridized to a DNA-microarray, in particular an oligonucleotide microarray according to the invention as described above (see section III and IV). Of course more than two genomes or samples can be compared simultaneously if distinguishable labels are used.

According to the invention, hybridization can be performed in different ways. In a particularly preferred embodiment, identical arrays are used, on each array only DNA fragments derived from genomic DNA of a single sample are hybridized.

In another particularly preferred embodiment, each sample of DNA fragments obtained from genomic DNA of different samples is labeled differentially. Thus the differentially labeled DNA can be applied to the same array. Moreover, it is preferred that only some of DNA fragment samples are labeled differentially and hybridized to the same array. DNA fragments derived from other samples and labeled with the same labels are hybridized on a different array.

In a further particularly preferred embodiment, DNA fragments derived from one or more test samples are hybridized each to different identical or all to the same array. The data resulting from these hybridizations is then compared with data obtained previously for DNA fragments of a reference sample.

According to the invention, it is preferred that the complexity of genomic DNA is reduced. This is in particular preferred if an oligonucleotide array is used. The reduction of complexity has the advantage that the signal-to-noise ratio is increased. Therefore the CGH analysis is characterized by a high reliability and reproducibility also if only small amount of genomic DNA as starting material are available. Because of the same reason, the reduction of complexity also allows the use of low complexity array elements if desired.

Oligonucleotide Array:

In a preferred embodiment one or more oligonucleotide arrays according to the invention are used for CGH analysis as described above (see section III and IV). According to this embodiment, DNA fragments are generated according to standard CGH protocols as they are known to those skilled in the art. For example DNA fragments are made by cleaving genomic DNA with a restriction endonuclease, ligating the cleaved products to template oligonucleotides, and then performing a polymerase chain reaction (PCR) amplification using complementary oligonucleotides in which preferential DNA fragments smaller than 1 kb are amplified. The restriction endonuclease can be for example DpnII or BglII which will result in a complexity reduction of 70% and 2.5%, respectively (Lucito et al. *Genome Research,* 10: 1726-1736, 2000).

According to this embodiment, variation of the DNA copy-number but not alteration in the methylation pattern in a genome are detectable. The intensity of the hybridization signal obtained for DNA fragments of test and reference samples at a given location is proportional only to the relative copy-number of those sequences in the test and the reference genome. Typically the reference genome is regarded as normal. Increases and decreases in the intensity of the hybridization signal relative to that of the reference sample indicate only variations of the DNA copy-number in the genome of the test sample.

The use of an oligonucleotide array according to the invention for CGH analysis has the advantage that variations of the DNA copy-number are selectively analysed for genomic regions comprising genes or regulatory regions. As well known in the art, the sites for methylation, the CpG dinucleotides, are mainly associated with genes or regions of regulatory function. Secondly, the fragments of the oligonucleotide array hybridize specifically to CpG dense DNA fragments contained in the complexity reduced representation of the genome. Because of that, this embodiment is of particular interest for high resolution gene-by-gene mapping of copy number changes, or for direct combination of data of copy-number changes with methylation changes. Furthermore, the use of an oligonucleotide array according to the invention for CGH analysis is advantageous because the oligonucleotide array according to the invention is characterized i) by a high resolution, and ii) by a increased signal-to-noise ratio because no oligonucleotide comprises more than 50%, preferentially more then 20% repeats.

In a preferred embodiment, the one or more oligonucleotide arrays for CGH analysis are so called tiling arrays. As described above the oligonucleotides of such a tiling array are characterized in that they hybridize exclusively in constant to each other defined distances on the complementary DNA for analysis. The advantage of the use of such tiling arrays for CGH analysis is that it is possible to determine directly the approximate length of the region with variations in copy-number and that the whole genome of interest can be analysed. In another preferred embodiment, the one or more oligonucleotide arrays used for CGH analysis are oligonucleotide arrays according to the invention and they are so-called tiling arrays. This means there are only oligonucleotides able to hybridize exclusively in constant to each other defined distances on the fragments of the CpG-islands, specifically to CpG dense DNA fragments contained in the complexity reduced representation of the genome. The use of such tilling arrays for CGH analysis has the advantage that it is possible to determine directly the approximate length of the region with variations in copy-number and that the only regions of the genome of interest are analysed which are either genes or correspond to them.

Complexity Reduction by Enrichment of Methylated and/or Unmethylated DNA:

In a preferred embodiment, CGH analysis is performed by using known arrays and complexity reduced DNA, wherein the complexity reduction is achieved by enrichment of methylated or unmethylated DNA. The Array can be any array suitable for CGH analysis. In particular this array is an oligonucleotide array or a DNA array carrying any type of nucleic acid (DNA, RNA or PNA) with various lengths. The enrichment of methylated or unmethylated DNA can be done as described above by restrictions enzymes, by bringing the DNA into contact with substances specifically binding methylated or unmethylated DNA, or by combinations thereof (see section I, II, III and IV).

According to this embodiment, the corresponding hybridization signals represent a mixture of copy-number changes and methylation changes. It is not possible to interpret the signal intensities in a way that enables a deduction of the copy-number changes and/or the methylation changes. Therefore, in another embodiment, it is preferred that the DNA derived from a sample is completely methylated or unmethylated. Suitable methods are known to those skilled in the art. A treatment to generate completely methylated DNA can be any kind of treatment, preferably a treatment with a methyltransferase, in particular a treatment with the methyltransferase SssI. The treatment can take place before or in between the enrichment where appropriate. A treatment to generate completely unmethylated DNA can be any kind of chemical or enzymatic treatment, in particular the genomic DNA is subject to amplification as well known to those skilled in the art. Such an amplification is preferably carried out according to whole genome amplification methods as described above (see section IV "Labeling"). Most preferably, the isothermal "Multiple Displacement Amplification" (MDA) is used. The DNA is reacted with random primers and a DNA polymerase. The polymerase is capable to displace the non-template strand of the DNA double strand during the amplification (e.g. a φ29 polymerase). The displaced strands serve as a matrix for the extension of further primers.

According to this embodiment, variation of the DNA copy-number, but not alteration in the methylation pattern in a genome is detectable. The intensity of the hybridization signal obtained for DNA fragments of test and reference samples at a given location is proportional only to the relative copy-number of those sequences in the test and the reference genome. Typically the reference sample is regarded as normal. Increases and decreases in the intensity of the hybridization signal relative to that of the reference sample indicate only variations of the DNA copy-number in the genome of the test sample.

Furthermore, this embodiment has also the advantage that variations of the DNA copy-number are selectively analysed for genomic regions comprising genes and regulatory regions. The reason for this is that the complexity of the DNA is reduced by enrichment of unmethylated or methylated DNA or by restriction of one or more non-methylation-specific restriction enzyme and subsequent linker mediated amplification as described below in detail. As is well known in the art, CpG dinucleotides (the site for cytosine methylation) are mainly associated with genes or regulatory regions. Therefore, this embodiment is also of particular interest for high resolution gene-by-ene mapping of copy-number changes, or for direct combination of data of copy-number changes with methylation changes.

According to particular aspects of the invention, the enrichment can be carried out as described as follows:

Method I:

In a particularly preferred embodiment, unmethylated or methylated DNA is enriched by restriction enzyme treatment according to method I. In brief, the enrichment occurs by digestion of the DNA with at least one methylation-specific restriction enzyme without previous addition of a non-methylation-specific restriction enzyme. For example, the following steps are provided:

a) a solution comprising the polynucleic acid is prepared;

b) optionally, a processing step is performed, in which substances that are not polynucleic acids, are depleted, and/or the polynucleic acid is enriched/accumulated;

c) a methylation-specific restriction enzyme or several methylation-specific restriction enzymes are added to the solution without previous addition of a non-methylation-specific restriction enzyme, wherein the polynucleic acid is cut to fragments at restriction sites, which are capable of being methylated, but are not methylated, and d) the fragments obtained in step c) are subjected to an amplification step.

In preferred embodiments, the amplification is carried out by ligation of adapters to the fragments after the restriction. Thereafter, the fragmented DNA is amplified, wherein simultaneous labeling of the fragments with a detectable substance can be achieved.

Optionally, before amplification, fragments after adapter ligation are subject to a digestion with the same restriction enzyme or enzymes as used in step c). This has the advantage that any religated fragments are digested while fragment-adapter ligations remain unaffected.

As methylation-specific restriction enzyme, any enzymes may be used that only cut if their recognition sequence is unmethylated. A person of ordinary skill in the art is will have knowledge of suitable restriction enzymes. Examples of such enzymes are: BstUI, BshI236I, AccII, BstFNI, MvnI, HpaII (HapII), HhaI, AciI, SmaI, HinP1I, HpyCH4IV or mixtures of said enzymes. According to the invention, restriction enzymes may also be used that only cut if a methylated recognition sequence exists. A person of ordinary skill in the art will know of such suitable restriction enzymes (e.g., McrBC enzyme (New England Biolabs) and the recently identified BisI enzyme (SibEnzyme Ltd., Russia, www-.science.sibenzyme.com/article8_article_7_1.phtml) and the GlaI enzyme (SibEnzyme Ltd., Russia, www.science.sibenzyme.com/article8_article_11_1.phtml) are mentioned). Additionally, combinations of said enzymes are applicable. The use of further enzymes not yet identified is within the scope of the present invention, insofar as the enzymes cut methylation-specifically methylated or unmethylated recognition sequences.

According to this embodiment, fragments having a length in the range from 50 bases to 5,000 bases, preferably from 50 to 2,000 bases, most preferably from 50 to 1,000 bases, and in particular from 50 to 600 bases are selectively enriched.

Accordingly, a reduction of the complexity by a factor greater than 100 is achievable in the specified length window. This is also based on the fact that methylated sequence regions (or in the alternative case, unmethylated sequence regions) and sequence regions without recognition sequences of the used methylation-specific restriction enzymes are not cut and consequently form fragments, the length of which is as a rule above the upper limits of the amplification window. In contrast thereto, regions with unmethylated recognition sites (restriction enzyme which cuts only an unmethylated recognition sequence) are cut and form fragments having a length below the upper limit of the amplification window. Of course, the equivalent will happen in the case of restriction enzymes, which cut only, if their recognition sequences are methylated. Further, and significantly, no potentially interesting fragments are cut non-methylation-specifically, and thereby are reduced to a length below the lower limit of the window. Consequently, all interesting fragments, i.e. those with potentially hypermethylated or hypomethylated sites, are available for the following analyses. Finally, the full process is simplified, since fewer restriction enzymes are used. It is even possible to perform all reactions up to the hybridization on a array in one vessel (one tube process). Consequently, processing is simplified and considerably faster. Finally, the number of potential error sources in the process is substantially reduced.

Method II:

In a particularly preferred embodiment, unmethylated or methylated DNA is enriched by restriction enzyme treatment according to method II. The enrichment of methylated or unmethylated fragments occurs by digestion with non-methylation-specific restriction enzymes and after ligation of adapters to the fragments, if applicable with methylation-specific enzymes. For instance, the following steps may be provided:

a) a solution comprising the polynucleic acid is prepared;

b) optionally, a processing step is performed, in which substances that are not polynucleic acids, are depleted, and/or the polynucleic acid is enriched;

c) one or preferably at least two different non-methylation-specific restriction enzymes are added to the solution, wherein the polynucleic acid is cut at cutting sites being specific for the restriction enzymes;

d) the solution obtained in step c) is purified while separating small fragments;

e) linkers are ligated to the fragments obtained in step d);

f) then one or preferably at least two methylation-specific restriction enzymes are added to the solution obtained in step e), the fragments obtained in step d) being cut at cutting sites, which are capable of being methylated, but are not methylated, or the fragments obtained in step d) being cut at restriction sites, which are capable of being methylated and are actually methylated; and g) the fragments obtained in step f) are subjected to an amplification step after an optional further purification step, wherein only those fragments not cut in step f) are amplified.

In a preferred embodiment, in step d) of the above method, fragments having a length of less than 40 bp, preferably less than 70 bp, and more preferably less than 100 bp are separated from the solution obtained in step c).

In a preferred embodiment, the amplification in step g) takes place by means of primer molecules, which hybridize to the linkers introduced in step e) and of a polymerase under suitable PCR conditions.

Accordingly, preferably fragments having a length in the range of 50 bases to 5,000 bases, preferably in the range of 70 to 2,000 bases, and in more preferably in the range of 100 to 1,200 bases are selectively enriched.

It is preferred that in step c) three different non-methylation-specific restriction enzymes are added.

It is further preferred that at least one, preferably all non-methylation-specific restriction enzymes cut recognition sequences having a length of four bases, in particular recognition sequences, which do not contain CG. By using restriction enzymes with recognition sequences having a length of four bases, the generation of fragments being short and thus separable by purification is increased, which reduces the complexity. Simultaneously, by using restriction enzymes with recognition sequences having a length of four bases, the number of potentially interesting fragments (i.e. fragments, which possibly comprise CpG islands or fragments with a density of CG dinucleotides with an amplifiable size being increased compared to the average in the genome) is increased.

Advantageously, at least one, preferably all non-methylation-specific restriction enzymes generate sticky ends, in particular sticky ends with an overhang containing TA. Particularly preferred is the use of non-methylation-specific restriction enzymes, which cut a recognition sequence of four bases to sticky ends, and all restriction enzymes produce the same overhangs. Alternately, one or several non-methylation-specific restriction enzymes that produce sticky ends are used in conjunction with one or several non-methylation-specific restriction enzymes that produce blunt ends, since a ligation of a fragment with a sticky end with a fragment with a blunt end is also possible. Of course it is also possible to use only non-methylation-specific restriction enzymes, which produce blunt ends, since in this case, too, a ligation is possible. The non-methylation-specific restriction enzymes are preferably selected from at least two, preferably three from of the group consisting of MseI, BfaI, Csp6I, Tru1I, Tvu1I, Tru9I, Tvu9I, MaeI and XspI. Particularly preferred is the use of a combination of MseI, Bfa1 and Csp6. In principle, step c) may be performed with common (i.e. simultaneous) addition of all non-methylation-specific restriction enzymes to the solution. Alternatively, the restriction enzymes can be added sequentially to the solution during step c). In principle, every methylation-specific restriction enzyme can be used. Preferably, the methylation-specific restriction enzyme is an enzyme which cuts its recognition site only if it is unmethylated. Suitable enzymes are known to those skilled in the art, also so far unknown suitable restriction enzymes are useable. In a preferred embodiment the methylation-specific restriction enzyme is selected from the group consisting of BisI, BstUI, BshI236I, AccII, BstFNI, McrBC, MvnI, HpaII (HapII), GlaI, HhaI, AciI, SmaI, HinP1I, HpyCH4IV, and mixtures of two or more of the above enzymes. Preferred is a mixture containing the restriction enzymes BstUI, HpaII, HpyCH4IV and HinP1I. In another preferred embodiment, the methylation-specific restriction enzyme is an enzyme which cuts its recognition site only if it is methylated. Suitable enzymes are known to those skilled in the art, and other suitable enzyme will no doubt be discovered or engineered in the future. In a preferred embodiment, the methylation-specific restriction enzyme is selected from the group consisting of BisI, McrBC, GlaI, and combinations of two or more thereof. A person a ordinary skill in the art will know how to adjust following described embodiments for comparative genomic hybridisation.

Combination of CpG-Island Array and of Complexity Reduction by Enrichment of Methylated and/or Unmethylated DNA:

In a preferred embodiment, CGH analysis is performed by using CpG-island-arrays in combination with complexity reduced DNA, wherein the complexity reduction is achieved by enrichment of methylated or unmethylated DNA. The enrichment of methylated or unmethylated DNA can be done as described above by restriction enzymes, by bringing the DNA into contact with substances specifically binding methylated or unmethylated DNA, or by combinations thereof (see section I, II, III and IV).

This embodiment has the advantage that changes in the methylation pattern and variations in the DNA copy-number can be simultaneously detected. According to the invention, the intensity of the hybridization signal obtained for DNA fragments of test and reference samples at a given location is proportional not only to the state of methylation but also to the relative copy-number of those sequences in the DNA of the test and the reference sample. Typically the DNA of the reference sample is regarded as normal. Increases and decreases in the intensity of the hybridization signal of the test sample relative to that of the reference sample indicate alteration of the methylation of the analyzed CpG positions and/or of the DNA copy-number in the genome of the test sample.

Moreover, this embodiment has the advantage that variations of the DNA copy-number are selectively analysed for genomic regions comprising genes or regulatory regions. This is based on the following: First, the complexity of the DNA is reduced by enrichment of unmethylated or methylated DNA or by restriction of one or more non-methylation-specific restriction enzyme and subsequent linker mediated amplification as described above in detail. As well known in the art, CpG dinucleotides (the site for cytosine methylation) are mainly associated with genes or regulatory regions. Second, the fragments of the CpG-island array hybridize specifically to CpG dense DNA fragments contained in the complexity reduced representation of the genome as produced by the embodiments of the invention. As is well known in the art, the sites for methylation (CpG dinucleotides) are primarily associated with genes or regulatory regions. Because of that, this embodiment is of interest for high resolution gene by gene mapping of copy number changes, or for direct combination of data of copy-number changes with methylation changes.

As described below, three major embodiments (embodiments I, II and III) are in particular preferred.

Combination of Oligonucleotide Array and of Complexity Reduction by Enrichment of Methylated and/or Unmethylated DNA:

In a particular preferred embodiment, CGH analysis is carried out by means of combining oligonucleotide arrays according to the invention (see section III and IV) and DNA enrichment methods according to the invention (see section I, II, III and IV). This embodiment has the advantage that changes in the methylation pattern and variations in the DNA copy-number can be simultaneously detected. According to this aspect, the intensity of the hybridization signal obtained for DNA fragments of test and reference samples at a given location is proportional not only to the state of methylation but also to the relative copy-number of those sequences in the test and the reference genome. Typically the reference genome is regarded as normal. Increases and decreases in the intensity of the hybridization signal of the test sample relative to that of the reference sample indicate alteration of the methylation of the analyzed CpG positions and/or of the DNA copy-number in the genome of the test sample.

According to the invention the following three major embodiments (embodiments I, II and III) are in particular preferred:

Embodiment I

A preferred embodiment comprises:
generating two types of samples of DNA fragments. each derived from a test sample and/or a reference sample;
generating the first type of sample comprising a complexity reduction of genomic DNA independent of the methylation pattern of the genomic DNA;
generating the second type of sample comprising a first methylation-non-specific restriction enzyme digestion and a second methylation-specific restriction enzyme digestion;
deducing copy-number variations by comparison of detected signal intensities of the first type of DNA fragment samples of a test sample with the detected signal intensities of the first type of DNA fragment samples of a reference sample; and
deducing methylation changes by comparison of detected signal intensities of the second type of DNA fragment samples of a test sample with the detected signal intensities of the second type of DNA fragment samples of a reference sample.

Another preferred embodiment comprises a comparison of signal intensities derived from the first type of DNA fragment samples, wherein:
the same signal intensity for a test sample and for a reference sample indicate that the genomic region in the test sample corresponding to the hybridized DNA fragments is present in the same copy-number as the corresponding genomic region in the reference sample;
an increased signal intensity for a test sample in comparison to the signal intensity for a reference sample indicates that the genomic region in the test sample corresponding to the hybridized DNA fragments is present at a higher copy-number than the corresponding genomic region in the reference sample, wherein the increase of the copy-number is thereby proportional to the signal increase;
a decreased signal intensity for a test sample in comparison to the signal intensity for a reference sample indicates that the genomic region in the test sample corresponding to the hybridized DNA fragments is present at a lower copy-number than the corresponding genomic region in the reference sample, wherein the decrease of the copy-number is thereby proportional to the signal decrease.

A further preferred embodiment comprises a comparison of signal intensities derived from the second type of DNA fragment samples, wherein:
the same signal intensity for a test sample and for a reference sample indicates that the same degree of analyzed cytosines of the test sample is methylated as in the reference sample;
an increased signal intensity for a test sample in comparison to the signal intensity for a reference sample indicates that a higher degree of the analyzed cytosines in the test sample is methylated than in the reference sample, wherein the increase in methylation is thereby proportional to the signal increase; and
a decreased signal intensity for a test sample in comparison to the signal intensity for a reference sample indicates that a lower degree of the analyzed cytosines of the test sample is methylated than in the reference sample, wherein the decrease in methylation is thereby proportional to the signal decrease.

According to embodiment I, two types of samples of DNA fragments are generated each from genomic DNA of test and of reference samples. The first type of sample (herein referred as type A) is generated by enrichment of DNA fragments independent of the methylation pattern of the genomic DNA. In a first embodiment, type-A DNA fragments are generated by enrichment according to the above-described method II, wherein genomic DNA is digested with non-methylation-specific restriction enzymes, linkers are ligated to the resulting fragments, and fragments with linkers are amplified by linker mediated PCR.

According to a second embodiment, type-A DNA fragments are generated by treatment of DNA so that all cytosines of CpG dinucleotides are methylated and by enrichment of methylated DNA fragments. Accordingly, the enrichment is carried out according to the above-described method II, wherein genomic DNA is digested with non-methylation-specific restriction enzymes, linkers are ligated to the resulting fragments, linker-ligated fragments are digested with methylation-specific restriction enzymes, and fragments with linkers are amplified by linker mediated PCR. The treatment which results in a complete methylation of cytosines of CpG dinucleotides can be any kind of treatment, preferably a treatment with a methyltransferase, in particular a treatment with the methyltransferase SssI. The treatment can take place before or in between the enrichment, in particular before any digestion of genomic DNA with non-methylation-specific restriction enzymes, or before linkers are ligated to the resulting fragments, or before all fragments are subjected to a methylation-specific restriction enzyme digestion.

According to a third embodiment, type-A DNA fragments are generated by treatment of DNA so that all cytosines of CpG dinucleotides are not methylated and by enrichment of unmethylated DNA fragment. Accordingly, the enrichment is carried out according to the above-described method II, wherein genomic DNA is digested with non-methylation-specific restriction enzymes, linkers are ligated to the resulting fragments, linker-ligated fragments are digested with methylation-specific restriction enzymes, and fragments with linkers are amplified by linker mediated PCR. The treatment which results in a complete unmethylation of cytosines of CpG dinucleotides can be any kind of chemical or enzymatic treatment, in particular the genomic DNA is subject to amplification as well known to those skilled in the art. Such an amplification is preferably carried out according to whole genome amplification methods as described above (see section IV, "Labeling"). Most preferably the isothermal "Multiple Displacement Amplification" (MDA) is used. The DNA is reacted with random primers and a DNA polymerase. The polymerase is capable of displacing the non-template strand of the DNA double strand during the amplification (e.g., a $\phi$29 polymerase). The displaced strands serve as a matrix for the extension of further primers. The treatment can take place before or in between the enrichment, in particular before any digestion of genomic DNA with non-methylation-specific restriction enzymes, or before linkers are ligated to the resulting fragments, or before all fragments are subjected to a methylation-specific restriction enzyme digestion.

According to each embodiment of the generation of type-A fragments, the second type of sample (herein referred as type B) is generated by complexity reduction of genomic DNA by a first methylation non-specific restriction enzyme digestion and a second methylation specific restriction enzyme digestion. In particular, the enrichment of DNA fragments is carried out according to the above described method II, wherein genomic DNA is digested with non-methylation-specific restriction enzymes, linkers are ligated to the resulting fragments, all fragments are subjected to a methylation-specific restriction enzyme digestion, and undigested fragments with linkers on both ends are amplified by linker mediated PCR.

Such generated DNA fragments derived from test and reference sample are then subjected to one or more CpG-island-arrays and/or to one or more oligonucleotide arrays according to the invention as described above. If samples of DNA fragments are subject to the same array, the DNA fragments have to be labeled differentially. If the samples of DNA fragments are subject to different identical arrays, the DNA fragments may have the same label or different ones.

After hybridization of the respective DNA fragments on the complementary oligonucleotides or nucleic acids of the corresponding arrays, one or more hybridization signals are detectable, and conclusions are drawn from the intensity of these signals with respect to variations in DNA copy-number, and to changes in the methylation pattern, or both.

Copy-number variations are deduced from signals derived from type A DNA fragment samples of test samples in comparison to those signals derived from type A DNA fragment samples of reference samples.

I) If the signal for a test sample has the same intensity as the signal of the corresponding reference sample, then the genomic DNA region in the genomic DNA of the test sample is present in the same copy-number as in the genome of the reference sample.

II) If the signal for a test sample has an increased intensity in comparison to the signal of the corresponding reference sample, then the genomic DNA region in the genomic DNA of the test sample is present at higher copy-numbers then in the genomic DNA of the reference sample. The amplification of the copy-number is thereby proportional to the increase of the hybridization signal of the test sample relative to that of the reference sample.

III) If the signal for a test sample has a decreased intensity in comparison to the signal of the corresponding reference sample, then the genomic DNA region in the genomic DNA of the test sample is absent or present at lower copy-numbers then in the genomic DNA of the reference sample. The reduction of copy-number is thereby proportional to the decrease of the hybridization signal of the test sample relative to that of the reference sample.

Thereby, in each of the above three cases I-III, the genomic DNA region is characterized in that it comprises at least parts of the complementary sequence of the oligonucleotide or nucleic acid to which the respective DNA fragment is hybridized.

Changes in the methylation pattern are deduced from signals derived from type B DNA fragment samples of the test sample in comparison to those signals derived from type B DNA fragment samples of the corresponding reference sample.

I) If the signal for a test sample has the same intensity as the signal of the corresponding reference sample, then the region of the genomic DNA of the test sample corresponding to the hybridized DNA fragment comprises the same ratio of methylated to unmethylated cytosines in a CpG context as the corresponding region of the genomic DNA of the reference sample.

II) If the signal for a test sample has an increased intensity in comparison to the signal of the corresponding reference sample, then the region of the genomic DNA of the test sample corresponding to the hybridized DNA fragment comprises an increased ratio of methylated to unmethylated cytosines in a CpG context compared to the corresponding region of the genomic DNA of the reference sample. The increase in the ratio is thereby proportional to the increase of the hybridization signal of the test sample relative to that of the reference sample.

III) If the signal for a test sample has an decreased intensity in comparison to the signal of the corresponding reference sample, then the region of the genomic DNA of the test sample corresponding to the hybridized DNA fragment comprises a decreased ratio of methylated to unmethylated cytosines in a CpG context compared to the corresponding region of the genomic DNA of the reference sample. The decrease in the ratio is thereby proportional to the decrease of the hybridization signal of the test sample relative to that of the reference sample.

Thereby, in each of the above three cases I-III, the genomic DNA region is characterized in that it comprises at least parts of the complementary sequence of the oligonucleotide or nucleic acid to which the respective DNA fragment is hybridized.

Embodiment II

A preferred embodiment comprises:
generating two types of samples of DNA fragments each derived from a test sample and/or a reference sample;
generating the first type of sample comprising a first methylation-non-specific restriction enzyme digestion and a second methylation-specific restriction enzyme digestion;
generating the second type of sample comprising a methylation-specific restriction enzyme digestion;
deducing an alteration in DNA methylation by comparison of signal intensities of hybridizations or non-hybridizations derived form the first type of DNA fragments of the test sample with those derived from the reference sample, or by comparison of signal intensities of hybridizations or non-hybridizations derived from the second type of DNA fragments of a test sample with those derived from a reference sample, or both; and
deducing a copy-number variation by considering a comparison of signal intensity of hybridizations or non-hybridizations derived from the first type DNA fragments of a test sample with those derived from a reference sample and a comparison of signal intensity of hybridizations or non-hybridizations derived from the second type DNA fragments of a test samples with those derived from a reference sample.

Another preferred embodiment comprises a comparison of signal intensities derived from the first type of DNA fragments of a test sample with those derived from a reference sample, wherein:
the same signal intensity for a test sample and for a reference sample indicates that the genomic region of the test sample corresponding to the hybridized DNA fragments comprises the same ratio of methylated to unmethylated cytosines as the corresponding genomic region of the reference sample;
an increased signal intensity for a test sample in comparison to a reference sample indicates that the genomic region of the test sample corresponding to the hybridized DNA fragments comprises an increased ratio of methylated to unmethylated cytosines compared to the corresponding genomic region of the reference sample, wherein the ratio increase is thereby proportional to the signal increase; and
a decreased signal intensity for a test sample in comparison to a reference sample indicates that the genomic region of the test sample corresponding to the hybridized DNA fragments comprises a decrease ratio of methylated to unmethylated cytosines compared to the corresponding genomic region of the reference sample, wherein the ratio decrease is thereby proportional to the signal decrease.

A further preferred embodiment comprises a comparison of signal intensities derived from the second type of DNA fragments of a test sample with those derived from a reference sample, wherein:
the same signal intensity for a test sample and for a reference sample indicates that the genomic region of the test sample corresponding to the hybridized DNA fragments comprises the same ratio of unmethylated to methylated cytosines as the corresponding genomic region of the reference sample;
an increased signal intensity for a test sample in comparison to a reference sample indicates that the genomic region of the test sample corresponding to the hybridized DNA fragments comprises an increased ratio of unmethylated to methylated cytosines compared to the corresponding genomic region of the reference sample, wherein the ratio increase is thereby proportional to the signal increase; and
a decreased signal intensity for a test sample in comparison to a reference sample indicates that the genomic region of the test sample corresponding to the hybridized DNA fragments comprises a decrease ratio of unmethylated to methylated cytosines compared to the corresponding genomic region of the reference sample, wherein the ratio decrease is thereby proportional to the signal decrease.

Another preferred embodiment comprises a comparison of signal intensities derived from the first type DNA fragments of a test sample with those derived from a reference sample and a comparison of signal intensities derived from second type DNA fragments of a test sample with those derived from a reference sample, wherein:
a deletion of a genomic DNA region is indicated by a decreased signal intensity of first type DNA fragments of a test sample in comparison to that of a reference sample and a decreased signal intensity of second type DNA fragments of a test sample in comparison to that of a reference sample;
an amplification of a genomic DNA region is indicated by:
i) an increased signal intensity of DNA fragments of a test sample in comparison to those of a completely methylated reference sample in case of enrichment of methylated DNA;
ii) an increased signal intensity of DNA fragments of a test sample in comparison to those of a completely unmethylated reference sample in case of enrichment of unmethylated DNA;
iii) an increased signal intensity of DNA fragments of a completely methylated test sample in comparison to those of a completely methylated reference sample in case of enrichment of methylated DNA, or
iv) an increased signal intensity of DNA fragments of a completely unmethylated test sample in comparison to those of a completely unmethylated reference sample in case of enrichment of unmethylated DNA.

According to embodiment II, two types of samples of DNA fragments are generated each from genomic DNA of test and of reference samples. The first type of sample (herein referred as type-B) is generated by a first methylation-non-specific restriction enzyme digestion and a second methylation-specific restriction enzmye digestion. In particular, type-B DNA fragments are generated according to the above described method II, wherein genomic DNA is digested with non-methylation-specific restriction enzymes, linkers are ligated to the resulting fragments, all fragments are subjected to a methylation-specific restriction enzyme digestion, and undigested fragments with linkers on both ends are amplified by linker mediated PCR. The second type of sample (herein referred to as type C) is generated by a methylation-specific restriction enzyme digestion. In particular, type C DNA fragments are generated according to the above described method I, wherein genomic DNA is digested with methylation-specific restriction enzymes, linkers are ligated to the resulting fragments, and fragments with linkers are amplified by linker-mediated PCR.

Such generated DNA fragments derived from test and reference samples are then subjected to one or more CpG-island-arrays and/or to one or more oligonucleotide arrays according to the invention as described above. If samples of DNA fragments are subject to the same array, the DNA fragments have to be labeled differentially. If the samples of DNA fragments are subject to different identical arrays, the DNA fragments may have the same label or different ones.

After hybridization of the respective DNA fragments on the complementary oligonucleotides or nucleic acids of the corresponding arrays, one or more hybridization signals are detectable. According to the invention, conclusions are drawn from the intensity of these signals with respect to the variations in the DNA copy-number, and to changes in the methylation pattern, or both.

Changes in the methylation pattern are deduced from signals derived from type-B DNA fragment samples of the test sample in comparison to those signals derived from type-B DNA fragment samples of the corresponding reference sample.

I) If the signal for a test sample has the same intensity as the signal of the corresponding reference sample, then the region of the genomic DNA of the test sample corresponding to the hybridized DNA fragment comprises the same ratio of methylated to unmethylated cytosines in a CpG context as the corresponding region of the genomic DNA of the reference sample.

II) If the signal for a test sample has an increased intensity in comparison to the signal of the corresponding reference sample, then the region of the genomic DNA of the test sample corresponding to the hybridized DNA fragment comprises an increased ratio of methylated to unmethylated cytosines in a CpG context compared to the corresponding region of the genomic DNA of the reference sample. The increase in the amount of methylated cytosines is thereby proportional to the increase of the hybridization signal of the test sample relative to that of the reference sample.

III) If the signal for a test sample has a decreased intensity in comparison to the signal of the corresponding reference sample, then the region of the genomic DNA of the test sample corresponding to the hybridized DNA fragment comprises a decreased ratio of methylated to unmethylated cytosines in a CpG context compared to the corresponding region of the genomic DNA of the reference sample. The decrease in the amount of methylated cytosines is thereby proportional to the decrease of the hybridization signal of the test sample relative to that of the reference sample. Thereby, in each of the three cases I-III, the genomic DNA region is characterized in that it comprises at least parts of the complementary sequence of the oligonucleotide or nucleic acid to which the respective DNA fragment is hybridized.

Alternatively, changes in the methylation pattern can also be deduced from signals derived from type-C DNA fragment samples of the test sample in comparison to those signals derived from type-C DNA fragment samples of the corresponding reference sample:

I) If the signal for a test sample has the same intensity as the signal of the corresponding reference sample, then the region of the genomic DNA of the test sample corresponding to the hybridized DNA fragment comprises the same ratio of unmethylated to methylated cytosines in a CpG context as the corresponding region of the genomic DNA of the reference sample.

II) If the signal for a test sample has an increased intensity in comparison to the signal of the corresponding reference sample, then the region of the genomic DNA of the test sample corresponding to the hybridized DNA fragment comprises a increased ratio of unmethylated to methylated cytosines in a CpG context compared to the corresponding region of the genomic DNA of the reference sample. The increase in the ratio is thereby proportional to the increase of the hybridization signal of the test sample relative to that of the reference sample.

III) If the signal for a test sample has a decreased intensity in comparison to the signal of the corresponding reference sample, then the region of the genomic DNA of the test sample corresponding to the hybridized DNA fragment comprises a decreased ratio of unmethylated to methylated cytosines in a CpG context compared to the corresponding region of the genomic DNA of the reference sample. The decrease in the ratio is thereby proportional to the decrease of the hybridization signal of the test sample relative to that of the reference sample.

Thereby, in each of the three cases I-III, the genomic DNA region is characterized in that it comprises at least parts of the complementary sequence of the oligonucleotide or nucleic acid to which the respective DNA fragment is hybridized.

Of course, the methylation pattern can also be deduced by taking into account the above said for both type-B and type-C DNA fragments.

Copy-number variations are deduced by taking into account signals derived from type-B DNA fragment samples of the test sample in comparison to those signals derived from type-B DNA fragment samples of the corresponding reference sample and signals derived from type C-DNA fragment samples of the test samples in comparison to those signals derived from type-C DNA fragment samples of the corresponding reference sample.

A deletion of a genomic DNA region is present in the genome of a test sample, if the following two cases apply simultaneously to the same or to different identical oligonucleotides or nucleic acids on arrays: 1) The signal of type-B DNA fragments for a test sample has a decreased intensity in comparison to the signal of the corresponding reference sample, and 2) the signal of type-C DNA fragments for a test sample has a decreased intensity in comparison to the signal of the corresponding reference sample.

The amplification of a genomic region can be determined according to the following: First, only the reference sample is 'treated' for the determination of an amplification, depending on the type of enrichment. In case of the enrichment of methylated DNA, an aliquot of a reference sample is treated appropriately so that all cytosines of CpG dinucleotides are methylated (100% methylated reference sample). Such a treatment can be any kind of treatment, preferably a treatment with a methyltransferase, in particular a treatment with the methyltransferase SssI. The treatment can take place before or in between the enrichment according to method II, in particular before any digestion of genomic DNA with non-methylation-specific restriction enzymes, or before linkers are ligated to the resulting fragments, or before all fragments are subjected to a methylation-specific restriction enzyme digestion. In case of the enrichment of unmethylated DNA, an aliquot of reference sample is treated appropriately so that all cytosines of CpG dinucleotides are unmethylated (0% methylated reference sample). Such a treatment can be any kind of chemical or enzymatic treatment, in particular the genomic DNA is subject to amplification as well known to those skilled in the art. Such an amplification is preferably carried out according to whole genome amplification methods as described above (see section IV "Labeling"). Most preferably the isothermal "Multiple Displacement Amplification" (MDA) is used. The DNA is reacted with random primers and a DNA polymerase. The polymerase is capable of displacing the non-template strand of the DNA double strand during the amplification (e.g., a $\phi$29 polymerase). The displaced strands serve as a matrix for the extension of further primers.

An amplification of a genomic DNA region is present in the genome of a test sample, i) if the signal for a test sample has an increased intensity in comparison to the signal of the corresponding 100% methylated reference sample (in case of enrichment of methylated DNA) or ii) if the signal for a test sample has an increased intensity in comparison to the signal of the corresponding 0% methylated reference sample (in case of the enrichment of unmethylated DNA). In either case, the genomic DNA region is present at higher copy-numbers in the genomic DNA of the test sample compared to the genomic DNA of the reference sample. The amplification of the copy-number is thereby proportional to the increase of the hybridization signal relative to the 100% methylated reference sample or the 0% methylated reference sample, as applicable.

Second, it is also possible to treat an aliquot of the test sample in addition to an aliquot of the reference sample according to the enrichment of choice. For enrichment of methylated DNA, an aliquot of a test sample and an aliquot of a reference sample are treated appropriately so that all cytosines of CpG dinucleotides are methylated (100% methylated test sample and 100% methylated reference sample). As explained, such a treatment can be any kind of treatment, preferably a treatment with a methyltransferase, in particular a treatment with the methyltransferase SssI. Again, the treatment can take place before or in between the enrichment according to method II, in particular before any digestion of genomic DNA with non-methylation-specific restriction enzymes, or before linkers are ligated to the resulting fragments, or before all fragments are subjected to a methylation-specific restriction enzyme digestion. For enrichment of unmethylated DNA, an aliquot of test sample and an aliquot of a reference sample are treated appropriately so that all cytosines of CpG dinucleotides are unmethylated (0% methylated test sample and 0% methylated reference sample). As already explained, such a treatment can be any kind of chemical or enzymatic treatment, in particular the genomic DNA is subject to amplification according to art-recognized methods. Such an amplification is preferably carried out according to whole genome amplification methods as described above (see section IV "Labeling"). Most preferably the isothermal "Multiple Displacement Amplification" (MDA) is used. The DNA is reacted with random primers and a DNA polymerase. The polymerase is capable of displacing the non-template strand of the DNA double strand during the amplification (e.g. a φ29 polymerase). The displaced strands serve as a matrix for the extension of further primers.

In this case, an amplification of a genomic DNA region is present in the genome of a test sample, i) if the signal for the 100% methylated test sample has an increased intensity in comparison to the signal of the corresponding 100% methylated reference sample (in case of enrichment of methylated DNA) or ii) if the signal for the 0% methylated test sample has an increased intensity in comparison to the signal of the corresponding 0% methylated reference sample (in case of enrichment of unmethylated DNA). In either case, the genomic DNA region is present at higher copy-numbers in the genomic DNA of the test sample compared to the genomic DNA of the reference sample. The amplification of the copy-number is thereby proportional to the increase of the hybridization signal of the test sample relative to that of the reference sample.

Embodiment III

A preferred embodiment comprises:
generating DNA fragments derived from a test sample, a completely methylated aliquot of a reference sample and of a completely unmethylated aliquot of said reference sample by enrichment of methylated DNA;
obtaining a value represented by the quotient of the difference of the signal intensity of the test sample and the signal intensity of the completely unmethylated reference sample to the difference of the completely methylated reference sample and the completely unmethylated reference sample;
deducing that values larger than 1 represent an increase of the copy-number of the analyzed genomic region in the test sample.

A further preferred embodiment comprises:
generating DNA fragments derived from a test sample, a completely methylated aliquot of a reference sample and of a completely unmethylated aliquot of said reference sample by enrichment of unmethylated DNA;
obtaining a value represented by the quotient of the difference of the signal intensity of the test sample and the signal intensity of the completely methylated reference sample to the difference of the completely unmethylated reference sample and the completely methylated reference sample; and
deducing that values larger than 1 represent an increase of the copy-number of the analyzed genomic region in the test sample.

According to this embodiment, genomic DNA derived from a reference sample is subject to two different treatments. On the one hand an aliquot of the genomic DNA of a reference sample is treated so that completely unmethylated DNA is generated (0% methylated reference sample). Such a treatment can be of any suitable chemical or enzymatic treatment, in particular the genomic DNA is subject to amplification as is well known in the art. Such amplification is preferably carried out according to whole genome amplification methods as described above (see section IV "Labeling"). Most preferably the isothermal "Multiple Displacement Amplification" (MDA) is used. The DNA is reacted with random primers and a DNA polymerase. The polymerase is capable of displacing the non-template strand of the DNA double strand during the amplification (e.g. a φ29 polymerase). The displaced strands serve as a matrix for the extension of further primers.

On the other hand, an aliquot of the genomic DNA of a reference sample is treated so that all cytosines of CpG dinucleotides are methylated (100% methylated reference sample). Such a treatment can be of any suitable treatment, for example a treatment with a methyltransferase, in particular a treatment with the methyltransferase SssI.

According to this embodiment, methylated or unmethylated DNA is enriched as described above from the test sample as well as from the 0% methylated and the 100% methylated reference sample. In the following, enriched methylated DNA from the test sample, the 0% methylated and the 100% methylated reference sample are compared with each other or enriched unmethylated DNA from the test sample, the 0% methylated and the 100% methylated reference sample are compared with each other.

Where unmethylated DNA is enriched, the maximal signal will result from the 0% methylated reference sample while the minimal signal will result from the 100% methylated sample. On the other hand, where methylated DNA is enriched, the maximal signal will result from the 100% methylated reference sample while the minimal signal will result from the 0% methylated sample.

Equally, if methylated or unmethylated DNA is enriched, an "X-value," as referred to herein, is calculated for each oligonucleotide or nucleic acid of the array or corresponding arrays. Accordingly, this X-value is defined by the following formula:

$$X = \frac{I_{test} - I_{min}}{I_{max} - I_{min}}$$

Wherein $I_{test}$ represents the signal intensity obtained for the test sample, $I_{min}$ represents the signal intensity obtained for the 100% methylated reference sample if unmethylated DNA is enriched or for the 0% methylated reference sample if methylated DNA is enriched, and $I_{max}$ represents the signal intensity obtained for the 0% methylated reference sample if unmethylated DNA is enriched or for the 100% methylated reference sample if methylated DNA is enriched.

In case, X-values larger than "1" are obtained, an amplification of the corresponding region in the genome of the test sample has occurred. To determine the actual copy number, the above-described embodiments I or II has to be performed. With knowledge of the copy number, a person of ordinary skill in the art will know how to interpret the signal intensity for the corresponding fragments of said genomic region and to calculate the percentage of methylation (see section V) from the signal intensity.

VII. Quantification of Signal Intensities

In particular embodiments, the signal intensities are not quantified. However, it may be favourable in certain cases to quantify the signal intensities. Therefore, in a preferred embodiment, signal intensities derived by the inventive means are quantified. Such a quantification can be performed by suitable methods familiar to those of ordinary skill in the art.

In a particular preferred embodiment, quantification is performed as follows: Genomic DNA derived from a reference sample is subject to two different treatments. On the one hand, an aliquot of the genomic DNA of a reference sample is treated so that completely unmethylated DNA is generated (0% methylated reference sample). Such a treatment can be of any suitable chemical or enzymatic treatment, in particular the genomic DNA is subject to amplification as familiar in the art. Such an amplification is preferably carried out according to whole genome amplification methods as described above (see section IV, "Labeling"). Most preferably the isothermal "Multiple Displacement Amplification" (MDA) is used. The DNA is reacted with random primers and a DNA polymerase. The polymerase is capable of displacing the non-template strand of the DNA double strand during the amplification (e.g. a φ29 polymerase). The displaced strands serve as a matrix for the extension of further primers.

On the other hand, an aliquot of the genomic DNA of a reference sample is treated so that all cytosines of CpG dinucleotides are methylated (100% methylated reference sample). Such a treatment can be of any suitable treatment, for example a treatment with a methyltransferase, in particular a treatment with the methyltransferase SssI.

According to this embodiment, methylated or unmethylated DNA is enriched as described above from genomic DNA of the test sample as well as from the said 0% methylated and the said 100% methylated reference samples. In the following, enriched methylated DNA from the test sample, from the 0% methylated and from the 100% methylated reference sample are taken into account, or enriched unmethylated DNA from the test sample, from the 0% methylated and from the 100% methylated reference sample are taken into account. Of course it is possible, but not necessary, to calculate the mean value and other statistically relevant values from the results obtained for methylated and unmethylated DNA.

DNA fragments derived from genomic DNA isolated from test and reference samples are labeled and hybridized to a DNA-microarray, in particular an oligonucleotide microarray according to the invention as described above (see section I, II, III and IV). Of course more than two samples can be compared simultaneously if distinguishable labels are used.

According to the invention, hybridization can be performed in different ways. In a particularly preferred embodiment, different identical arrays are used, on each array only DNA fragments derived from genomic DNA of a single sample are hybridized.

In another particularly preferred embodiment, each sample of DNA fragments obtained from genomic DNA of different samples is labeled differentially. Thus, the differentially labeled DNA can be applied to the same array. Moreover, it is preferred that only some of DNA fragment samples are labeled differentially and hybridized to the same array. DNA fragments derived from other samples and labeled with the same labels are hybridized on a different array.

In a further particularly preferred embodiment, DNA fragments derived from one or more test samples are hybridized each to a different identical or all to the same array. The data resulting from these hybridizations is then compared with data obtained previously for DNA fragments of a reference sample.

In case methylated DNA is enriched, the maximal signal will result from the 100% methylated reference sample while the minimal signal will result from the 0% methylated sample.

For determination of the percentage of methylation, an "X-value," as referred to herein, is calculated for each oligonucleotide or nucleic acid of the array or corresponding arrays. According to the invention, this X-value is defined by the following formula:

$$X = \frac{I^M_{test} - I^M_{0\%}}{I^M_{100\%} - I^M_{0\%}}$$

Wherein $I^M_{test}$ represents the signal intensity obtained for the test sample by means of methylated DNA enrichment, $I^M_{0\%}$ represents the signal intensity obtained for the 0% methylated reference sample by means of methylated DNA enrichment, and $I^M_{100\%}$ represents the signal intensity obtained for the 100% methylated reference sample by means of methylated DNA enrichment.

Where unmethylated DNA is enriched, the maximal signal will result from the 0% methylated reference sample while the minimal signal will result from the 100% methylated sample. For determination of the percentage of methylation, an "X-value," as referred to herein, is calculated for each oligonucleotide or nucleic acid of the array or corresponding arrays. According to the invention, this X-value is defined by the following formula:

$$X = 1 - \frac{I^{UM}_{test} - I^{UM}_{100\%}}{I^{UM}_{0\%} - I^{UM}_{100\%}}$$

Wherein $I^{UM}_{test}$ represents the signal intensity obtained for the test sample by means of unmethylated DNA enrichment, $I^{UM}_{100\%}$ represents the signal intensity obtained for the 100% methylated reference sample by means of unmethylated DNA enrichment, and $I^{UM}_{0\%}$ represents the signal intensity obtained for the 0% methylated reference sample by means of unmethylated DNA enrichment.

In either case, the X-value is a number from which the degree of methylation can be deduced. In case the X-value is "0", all cytosines of the analysed CpG dinucleotides in the corresponding genomic DNA region are unmethylated. X-values in the range between "0" and "1" multiplied by 100% result in the percentage of methylated cytosines of the analysed CpG dinucleotides. An X-value of "1" represents a 100% methylation of all cytosines of the analysed CpG dinucleotides in the corresponding genomic DNA region.

A preferred embodiment comprises:
  generating DNA fragments derived from a test sample, a completely methylated aliquot of a reference sample and of a completely unmethylated aliquot of said reference sample by enrichment of methylated DNA;
  obtaining a value represented by $$\frac{I^M_{test} - I^M_{0\%}}{I^M_{100\%} - I^M_{0\%}}$$

wherein $I^M_{test}$ represents the signal intensity obtained for the test sample by means of methylated DNA enrichment, $I^M_{0\%}$ represents the signal intensity obtained for the 0% methylated reference sample by means of methylated DNA enrichment, and $I^M{}_{100\%}$ represents the signal intensity obtained for the 100% methylated reference sample by means of methylated DNA enrichment; and deducing, if said value is i) "0" that all analyzed cytosines in the corresponding genomic DNA region of the test sample are unmethylated, ii) in the range between "0" and "1" that the value multiplied by 100 represents the percentage of methylated cytosines in the corresponding genomic DNA region of the test sample, or iii) "1" that all analyzed cytosines in the corresponding genomic DNA region of the test sample are methylated.

Another preferred embodiment comprises:

generating DNA fragments derived from a test sample, a completely methylated aliquot of a reference sample and of a completely unmethylated aliquot of said reference sample by enrichment of unmethylated DNA;

obtaining a value represented by $$1 - \frac{I^{UM}_{test} - I^{UM}_{100\%}}{I^{UM}_{0\%} - I^{UM}_{100\%}}$$

wherein $I^{UM}{}_{test}$ represents the signal intensity obtained for the test sample by means of unmethylated DNA enrichment, $I^{UM}{}_{100\%}$ represents the signal intensity obtained for the 100% methylated reference sample by means of unmethylated DNA enrichment, and $I^{UM}{}_{0\%}$ represents the signal intensity obtained for the 0% methylated reference sample by means of unmethylated DNA enrichment; and deducing, if said value is i) "0" that all analyzed cytosines in the corresponding genomic DNA region of the test sample are unmethylated, ii) in the range between "0" and "1" that the value multiplied by 100 represents the percentage of methylated cytosines in the corresponding genomic DNA region of the test sample, or iii) "1" that all analyzed cytosines in the corresponding genomic DNA region of the test sample are methylated.

VIII. Further Use of all Embodiments According to the Invention

The embodiments according to the invention are also suitable for the discovery of targets. Targets are proteins or enzymes, the modulation of which is correlated with defined diseases. By determining such a correlation, a substance can be selected or generated, which modulates the target or target forerunners or target successors (up-stream or down-stream of the determined target in a biological pathway) such that the disease-correlated modulation of the target is terminated. Such substances are then suitable for making pharmaceutical compositions for the prophylaxis or therapy of the disease.

The method according to the invention is also suitable for the discovery of response markers. Response markers are regulatory regions of the genome, for instance silencers, enhancers, promoters, etc., or the respective proteins or enzymes, which are correlated with the effect or non-effect of a specific chemical therapy of a defined disease. By determining such a correlation and the analysis thereof, then the chances of success for a prospective therapy of a patient can be determined and/or a patient-specific therapy can be developed by exclusion of therapeutic measures, for which the patient is a non-responder.

Therefore, the invention further relates to the use of a method according to the invention for identifying a response marker, wherein a first solution with DNA, which originates from a tissue sample with tissue from a non-responder, is analyzed according to the invention, wherein a second solution with DNA, which originates from a tissue sample of the same tissues type, however from a responder, is analyzed according to the invention, wherein the first solution and the second solution are simultaneously or successively contacted with the DNA microarray and hybridized thereon, wherein such immobilized nucleic acids are selected, to which mainly the fragments of the first solution or of the second solution are hybridized or not hybridized. By such a selected nucleic acid, DNA fragments are identified, which comprise regulatory and/or coding regions of one or several genes. Thus, the corresponding proteins, peptides or RNAs are derived.

Additionally, for the above method for the discovery of a target, a known modulator of the coded protein, peptide or RNA determined as mentioned above can be assigned to the specific indication of the diseased tissue. Therefore, the invention further also comprises the use of a modulator assigned by such a method for preparing a pharmaceutical composition with the specific indication, in particular a specific cancer indication.

In further embodiments, the invention provides for the use of a method according to the invention or of a test kit according to the invention for the diagnosis of a disease, for example, a cancer disease. A tissue sample is taken from a patient, which is then processed in a conventional way and subjected to the method using the test kit.

All of the cited documents herein are hereby incorporated by reference in their entireties.

DEFINITIONS

The term "treatment" also comprises the prophylaxis and the follow-up treatment (e.g. of a tumor not detectable anymore or of a stable tumor). The term "prophylaxis" comprises, in conjunction with the detection, the medical check-up as well. The term "detection" or "diagnosis" and/or "treatment" or "therapy" of a cancer disease comprises as an option also the detection and/or treatment of metastases of primary tumors in other tissues.

The term "prognosis" as used herein comprises statements about the probability of a therapy success or treatment success, and/or statements about the aggressiveness of a disease, and/or statements about the assumed life time without the occurrence of further disease symptoms or metastases and/or about the probability of the necessity of an additional treatment, and/or about the compatibility of undesired side effects.

Suitable targets or nucleic acid sequences coding for suitable targets can be taken from the documents mentioned in the specification.

The amplification of a fragment of a polynucleic acid can for instance be performed by means of the PCR technology. With regard to the experimental details, reference is for instance made to the document WO 2003/087774.\

With regard to the definition of a "linker" and its structure, again reference is made to the document WO 2003/087774. As a synonym for the term linker, the term "adapter" is used herein.

"Oligonucleotides" as referred to herein are nucleic acids having a length of 10 to less than 200, in particular of 20 to 100 or 40 nucleotides or base pairs. Oligonucleotides may be connected to a substrate of a microarray by "spacers" and thus be immobilized. As spacers, nucleic acids having a length of up to 30 nucleotides or base pairs may be used. Alternatively, spacers may be organic compounds, which are chemically connected to one end of an oligonucleotide and are bound with the opposite end to the substrate. Such compounds are known to those of ordinary skill in the relevant art.

"Methylation-specific restriction enzymes" or "methylation-sensitive restriction enzymes" are enzymes that: cut a nucleic acid sequence only if the recognition site is either not methylated or hemi-methylated; or that cut only if the latter is methylated. For restriction enzymes, which specifically cut if the recognition site is not methylated or hemimethylated, the cut will not take place, or with a reduced efficiency, if the recognition site is methylated. For restriction enzymes, which specifically cut if the recognition site is methylated, the cut will not take place, or with a reduced efficiency, if the recognition site is not methylated. Preferred are methylation-specific restriction enzymes, the recognition sequence of which contains a CG dinucleotide (for instance cgcg or cccggg). Further preferred for some embodiments are restriction enzymes that do not cut if the cytosine in this dinucleotide is methylated at the carbon atom C5.

"Non-methylation-specific restriction enzymes" or "non-methylation-sensitive restriction enzymes" are restriction enzymes that cut a nucleic acid sequence irrespective of the methylation state with nearly identical efficiency. They are also called "methylation-unspecific restriction enzymes."

A restriction enzyme generates by cutting a "blunt end," if the double strand of the cut nucleic acid is cut at cutting sites being exactly opposite to each other, with reference to the double strand. A restriction enzyme generates by cutting a "sticky end," if the double strand of the cut nucleic acid is cut with the cutting sites not being exactly opposite to each other, with reference to the double strand, but rather forms an overhang at one strand of the double strand.

A "methylation pattern" of a polynucleic acid designates the characterization of the nucleic acid sequence as to which nucleotides that are capable of being methylated are in fact methylated, and which nucleotides that are capable of being methylated are not methylated. A methylation pattern may be given for defined partial regions of the polynucleic acid or for the whole polynucleic acid.

A "hypomethylation" of a DNA section exists, for example, if a dense series of CpG dinucleotides has nearly no methylation.

A "hypermethylation" of a DNA section exists, for example, if a dense series of CpG dinucleotides has nearly a complete methylation.

A "test kit" is an assembly of at least one chemical, biological and/or physical kit component, together with an instruction or description describing the detection of which disease the test kit is intended. Standard reagents and/or standard curves in any form (printed, stored on a data carrier, link to a database) may also be included in a test kit.

A "DNA microarray" is an arbitrary construct with a substrate or carrier, on which or in which different nucleic acid species, such as genes, gene fragments or other oligonucleotides or polynucleotides are arranged, respectively at different defined places assigned to the respective nucleic acid species. Typically, at respectively one place one nucleic acid species is arranged. There may, however, also be a defined mixture of different nucleic acid species arranged at respectively one place, where, for example, every place carries a different mixture. The nucleic acids may be immobilized, this is however not necessarily required, depending on the used substrate or carrier. Examples for microarrays include, but are not limited to: nucleic acid microarrays, gene microarrays, microtiter plates with nucleic acid solutions in the wells, the nucleic acids being immobilized or not immobilized, and membranes with nucleic acids immobilized thereupon.

Of particular importance for the present method variants is the use of an "oligonucleotide array" microarray or chip, characterized in that oligonucleotides having a length of up to under 200 bp are immobilized on a surface.

A "modulator of a target" is a compound or substance, which either inhibits or induces the generation of the target, or reduces or increases the activity of the generated target, referred to the in vitro or in vivo activity in absence of the substance. A modulator may on the one hand be a substance, modulatingly affecting the development cascade of the target. On the other hand, a modulator may be a substance that forms a bond with the generated target, such that further physiological interactions with endogenous substances are at least reduced or increased. Modulators may also be molecules, which affect and inhibit or activate the transcription of the target gene. Such molecules may for instance be polyamides or zinc finger proteins, which prevent transcription by binding to DNA regions of the basal transcription machinery. Transcription modulation may also take place indirectly by the inhibition of transcription factors, which are essential for the transcription of the target gene. The inhibition of such transcription factors may, for example, be guaranteed by binding to so-called decoy aptamers.

Modulators may be natural or synthetic molecules that specifically bind to a target or target forerunner or target successor. They may also be target-specific antibodies, for instance human, humanized and non-humanized polyclonal or monoclonal antibodies. The term antibodies further includes phage display antibodies, ribozyme display antibodies (covalent fusion between RNA and protein) and RNA display antibodies (produced in vitro). The term also includes antibodies that are modified by chimerization, humanization or deimmunization, and specific fragments of the light and/or heavy chain of the variable region of basic antibodies of the above type. The production or extraction of such antibodies with given immunogenes is well known in the art. Also included are bispecific antibodies, which on the one hand bind to a trigger molecule of an immune effector cell (e.g. CD3, CD16, CD64), and on the other hand to an antigen of the tumor target cell. This will, for example, cause in the case of such binding, killing of a tumor cell. Modulators may for instance also be suitable target-specific anticalins and affibodies mimicrying an antibody.

A "specific cancer disease" is an organ-specific cancer disease, such as lung cancer, ovary cancer, scrotal cancer, prostate cancer, pancreas cancer, breast cancer, cancer of an organ of the digestive tract, etc. Suitable sequences with regard to all aspects of the present invention are for instance described in the documents DE 20121979 U1, DE 20121978 U1, DE 20121977 U1, DE 20121975 U1, DE 20121974 U1, DE 20121973 U1, DE 20121972 U1, DE 20121971 U1, DE 20121970 U1, DE 20121969 U1, DE 20121968 U1, DE 20121967 U1, DE 20121966 U1, DE 20121965 U1, DE 20121964 U1, DE 20121963 U1, DE 20121961 U1, DE 20121960 U1, DE 10019173 A1, DE 10019058 A1, DE 10013847 A1, DE 10032529 A1, DE 10054974 A1, DE 10043826 A1, DE 10054972 A1, DE 10037769 A1, DE 10061338 A1, DE 10245779 A1, DE 10164501 A1, DE 10161625 A1, DE 10230692, DE 10255104, EP 1268855, EP 1283905, EP 1268857, EP 1294947, EP 1370685, EP 1395686, EP 1421220, EP 1451354, EP 1458893, EP 1340818, EP 1399589, EP 1478784, WO 2004/035803, and WO 2005/001141, all of which are incorporated herein by reference in their entirety.

The "galenic preparation" of a pharmaceutical composition according to the invention may be performed in a usual way. As counter-ions for ionic compounds can for instance be used Na⁺, K⁺, Li⁺ or cyclohexyl ammonium. Suitable solid or liquid galenic preparation forms are for instance granulates, powders, dragees, tablets, (micro) capsules, suppositories, syrups, juices, suspensions, emulsions, drops or injectable solutions (IV, IP, IM, SC) or fine dispersions (aerosols), transdermal systems, and preparations with protracted release of active substance, for the production of which usual means are used, such as carrier substances, explosives, binding, coating, swelling, sliding or lubricating agents, tasting agents, sweeteners and solution mediators. As auxiliary substances are named here magnesium carbonate, titanium dioxide, lactose, mannite and other sugars, talcum powder, milk protein, gelatin, starch, cellulose and derivatives, animal and vegetable oils such as cod-liver oil, sunflower oil, peanut oil or sesame oil, polyethylene glycols and solvents, such as sterile water and mono or multi-valent alcohols, for instance glycerin. A pharmaceutical composition according to the invention can be produced by that at least one modulator used according to the invention is mixed in a defined dose with a pharmaceutically suitable and physiologically well tolerated carrier and possibly further suitable active, additional or auxiliary substances with a defined inhibitor dose, and is prepared in the desired form of administration.

"Response markers" are proteins or enzymes or modifications of a nucleic acid (such as SNP or methylation), which are correlated with the cellular response of a cell to an exogenous substance, in particular a therapeutic substance. Different patients react in different ways to a specific therapy. This is based on the patient-individual cellular responses to a therapeutic substance. By a differential analysis of identical tissues of different persons, the persons suffering from the same disease and being treated with the same therapy, however reacting in different ways to the therapy (e.g., by healing processes of different speeds or different disadvantageous effects such as side effects), such response markers can be identified, and on the one hand the (differential) existence of a protein or enzyme or a modification of the nucleic acid, but also its absence will qualify it as a response marker.

"Repeats" also called "repetitive sequences" or "redundant sequences," are sequences, which are present in many copies in a nucleic acids, for instance in genomic DNA.

"DMH amplificates" or "amplicons" are DNA fragment mixtures according to the invention, which were obtained by one or several restriction digestions with one or several restriction enzymes according to the invention, and which were amplified by PCR by means of primers, wherein the primers hybridize at linkers (adapters), which were ligated after a restriction digestion with one or several restriction enzymes.

EXAMPLES

Example 1

Preparation of Two Solutions with One Genomic DNA Each from Two Adjacent Tissue Samples of a Patient Samples of tumor tissue and adjacent non-neoplastic tissue are obtained from patients that were subjected to a mastectomy. The genomic DNA from these tissues is respectively isolated by means of the QIAamp DNA Mini Kit (Qiagen, Hilden, Germany) in accordance with the manufacturer's instructions. Two preparations are obtained, one with genomic DNA from diseased tissue and one with genomic DNA from healthy tissue.

Example 2

Preparation of a DNA Microarray with Oligonucleotides

The definition of the various oligonucleotides for the microarray is performed as follows: As a database serves the Human Genom Ensembl Version NCBI 33 database. It is downloaded from the server (www.ensembl.org) in the fasta format. The file contains all available contigs of the human genome. By means of software, all fragments are calculated, which develop (are derivable) by using the non-methylation-specific restriction enzyme or enzymes that are used during the preparation of the solution of fragments. This takes place by recognition of the respective cutting sites of the restriction enzymes and "in silico" cut. Fragments thus calculated having less than 100 and more than 1,200 base pairs are (virtually) sorted out. The remaining fragments are tested for cutting sites for the used methylation-specific restriction enzymes by identifying the corresponding recognition sequences. Fragments without such recognition sequences are sorted out. For the remaining fragments, further the share of repeats is determined "in silico". If the share is above 20%, such fragments are sorted out. From the remaining fragments, in an arbitrary manner or according to further criteria being not essential for the invention, a number of partial sequences are selected as oligonucleotides, which are intended for use on the microarray. These oligonucleotide sequences are then synthesized in a conventional manner on a substrate of a microarray.

Example 3

Preparation of Two Solutions with Fragments of the Respective DNA Samples of Example 1 With Methylation-Sensitive Restriction Section 1: 2 µg each of the genomic DNA of the preparations of Example 1 are first fragmented with 5 units each of the non-methylation-specific restriction enzymes MseI, Bfa1 and Csp6 (available from: New England Biolabs and MBI Fermentas) for 16 hours at 37° C. according to manufacturer's instructions. Then, these restriction enzymes are inactivated for 20 minutes at 65° C.

Section 2: Thereafter the QiaQuick PCR product purification column kit (Qiagen, Hilden, Germany) is used for purification. According to the manufacturer's information, fragments shorter than 40 bases are very efficiently removed. It is however not excluded that larger fragments up to a size of approx. 100 bp are also removed hereby. Then, according to the procedure of Huang et al. (*Hum Mol Genet*, 8(3):459-470, 1999), a ligation of adapters (or linkers) is carried out. For this purpose, different modifications of the original protocol are possible, which are described in the following. For the ligation, the fragmented DNA is mixed with 500 pmol adapter, 400 units T4 DNA Ligase (New England Biolabs), the volume ligase, as recommended by the manufacturer, of 10× buffer and ATP, and incubated for 16 hours at 16° C. The adapters are previously prepared by an equimolar mixture of the oligonucleotides H24 (5'-AGG CAA CTG TGC TAT CCG AGG GAT-3') (SEQ ID NO:1) and H12 (5'-TAA TCC CTC GGA-3') (SEQ ID NO:2) is first denatured for 5 min at 95° C., and, step by step, cooled down to 25° C. The ligated DNA is finally purified by means of the QuiaQuick PCR product purification kit (Qiagen, Hilden, Germany).

Thereafter, fragmentation is carried out with 10 units each of the methylation-sensitive (i.e. methylation-specific)

restriction enzymes BstU1, HapII, HpyCH4IV and HinP1 (available from: New England Biolabs) for 8 hours at 37° C. and then for 8 hours at 60° C. according to manufacturer's specification. The fragmented DNA is finally purified by means of the QuiaQuick PCR product purification kit (Qiagen, Hilden, Germany).

Approx. 10-100 ng are used in a PCR reaction, which simultaneously serves for the amplification of a representation of uncut DNA fragments of the order of 50-1,000 bp. The PCR reaction batch contains 350 µM dNTPs, 2.5 µM labelled primer (H24), 5 units DeepVent (exo-) DNA polymerase, 10 µl 10× buffer and 5% DMSO in a volume of 100 µl. The amplified DNA is finally purified by means of the QuiaQuick PCR product purification kit (Qiagen, Hilden, Germany).

10-12 PCR reactions are carried out with each sample, in order to obtain a total amount of 20 µg PCR product after the purification. The purified PCR products were fragmented and labeled according to the specification in the "Gene Chip Mapping Assay Manual" of Affymetrix Inc., in particular chapter 4 (page 38-42).

Thus samples of diseased and of adjacent healthy tissue are obtained, which are suitable for hybridization with the oligonucleotide microarray of Example 2 or the DNA microarray of Example 8.

Example 4

Hybridization of the Samples on the DNA Microarray

The two solutions obtained in Example 3 (or in Example 9 below) are each hybridized with a DNA microarray according to Example 2. Hybridization and detection take place according to the specification in the "Gene Chip Mapping Assay Manual" of Affymetrix Inc., in particular chapter 4 (page 44-45), and chapter 6 "Washing, Staining & Scanning" (page 75-92).

Two methylation patterns are obtained, and from a comparison of the two methylation patterns, differences between diseased and healthy tissue can be recognized. With regard to the differences, the respective oligonucleotide set of the DNA microarray is identified and assigned, if applicable, to one or several proteins, peptides or RNAs. Normally, these proteins, peptides or RNAs are then differentially expressed in the respective patient. For the identification of a characteristic methylation pattern or for the detection of a marker (response or diagnosis marker), it is however not necessary to build up such a correlation.

If the differential methylation and the differential expression affected thereby is confirmed for other patients also having the same disease, and if applicable corresponding cell lines, then the respective expression product is a suitable target for searching substances inhibiting or inducing the expression product (depending on whether the differential expression "diseased"/"healthy" is greater or smaller than 1).

Example 5

Comparison of the Fragment Length Distribution of a Fragment Mixture Prepared According to the Invention to the Prior Art Fragment Length Distribution According to the invention, a mixture of fragments of a polynucleic acid according to Example 3, Section 1 was prepared. For comparison, the method according to the document Huang et al., see above, was performed, however with slight modifications. For instance, for a better comparison, the same amount of methylation-specific restriction enzymes was used in both methods. For both fragment solutions, then a fragment length histogram was prepared.

Figure 1:
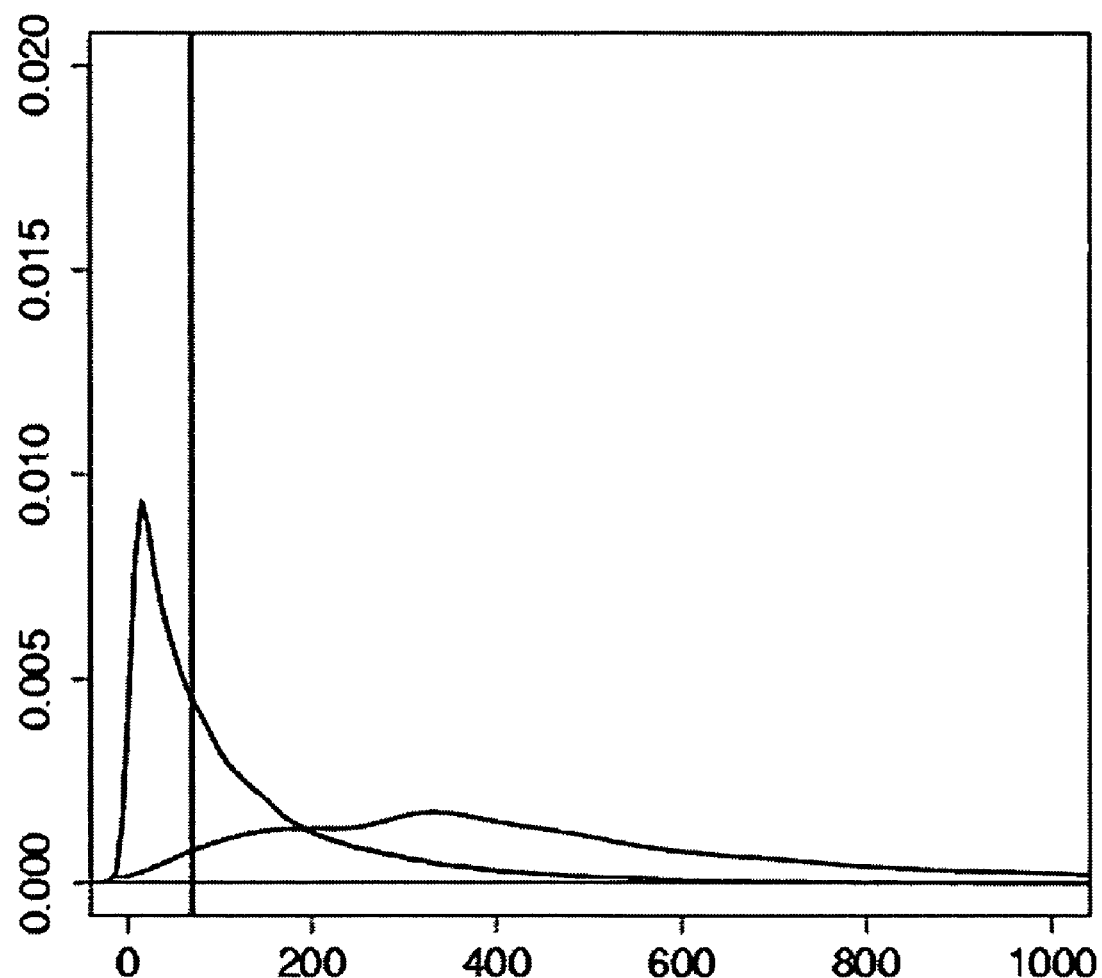
FIG. 1 shows the fragment length distribution for fragments without methylation-specific restriction sites in broken lines. The continuous lines represent the fragment length distribution for fragments with methylation-specific restriction sites. The latter are particularly interesting for the further analysis.
Figure 2:
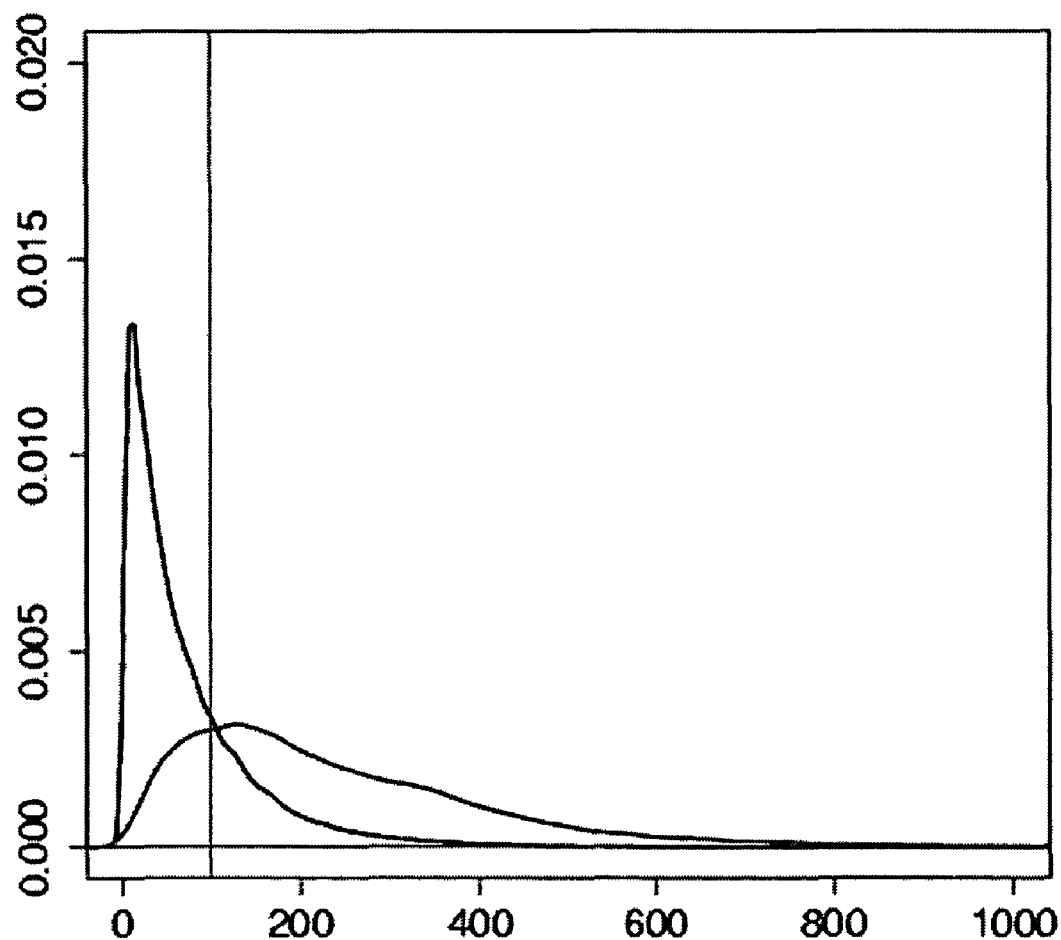
FIG. 2 shows the fragment length distribution for fragments without methylation-specific restriction sites in broken lines. The continuous lines represent the fragment length distribution for fragments with methylation-specific restriction sites.

The comparative results are shown in FIGS. 1 and 2. In both figures, the fragment length distributions for fragments without methylation-specific restriction sites are shown by broken lines. The continuous lines show the fragment length distributions for fragments with methylation-specific restriction sites. The latter are particularly interesting for the further analysis. FIG. 1 shows the results according to the prior art. FIG. 2 shows the results of the inventive method, i.e. using several methylation-unspecific restriction enzymes.

From a comparative analysis of FIGS. 1 and 2, it can be seen that with the inventive method the share of fragments without methylation-specific restriction sites and having a fragment length below 100 bp is comparatively high. Consequently, by separation or non-amplification of such short fragments, the non-interesting fragments are selectively eliminated. The relative complexity of a fragment solution prepared according to the invention is therefore reduced. The number of nucleic acids (in the size window used for the analysis) has decreased, and simultaneously the percentage (share) of fragments above 100 bp including methylation-specific restriction sites has increased.

On the other hand, using the inventive method, the CpG-rich regions that are interesting for further analysis are cut comparatively shorter, thus their amplification and detection are substantially facilitated. Furthermore, the probability that all CpG's in the fragments are co-methylated is increased.

Example 6

Hybridization with DMH Amplificates of DNA from Peripheral Blood Lymphocytes (PBL) and from the Breast Cancer Cell Line MDA-Mb-231 Demonstrated Inter and Intra Workflow Reproducibility In order to evaluate the optimized inventive method, DMH amplificates of DNA from peripheral blood lymphocytes (PBL) and from the breast cancer cell line MDA-MB-231 were each prepared twice. These DMH amplificate solutions were divided up, and hybridization samples were generated therefrom, which were hybridized on the specifically prepared Affymetrix microarrays. FIGS. 5A and 5B illustrate the inter and intra workflow reproducibility of 0.93-0.95.

Example 7

Figure 5:
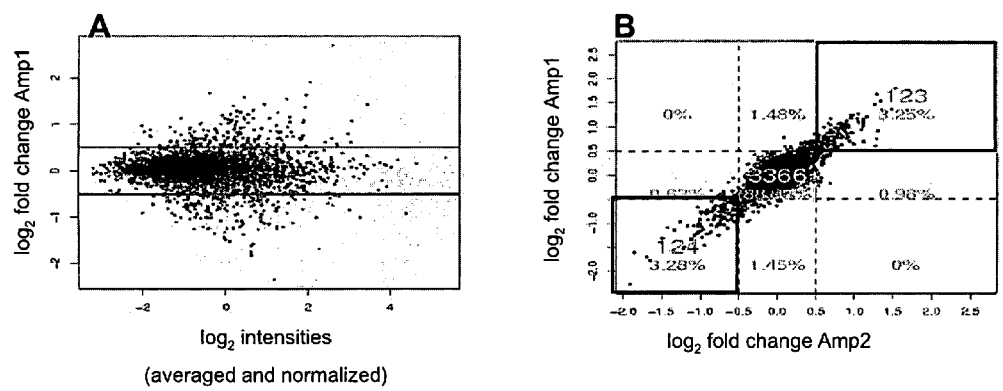
FIG. 5 shows selection of marker candidates and reproducibility. A) Distribution of $\log_2$ ration against the mean hybridization signal intensities of all fragments of the DMH amplicon generated from PBL and breast cancer cell line DNA. Dots above and below the red lines indicate potential marker candidates being methylated (log ratio<−0.5) or unmethylated (log ratio>0.5) in breast cancer cell line compared to PBL. B) Correlation plot of two DMH discovery experiments using PBL and breast cancer cell line samples. Dots in the red boxes indicate potential marker fragments reproducibly found in both experiments to be either methylated or unmethylated in breast cancer cell lines compared to PBL.

Potential Marker Candidates that are Differentially Methylated Between PBL and Breast Cancer Cell Lines were Reproducibly Identified 247 potential marker candidates being differentially methylated between PBL and breast cancer cell lines were reproducibly identified (FIG. 5). Fragments were identified as potential candidates if the log 2 difference of the average hybridization signal (log 2 fold change) between two DNA samples was greater than 0.5 (above and below the red line FIG. 5A). For validating these marker candidates, 111 fragments (from the 247) were randomly selected from three groups, which could be separated according to their log 2 fold change differences (>0.6, 0.4-0.6 and <0.4), and were subjected to a direct bisulfite sequencing.

This validation confirmed a high correlation coefficient of 0.71 between log 2 fold change differences and methylation values, which were obtained by the direct bisulfite sequencing (FIG. 6).

Example 8

Preparation of a DNA Microarray with CpG-Rich DNA Fragments

A DNA microarray is prepared according to the instructions of the document Yan et al., *Cancer Res.*, 61:8375-8380, 2001.

Example 9

Preparation of Two Solutions with Fragments of the Respective DNA Samples of Example 1 Without Non-Methylation-Sensitive Restriction Enzymes 2 µg each of the genomic DNA of the preparations of Example 1 are fragmented with 10 units of the methylation-sensitive restriction endonuclease HapII (New England BioLabs) for 16 hours at 37° C. according to manufacturer's specification, and then the Enzyme is inactivated for 20 minutes at 65° C.

After the restriction, according to the procedure of Huang et al (*Hum Mol Genet,* 8(3):459470, 1999), a ligation of adapters, and subsequent PCR amplification of the fragmented DNA by means of theses adapters is performed. For this purpose, different modifications of the original protocol are necessary, which are described in the following.

For the ligation, the fragmented DNA is mixed with 500 pmol adapter, 400 units T4 DNA ligase (New England Biolabs), the volume ligase, as recommended by the manufacturer, of 10× buffer and ATP, and incubated for 16 hours at 16° C. The adapters are previously prepared by that an equimolar mixture of the oligonucleotides H24 (5'-AGG CAA CTG TGC TAT CCG AGG GAT-3') (SEQ ID NO:1) and H12-M (5'-CGA TCC CTC GGA-3') (SEQ ID NO:2) is first denaturated for 5 min at 95° C. and step by step cooled down to 25° C.

The ligated DNA is purified by means of the QuiaQuick PCR product purification kit (Qiagen, Hilden, Germany). Approx. 10-100 ng are used in a PCR reaction, which simultaneously serves for the amplification of a representation of DNA fragments in the order of 50-1,000 bp, and for labelling with different fluorescence labels the PCR products of the DNA samples, which were generated from diseased and from adjacent healthy tissue.

The PCR reaction batch for the DNA sample of the diseased tissue contains 350 µM dNTPs, 0.7 µl Cy5-CTP (Amersham) or in the case of the DNA sample of the healthy tissue Cy3-CTP (Amersham), 2.5 µM Cy5 labelled primer H24 (or in the case of the DNA sample of the healthy tissue Cy3 labelled primer H24), 5 units DeepVent (exo-) DNA polymerase, 10 µl 10× buffer and 5% DMSO in a volume of 100 µl. Of course, the DNA sample of the diseased tissue can also be labelled with Cy3, and that of the healthy tissue with Cy5.

Thus samples of healthy and of adjacent diseased tissue are obtained, which are suitable for hybridization with the oligonucleotide microarray of Example 2 or the DNA microarray of Example 8.

Example 10

Hybridization of the Samples on the DNA Microarray

The two solutions obtained in Example 3 or in Example 9 are each hybridized with a DNA microarray according to Example 8. Hybridization and detection take place according to the Huang et al, Hum Mol Genet, 8(3):459-470, 1999. The two differently labelled samples are contacted simultaneously or subsequently with the DNA microarray and hybridized thereon. Immobilized nucleic acids, which mainly bind fragments either of the sample of the healthy tissue or of the diseased tissue, indicate methylation differences. In the case of such a different hybridization behavior, the respective clone of the DNA microarray is identified and can be assigned, if applicable, to one or several proteins, peptides or RNAs. Normally, such an expression product is then differentially expressed at the respective patient. If the differential expression is confirmed for other patients also having the same disease, and if applicable corresponding cell lines, then the respective expression product is a suitable target for searching substances inhibiting or inducing the expression product (depending on whether the differential expression "diseased"/"healthy" is greater or smaller than 1).

Example 11

DMH Analysis of Neoplastic Breast Tissue

Figure 3:
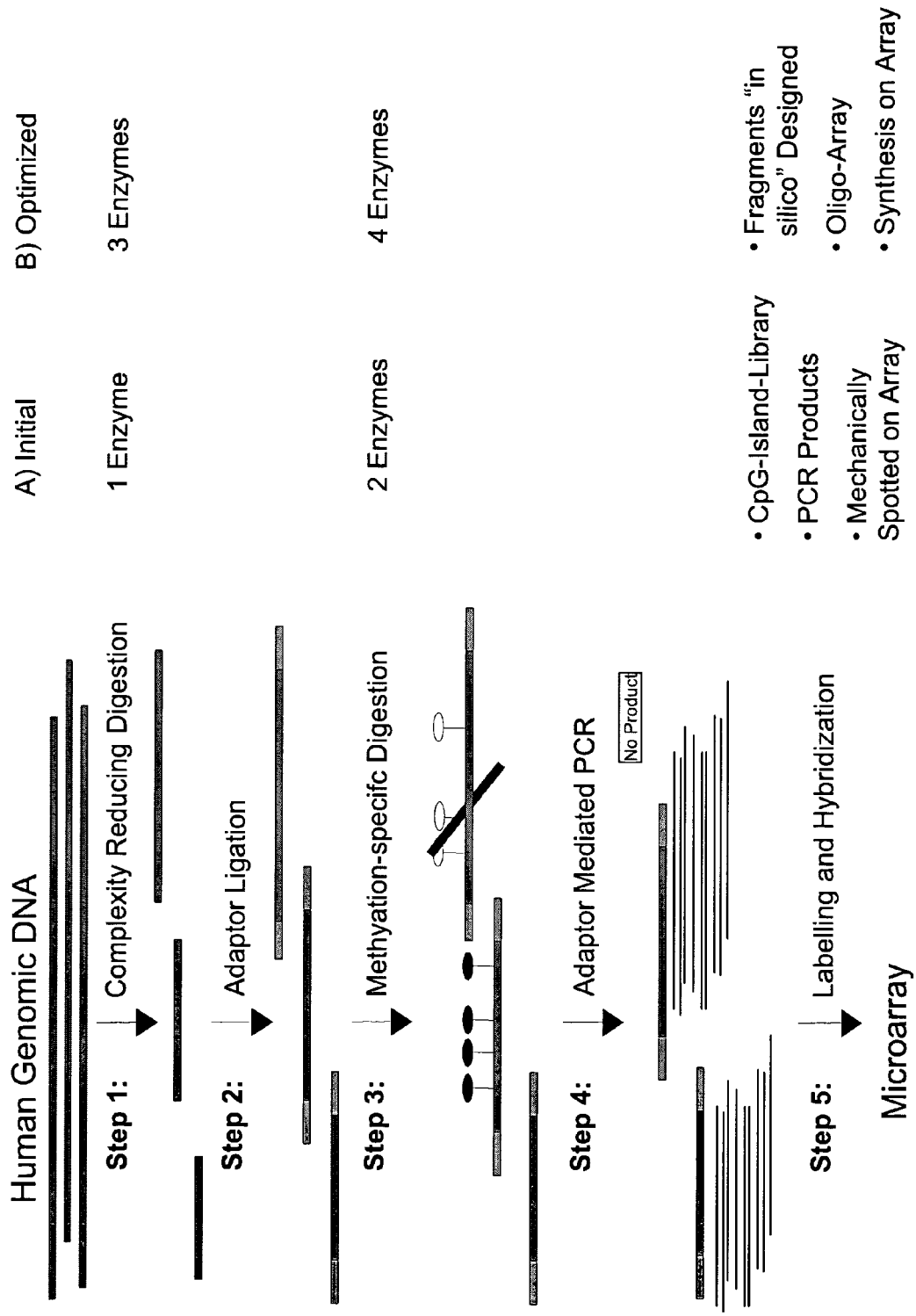
FIG. 3 shows an Illustration of the method for preparing DMH amplificates. Modifications relative to Huang et al. are indicated.
Figure 4:
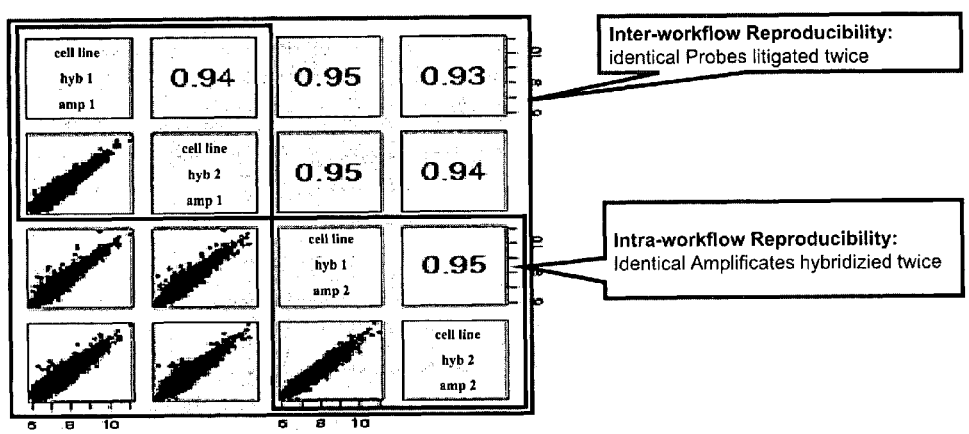
FIG. 4 shows Intra-workflow and inter-workflow reproducibility Correlation plots comparing the hybridization signal (averaged intensities of the $\log_2$ signal of all detection oligomers of a fragment) of four arrays, and DNA from breast cancer cell lines was used. The reproducibility of the complete DMH amplicon preparation (inter-workflow reproducibility, red box) and the preparation of the hybridization samples (starting with the adaptor mediated PCR, step 4, see FIG. 1) of each DMH amplicon (intra-workflow reproducibility, green boxes) was determined.

FIG. 3 illustrates the general method of the DMH (differential methylation hybridization). FIG. 3 illustrates the differences of the working procedures (workflow) of the preparation of a mixture of methylated fragments of a sample containing DNA. These fragments are referred to herein as DMH amplificates. The prior art method according to Huang et al. is compared here as an example to a method optimized according to the present invention. Both methods for detecting methylation differ not only in the preparation of the fragments, but also in the final detection platform. In the method modified according to the invention a specifically adapted (customized) Affymetrix oligonucleotide microarray is used as a detection platform. This chip carries 80,000 oligonucleotides representing approx. 9,000 of the DNA fragments, which were prepared by the DMH method optimized according to the present invention. The prior art method for preparing the fragments (DMH workflow) generates a solution of great complexity (high number of genomic base pairs that are represented by DMH amplificates). Since microarray hybridizations with DMH amplificates of high complexity result in low signal/noise ratios, the technical object is the provision of a solution of fragments with reduced complexity, without losing informative amplificates (e.g. by elimination of repetitive sequences). Further, a high general reproducibility is intended. The solution for this object is achieved by using the method according to the invention for preparing methylated fragments. The complexity of this solution can be reduced to approx. $5 \times 10^8$ bp, whereas it is $2 \times 10^9$ in the comparable DMH method. This result is illustrated in FIGS. 1 and 2.

DNA samples obtained from "aggressive" and "non-aggressive" tissue were fragmented by a non-methylation-specific restriction hydrolysis (step 1). Then adapters were ligated to the fragments, which permitted the subsequent enzymatic amplification of the fragments (step 2). The ligated fragments were then further digested by a methylation-specific restriction enzyme hydrolysis (step 3). This restriction was then subjected to an enzymatic amplification step (step 4)

and hybridized on an oligo-DNA chip (step 5). This chip is composed of a bank of detection oligonucleotides, the design of which is based on an "in silico" digestion of the human genome. Differences in the hybridization pattern between "aggressive" and "non-aggressive" samples permit the identification of differentially methylated cutting sites of restriction enzymes.

1. DNA Isolation.

Samples. Tissue samples were obtained from 17 estrogen receptor-negative female patients (Table 1). Breast tumors of 9 patients were rated "aggressive", since a metastasis occurred in these patients in the observed period. Tumors of patients, where a metastasis did not occur in the observed period were rated "non-aggressive". Three samples of peripheral blood lymphocytes served as a control.

TABLE 1

Survey of the samples used.

| Sample type | Class | Disease-free survival (months) | Total months survived | Age type | Disease re-currency |
|---|---|---|---|---|---|
| breast tumor | aggressive | 19 | 39 | 73 | metastasis |
| breast tumor | aggressive | 17 | 33 | 78 | metastasis |
| breast tumor | aggressive | 14 | 41 | 61 | metastasis |
| breast tumor | aggressive | 16 | 23 | 51 | metastasis |
| breast tumor | aggressive | 15 | 52 | 46 | metastasis |
| breast tumor | aggressive | 9 | 20 | 72 | metastasis |
| breast tumor | aggressive | 16 | 23 | 52 | metastasis |
| breast tumor | aggressive | 24 | 25 | 65 | metastasis |
| breast tumor | aggressive | 34 | 44 | 69 | metastasis |
| breast tumor | non-aggressive | 132 | 132 | 43 | — |
| breast tumor | non-aggressive | 138 | 138 | 73 | — |
| breast tumor | non-aggressive | 128 | 128 | 57 | — |
| breast tumor | non-aggressive | 91 | 91 | 57 | — |
| breast tumor | non-aggressive | 146 | 146 | 68 | — |
| breast tumor | non-aggressive | 92 | 92 | 64 | — |
| breast tumor | non-aggressive | 129 | 129 | 60 | — |
| breast tumor | non-aggressive | 112 | 112 | 72 | — |
| peripheral blood lymphocytes | n.a. | n.a. | n.a. | n.a. | n.a. |
| peripheral blood lymphocytes | n.a. | n.a. | n.a. | n.a. | n.a. |
| peripheral blood lymphocytes | n.a. | n.a. | n.a. | n.a. | n.a. |

* n.a. = not applicable

2. Preparation of the Oligonucleotide Microarray

The sequence of the different oligonucleotides, which were used for the oligonucleotide array, was determined as follows. All sequences, which were needed for designing the microarray, originate from the Ensembl Human Genome Database. The database was downloaded from the server (www.ensembl.org) in the fasta format. The file contains all available contigs of the human genome. By means of software, all oligonucleotides were designed, i.e. "in silico".

This software simulated the digestion of the human genome first by selected non-methylation-specific restriction enzymes (non-methylation-specific: the restriction is independent from the methylation state of the cutting site) and then by selected methylation-specific restriction enzymes. The software then generates the sequences of all non-methylation-sensitively digested fragments, a partial amount of these fragments was then selected for the microarray. Fragments of less than 100 and more than 1,200 base pairs were (virtually) rejected. Of the remaining fragments, those were selected, which contained a recognition site of at least one of the previously used methylation-specific restriction enzymes. Of these fragments, fragments were further selected, which have up to 20% repeats.

The thus obtained fragments can further be selected either by further criteria or randomly. The group of fragments selected at the end were then synthesized on the surface of the microarray in analogous ways as in the conventional methods.

3. Enzymatic Restriction of the DNA Samples (of Section 1).

The genomic DNA was prepared for the hybridization of the microarray:

Step 1: 2 µg each of an isolated genomic DNA sample was digested with 5 units each of the non-methylation-specific restriction enzymes MseI, Bfa1 and Csp6 (available from: New England Biolabs and MBI Fermenters) for 16 hours at 37° C. according to manufacturer's instructions. Then, these restriction enzymes were inactivated by heating for 20 minutes at 65° C.

Step 2: Thereafter the QiaQuick PCR product purification column kit (Qiagen, Hilden, Germany) was used for purification. According to manufacturer's information, fragments shorter than 40 base pairs are thereby removed. It cannot however be excluded that some larger fragments up to a size of 100 base pairs are also removed. Adapters (or linkers) were then ligated to the fragments. This took place according to the procedure described by Huang et al, *Hum Mol Genet,* 8(3): 459-470 (1999), and this protocol was adjusted as follows: The fragmented DNA was mixed with 500 pmol adapter, 400 units T4 DNA Ligase (New England Biolabs), and the volume ligase, as recommended by the manufacturer, of 10× ligase buffer and ATP. The incubation was carried out for 16 hours at 16° C. The adapters were previously prepared by an equimolar mixture of the oligonucleotides H24 (5'-AGG CAA CTG TGC TAT CCG AGG GAT-3') (SEQ ID NO:1) and H12 (5'-TAA TCC CTC GGA-3') (SEQ ID NO:2) was denaturated for 5 min at 95° C. and step by step cooled down to 25° C. Then the ligated DNA was purified by means of the QuiaQuick PCR product purification column kit (Qiagen, Hilden, Germany).

Thereafter, the purified ligated DNA was digested with 10 units each of the methylation-sensitive (i.e. methylation-specific) restriction enzymes BstU1, HapII, HpyCH4IV and HinP1 (available from: New England Biolabs) for 8 hours at 37° C. and then for 8 hours at 60° C. according to manufacturer's specification. The fragmented DNA is finally purified by means of the QuiaQuick PCR product purification column kit (Qiagen, Hilden, Germany).

Each of the ligated fragments was then amplified, in double reactions. Approx. 10-100 ng were used for a PCR reaction, which amplified only uncut DNA fragments in a region of 50-1,000 bp. The PCR reaction batch contained 350 µM dNTPs, 5 units DeepVent (exo-) DNA polymerase, 10 µl 10× buffer and 5% DMSO in a volume of 100 µl. The amplified DNA is finally purified by means of the QuiaQuick PCR product purification column kit (Qiagen, Hilden, Germany).

10-12 PCR reactions are carried out with each sample, in order to obtain a total amount of 20 µg PCR product after the purification. The purified PCR products are fragmented and labeled according to the specification in the "Gene Chip Mapping Assay Manual" of Affymetrix Inc., in particular chapter 4 (page 38-42).

4. Hybridization of the Samples on the Microarray.

As in section 3, labelled amplificates were hybridized on an oligonucleotide microarray according to section 2. Hybridization and detection took place according to the specification in the "Gene Chip Mapping Assay Manual" of Affymetrix Inc., in particular chapter 4 (page 44-45), and chapter 6 "Washing, Staining & Scanning" (page 75-92).

Every sample generated an individual hybridization pattern. Thereby, methylation differences between "aggressive" and "non-aggressive" tissue or between peripheral blood lymphocytes and tumor tissue could be derived, by determining DNA fragment sequences, which showed a differential hybridization signal for the samples of the compared tissues. Further, it was tried to identify for every identified DNA sequence a corresponding cDNA, which would have as a consequence that such a cDNA would be differentially expressed between the said groups.

The differentially methylated fragments were then subjected to a direct bisulfite sequencing, in order to obtain further information with regard to the extent of the methylation.

Example 12

Enrichment of Methylated DNA Fragments by Means of Column Chromatography

An affinity chromatography column is prepared by immobilizing the methylation-binding domain (MBD) of the protein MeCP2 of the rat by a His tag on a commercial matrix for the column chromatography. The preparation and application of this column were already described in Cross et al., *Nature Genetics,* 1994.

Genomic DNA is first fragmented by ultrasonic treatment and then applied on the column. Depending on the methylation and the CpG density, the DNA fragments are bound to the column and then collected by elution with a NaCl salt gradient in fractions. Since with increasing salt concentration, methylated fragments only having a high CpG density remain bound to the column, they are enriched in the fractions having high salt concentrations.

The enriched methylated DNA fragments are amplified with the BioPrimer Labeling Kit (Invitrogen) and then fragmented and biotin-labeled (GeneChip Mapping 10K Xba Assay Kit, Affymetrix, steps 7 and 8). In the subsequent hybridization, the methylated DNA fragments are detected.

Example 13

Enrichment of Methylated DNA Fragments by Means of Magnetic Beads

For accumulating methylated DNA fragments, magnetic beads are used, on which the methylation-binding domain (MBD) of the protein MeCP2 is immobilized.

Genomic DNA is first fragmented by ultrasonic treatment, then magnetic beads are added. Then the magnetic beads, to which methylated DNA fragments having a high CpG density are bound, are separated, and the selected DNA fragments are separated again from the magnetic beads by increasing the NaCl concentration.

The enriched methylated DNA fragments are amplified with the BioPrime Labeling Kit (Invitrogen) and then fragmented and biotin-labeled (GeneChip Mapping 10K Xba Assay Kit, Affymetrix, steps 7 and 8). In the subsequent hybridization, the methylated DNA fragments are detected.

Example 14

Enrichment of Methylated DNA Fragments by Means of Immunoprecipitation

Methylated DNA fragments are enriched by immunoprecipitation using a methyl cytosine-binding antibody (Eurogentec). This method has already been described in Weber et al., Nature Genetics, 2005.

Genomic DNA is first fragmented by ultrasonic treatment. The DNA is denatured and then immunoprecipitated. The antibody-bound DNA is separated by magnetic beads from not-bound DNA and then released.

The enriched methylated DNA fragments are amplified with the BioPrime Labeling Kit (Invitrogen) and then fragmented and biotin-labeled (GeneChip Mapping 10K Xba Assay Kit, Affymetrix, steps 7 and 8). In the subsequent hybridization, the methylated DNA fragments are detected.

Example 15

Enrichment of Methylated DNA Fragments by Means of Chromatin Immunoprecipitation DNA fragments are selected by chromatin immunoprecipitation using antibodies against transcription factors such as E2F4 (Weinmann et al., Genes and Development, 2002). By this selection, a series of DNA fragments are obtained, which are bound by a specific transcription factor, and thus fragments, which are located in regulatory regions of the genome. In order to investigate the methylation of these fragments, they are provided, as already described (see DMH: linker ligation), with linkers, methylation-specifically cut and then amplified, fragmented, biotin-labeled (GeneChip Mapping 10K Xba Assay Kit, Affymetrix, steps 7 and 8) and hybridized.

Example 16

Enrichment of Non-Methylated DNA Fragments by Using Restriction Endonucleases Cutting Methylated DNA Genomic DNA is cut with a restriction endonuclease, which only cuts if the DNA is methylated. Such enzymes are McrBC (New England Biolabs), Bis I (SibEnzyme) or Gla I (SibEnzyme). These enzymes are used in lieu of the methylation-sensitive enzymes in the methylation-specific cutting in the DMH. In this case, only unmethylated fragments are maintained and are then fragmented and biotin-labeled (GeneChip Mapping 10K Xba Assay Kit, Affymetrix, steps 7 and 8) and hybridized.

Example 17

Enrichment of Methylated DNA Fragments by Using Restriction Endonucleases Cutting Methylated DNA Further, a use is possible, as already described in Lippman et al. *Nature Methods,* 2005. Herein, the genomic DNA is first fragmented by ultrasonic treatment and then cut with McrBC. DNA fragments, which exceed a certain size and are thus not cut, are extracted from an agarose gel. The DNA thus obtained is fragmented, biotin-labeled (GeneChip Mapping 10K Xba Assay Kit, Affymetrix, steps 7 and 8) and hybridized.

Example 18

Analysis of the Fragment Length Distribution of a Fragment Mixture Prepared According to the Invention As a database serves the Human Genom Ensembl Version NCBI 33 database. It is downloaded from the server (www.ensembl.org) in the fasta format. The file contains all available contigs of the human genome. By means of software, all fragments are calculated, which would be derivable by using the non-methylation-specific restriction enzyme BstU. This takes place by recognition of the BstU cutting sites and "in silico" cut. For the fragments thus obtained the share of CpG islands is determined. For this purpose, first CpG islands on the genomic DNA are annotated according to the criterion that in a 200 bp long section, there are at least 2% CG dinucleotides. In a second step, it is verified whether fragments, which have been generated by the "in silico" digestion with BstU, are in agreement with the determined CpG islands.

FIGS. 7 and 8 show a fragment/length histogram for fragments with a share of CpG islands of more than 0.3 (FIG. 7) or of at most 0.3 (FIG. 8). The vertical marking in the figures shows respective fragments having a length of 1,000 bp.

As can easily be seen from FIG. 7, the fragments produced by the method according to the invention have for a share of CpG islands of more than 0.3 nearly exclusively a length smaller than 1,000 bp. Simultaneously, the fragments produced by the method according to the invention (method 1) with a share of CpG islands of at most 0.3 are mainly fragments having a length of more than 1,000 bp (FIG. 8).

A database serves the Human Genom Ensembl Version NCBI 33 database. It is downloaded from the server (www.ensembl.org) in the fasta format. The file contains all available contigs of the human genome. By means of software, all fragments are calculated, which would develop by using the non-methylation-specific restriction enzyme BstU. This takes place by recognition of the BstU cutting sites and "in silico" cut. For the fragments thus obtained the share of CpG islands is determined. For this purpose, first CpG islands on the genomic DNA are annotated according to the criterion that in a 200 bp long section, there are at least 2% CG dinucleotides. In a second step, it is verified whether fragments, which have been generated by the "in silico" digestion with BstU, are in agreement with the determined CpG islands. FIG. 8 shows a fragment/length histogram for fragments with a share of CpG islands of at most 0.3. The vertical marking in the figures shows fragments having a length of 1,000 bp. As FIG. 8 makes clear, the fragments produced by the method according to the invention (method I) with a share of CpG islands of at most 0.3 are mainly fragments having a length of more than 1,000 bp.

As can be seen from Table 2, the complexity is reduced to 3.8% ($1.0 \times 10^8 / 2.6 \times 10^9$) of all base pairs of the complete genome. The fragments obtained thereby can then be used in a PCR amplification in Example 9 and further be analyzed as described there. According thereto, FIG. 7 makes clear that primarily only fragments are amplified, that have a share of CpG islands of more than 0.3. FIG. 8 shows, however, that the main part of the genome, DNA fragments having a share of at most 0.3, is separated.

TABLE 2

| | Fragments $\leq$ 1,000 bps and $\geq$ 100 bps | Fragments >1,000 bps and <100 bps |
|---|---|---|
| Share of CpG islands > 0.3 | $5.5 \times 10^7$ | $1.4 \times 10^8$ |
| Share of CpG islands $\leq$ 0.3 | $4.8 \times 10^7$ | $2.5 \times 10^9$ |
| Total DNA | $1.0 \times 10^8$ | $2.6 \times 10^9$ |

Example 19

Preparation of Two Solutions with Fragments of the Respective DNA Samples of Example 1 Without Methylation-Sensitive Restriction Enzymes Suitable to Analyse Copy-Numbers Section 1: 2 µg each of the genomic DNA of the preparations of Example 1 are first fragmented with 5 units each of the non-methylation-specific restriction enzymes MseI, Bfa1 and Csp6 (available from: New England Biolabs and MBI Fermentas) for 16 hours at 37° C. according to manufacturer's instructions. Then, these restriction enzymes are inactivated for 20 minutes at 65° C.

Section 2: Thereafter the QiaQuick PCR product purification column kit (Qiagen, Hilden, Germany) is used for purification. According to manufacturer's information, fragments shorter than 40 bases are very efficiently removed. It is not excluded, however, that some larger fragments up to a size of approx. 100 bp are also removed thereby. Then, according to the procedure Huang et al (*Hum Mol Genet,* 8(3):459-470, 1999), a ligation of adapters (or linkers) is carried out. For this purpose, different modifications of the original protocol are possible, which are described in the following. For the ligation, the fragmented DNA is mixed with 500 pmol adapter, 400 units T4 DNA Ligase (New England Biolabs), the volume ligase, as recommended by the manufacturer, of 10× buffer and ATP, and incubated for 16 hours at 16° C. The adapters are before prepared by that an equimolar mixture of the oligonucleotides H24 (5'-AGG CAA CTG TGC TAT CCG AGG GAT-3') and H12 (5'-TAA TCC CTC GGA-3') is first denaturated for 5 min at 95° C. and step by step cooled down to 25° C. The ligated DNA is finally purified by means of the QuiaQuick PCR product purification kit (Qiagen, Hilden, Germany).

Approx. 10-100 ng are used in a PCR reaction, which simultaneously serves for the amplification of a representation of uncut DNA fragments in the order of 50-1,000 bp. The PCR reaction batch contains 350 µM dNTPs, 2.5 µM marked primer (H24), 5 units DeepVent (exo-) DNA polymerase, 10 µl 10× buffer and 5% DMSO in a volume of 100 µl. The amplified DNA is finally purified by means of the QuiaQuick PCR product purification kit (Qiagen, Hilden, Germany).

10-12 PCR reactions are carried out with each sample, in order to obtain a total amount of 20 µg PCR product after the purification. The purified PCR products were fragmented and labeled according to the specification in the "Gene Chip Mapping Assay Manual" of Affymetrix Inc., in particular chapter 4 (page 38-42).

Thus samples of diseased and of adjacent healthy tissue are obtained, which are suitable for hybridization with the oligonucleotide microarray of Example 2 or the DNA microarray of Example 8.

Example 20

Hybridization of the Samples on the DNA Microarray for Analysing the Copy Number The two solutions obtained in example 19 are each hybridized with a DNA microarray according to Example 2. Hybridization and detection take place according to the specification in the "Gene Chip Mapping Assay Manual" of Affymetrix Inc., in particular chapter 4 (page 44-45), and chapter 6 "Washing, Staining & Scanning" (page 75-92).

Two hybridization patterns are obtained, and from a comparison of the two patterns, differences of copy numbers between diseased and healthy tissue can be recognized. With regard to the differences, the respective oligonucleotide set of the DNA microarray is identified and assigned, if applicable, to one or several proteins, peptides or enzymes. Normally, these proteins, peptides or enzymes are then differentially expressed at the respective patient. For the identification of a characteristic copy number change or for the detection of a marker (response or diagnosis marker), it is however not necessary to build up such a correlation.

If the differential copy numberrs and the differential expression affected thereby is confirmed for other patients also having the same disease, and if applicable corresponding cell lines, then the respective expression product is a suitable target for searching substances inhibiting or inducing the expression product (depending on whether the differential expression "diseased"/"healthy" is greater or smaller than 1).

Example 21

Signal Intensity Values for Three Microarray-Chips Each with 10 Immobilized Nucleic Acids After hybridization of DNA on the microarray on respective correlated immobilized nucleic acids under defined stringent conditions, the spatially resolved detection of such nucleic acids is performed by scanning for fluorescence radiation emitted by the fluorescence dye which is the label of the hybridized DNA. This spatially resolved detection leads to a signal intensity value for each immobilized nucleic acid. An example for such signal intensity values for three microarray-chips each with 10 immobilized nucleic acids is given in Table 3.

TABLE 3

Signal intensity values for three microarray-chips each with 10 immobilized nucleic acids.

| Category of nucleic acid | Number of immobilized nucleic acid | chip 1 | chip 2 | chip 3 |
|---|---|---|---|---|
| Set 1 | 1 | 3 | 4 | 17 |
| Set 1 | 2 | 4 | 15 | 18 |
| Set 1 | 3 | 10 | 5 | 16 |
| Set 2 | 4 | 14 | 6 | 3 |
| Set 2 | 5 | 2 | 9 | 11 |
| Set 2 | 6 | 17 | 17 | 19 |
| Set 2 | 7 | 9 | 3 | 1 |

TABLE 3-continued

Signal intensity values for three microarray-chips each with 10 immobilized nucleic acids.

| Category of nucleic acid | Number of immobilized nucleic acid | chip 1 | chip 2 | chip 3 |
|---|---|---|---|---|
| control | 8 | 16 | 20 | 12 |
| control | 9 | 11 | 18 | 6 |
| control | 10 | 20 | 7 | 20 |

Example 22

Applying the "Log-Transformation" on the Signal Intensity Values of Example 21

The signal intensity values of example 21 were subjected to a "Log-Transformation" according to the following formula:

$$\log 2(\text{signal intensity value})$$

The resulting value is then rounded according to the needed accuracy. For simplicity reasons the resulting value is listed in Table 4 with only two decimal digits.

TABLE 4

Values resulting after application of the Log-Transformation to the base 2 for the signal intensity values of Example 21.

| Category of nucleic acid | Number of immobilized nucleic acid | chip 1 | chip 2 | chip 3 |
|---|---|---|---|---|
| Set 1 | 1 | 1.58 | 2.00 | 4.09 |
| Set 1 | 2 | 2.00 | 3.91 | 4.17 |
| Set 1 | 3 | 3.32 | 2.32 | 4.00 |
| Set 2 | 4 | 3.81 | 2.58 | 1.58 |
| Set 2 | 5 | 1.00 | 3.17 | 3.46 |
| Set 2 | 6 | 4.09 | 4.09 | 4.25 |
| Set 2 | 7 | 3.17 | 1.58 | 0.00 |
| control | 8 | 4.00 | 4.32 | 3.58 |
| control | 9 | 3.46 | 4.17 | 2.58 |
| control | 10 | 4.32 | 2.81 | 4.32 |

Example 23

Applying the "Quantile Normalization" on the "log-transformed" Signal Intensity Values of Example 22

The "log-transformed signal intensity values of Example 22 are subjected to a "Quantile Normalization". The result of this operation leads to a equal signal intensity distribution over every considered microarray-chip. The "Quantile Normalization" is done according to the following algorithm:

a) Order the values according to their size for every microarray-chip. Table 4 is thereby transformed into Table 5. Table 5 shows the result of the first step of the "Quantile Normalization", the ordering of values according to their size.

| chip 1 | chip 2 | chip 3 |
|--------|--------|--------|
| 1.00 | 1.58 | 0.00 |
| 1.58 | 2.00 | 1.58 |
| 2.00 | 2.32 | 2.58 |
| 3.17 | 2.58 | 3.46 |
| 3.32 | 2.81 | 3.58 |
| 3.46 | 3.17 | 4.00 |
| 3.81 | 3.91 | 4.09 |
| 4.00 | 4.09 | 4.17 |
| 4.09 | 4.17 | 4.25 |
| 4.32 | 4.32 | 4.32 | b). The arithmetic mean value is calculated for each immobilized nucleic acid over the different microarray-chips. The results are illustrated by Table 6.

Table 6 shows the results of the second step of the "Quantile Normalization", the calculation of the arithmetic mean values.

| chip 1 | chip 2 | chip 3 | arithmetic means |
|--------|--------|--------|------------------|
| 1.00 | 1.58 | 0.00 | 0.86 |
| 1.58 | 2.00 | 1.58 | 1.72 |
| 2.00 | 2.32 | 2.58 | 2.30 |
| 3.17 | 2.58 | 3.46 | 3.07 |
| 3.32 | 2.81 | 3.58 | 3.24 |
| 3.46 | 3.17 | 4.00 | 3.54 |
| 3.81 | 3.91 | 4.09 | 3.93 |
| 4.00 | 4.09 | 4.17 | 4.09 |
| 4.09 | 4.17 | 4.25 | 4.17 |
| 4.32 | 4.32 | 4.32 | 0.86 | c) Replacing the signal intensity values by their corresponding arithmetic mean value. The results are illustrated by Table 7.

Table 7 shows the results of the third step of the "Quantile Normalization", the replacing of the signal intensity values by the corresponding arithmetic mean values.

| Chip 1 | Chip 2 | Chip 3 |
|--------|--------|--------|
| 0.86 | 0.86 | 0.86 |
| 1.72 | 1.72 | 1.72 |
| 2.30 | 2.30 | 2.30 |
| 3.07 | 3.07 | 3.07 |
| 3.24 | 3.24 | 3.24 |
| 3.54 | 3.54 | 3.54 |
| 3.93 | 3.93 | 3.93 |
| 4.09 | 4.09 | 4.09 |
| 4.17 | 4.17 | 4.17 |
| 4.32 | 4.32 | 4.32 | d) Reordering of the values according to their original order on the microarray-chips. The results are illustrated by Table 8.

Table 8 shows the results of the fourth step of the "Quantile Normalization", the reordering of the values according to their original order on the microarray-chips.

| Category of nucleic acid | Number of immobilized nucleic acid | chip 1 | chip 2 | chip 3 |
|---|---|---|---|---|
| Set 1 | 1 | 1.72 | 1.72 | 3.93 |
| Set 1 | 2 | 2.30 | 3.93 | 4.09 |
| Set 1 | 3 | 3.24 | 2.30 | 3.54 |
| Set 2 | 4 | 3.93 | 3.07 | 1.72 |
| Set 2 | 5 | 0.86 | 3.54 | 3.07 |
| Set 2 | 6 | 4.17 | 4.09 | 4.17 |
| Set 2 | 7 | 3.07 | 0.86 | 0.86 |
| control | 8 | 4.09 | 4.32 | 3.24 |
| control | 9 | 3.54 | 4.17 | 2.30 |
| control | 10 | 4.32 | 3.24 | 4.32 |

Example 24

Applying the "Baseline Shift" on the Signal Intensity Values of Example 23 after the "Quantile Normalization"

The values after the "Quantile Normalization" are subjected to the "Baseline Shift". This procedure is carried out by first calculating the arithmetic mean value of the controls for every chip. Subsequently, this mean value is subtracted from each value (see Table 8) of the corresponding microarray-chip.

The results are illustrated by Table 9.

| Category of nucleic acid | Number of immobilized nucleic acid | chip 1 | chip 2 | chip 3 |
|---|---|---|---|---|
| Set 1 | 1 | −2.26 | −2.19 | 0.65 |
| Set 1 | 2 | 1.68 | 0.02 | 0.80 |
| Set 1 | 3 | −0.75 | −1.61 | 0.26 |
| Set 2 | 4 | −0.05 | −0.84 | −1.56 |
| Set 2 | 5 | −3.12 | −0.37 | −0.22 |
| Set 2 | 6 | 0.18 | 0.18 | 0.88 |
| Set 2 | 7 | −0.91 | −3.05 | −2.43 |
| control | 8 | 0.10 | 0.41 | −0.05 |
| control | 9 | −0.44 | 0.26 | −0.99 |
| control | 10 | 0.34 | −0.67 | 1.03 |

Example 25

Generation of a Representative Value for the Signal Intensity Values of a Set of Immobilized Nucleic Acids The signal intensity values as they are shown by Table 9 are subjected to an operation which leads to one representative value for the signal intensity values of a set of immobilized nucleic acids. This is done by selecting the median value from the signal intensity values of immobilized nucleic acids of the same set for each microarray-chip. This is illustrated by Table 10.

Table 10 shows the result of the generation of a representative value for the signal intensity vales of a set of immobilized nucleic acids.

| Category of nucleic acid | chip 1 | chip 2 | chip 3 |
|---|---|---|---|
| Set 1 | −1.68 | −1.61 | 0.65 |
| Set 2 | −0.48 | −0.60 | −0.89 |
| control | 0.10 | 0.26 | −0.05 |

These preprocessed signal intensity values are then subjected to further analysis which leads to a deduction of the methylation status of the hybridized DNA.

The invention claimed is:

1. A method for determining a DNA methylation pattern, comprising:
   a) obtaining a solution comprising a sized-biased amplified mixture of genomic DNA restriction fragments, wherein the generation of said mixture comprises an enrichment step using proteins that bind methylation-specifically to the DNA, and wherein the composition of the restriction fragment mixture depends on the methylation pattern of the genomic DNA;
   b) coupling the amplified fragments with a detectable label to provide a labeled fragment amplificate;
   c) contacting the labeled fragment amplificate with at least one DNA microarray having a plurality of different nucleic acids assigned to different respective array locations, wherein hybridization of amplificate fragments with the corresponding assigned nucleic acids takes place under definable stringency, and wherein the assigned nucleic acids are specific for genomic fragments obtainable by cutting with the restriction enzymes used in a); and
   d) detecting the label of the hybridized fragment amplificate using a suitable detection method, wherein determination of a hybridization pattern of the assigned array locations is afforded to further afford determination of the genomic DNA methylation pattern.

2. A method for determining a DNA methylation pattern, comprising:
   a) obtaining a solution comprising a sized-biased amplified mixture of genomic DNA restriction fragments, wherein the generation of said mixture comprises the use of a triplex-forming molecule, which when brought in contact with the DNA, distinguishes between methylated and non-methylated DNA, and wherein the composition of the restriction fragment mixture depends on the methylation pattern of the genomic DNA;
   b) coupling the amplified fragments with a detectable label to provide a labeled fragment amplificate;
   c) contacting the labeled fragment amplificate with at least one DNA microarray having a plurality of different nucleic acids assigned to different respective array locations, wherein hybridization of amplificate fragments with the corresponding assigned nucleic acids takes place under definable stringency, and wherein the assigned nucleic acids are specific for genomic fragments obtainable by cutting with the restriction enzymes used in a); and
   d) detecting the label of the hybridized fragment amplificate using a suitable detection method, wherein determination of a hybridization pattern of the assigned array locations is afforded to further afford determination of the genomic DNA methylation pattern.

3. A method for determining a DNA methylation pattern, comprising:
   a) obtaining a solution comprising a sized-biased amplified mixture of genomic DNA restriction fragments, wherein the generation of said mixture comprises the use of the MS AP-PCR method, and wherein the composition of the restriction fragment mixture depends on the methylation pattern of the genomic DNA;
   b) coupling the amplified fragments with a detectable label to provide a labeled fragment amplificate;
   c) contacting the labeled fragment amplificate with at least one DNA microarray having a plurality of different nucleic acids assigned to different respective array locations, wherein hybridization of amplificate fragments with the corresponding assigned nucleic acids takes place under definable stringency, and wherein the assigned nucleic acids are specific for genomic fragments obtainable by cutting with the restriction enzymes used in a); and
   d) detecting the label of the hybridized fragment amplificate using a suitable detection method, wherein determination of a hybridization pattern of the assigned array locations is afforded to further afford determination of the genomic DNA methylation pattern.

4. A method for determining a DNA methylation pattern, comprising:
   a) generating, by enrichment of methylated DNA, a sized-biased amplified mixture of genomic DNA restriction fragments obtained from a test sample, wherein the composition of said mixture depends on the methylation pattern of the genomic DNA of the test sample;

b) generating, by enrichment of methylated DNA, a sized-biased amplified mixture of genomic DNA restriction fragments obtained from a completely methylated aliquot of a reference sample, wherein the composition of said mixture depends on the methylation pattern of the genomic DNA of the completely methylated aliquot;

c) generating, by enrichment of methylated DNA, a sized-biased amplified mixture of genomic DNA restriction fragments obtained from a completely unmethylated aliquot of said reference sample, wherein the composition of said mixture depends on the methylation pattern of the genomic DNA of the completely unmethylated aliquot;

d) labeling the fragments of each of the mixtures of step (a)-(c) to provide labeled fragment amplificates;

e) contacting the labeled fragment amplificates of step (d) with at least one DNA microarray having a plurality of different nucleic acids assigned to different respective array locations, wherein hybridization of amplificates with the corresponding assigned nucleic acids takes place under definable stringency, and wherein the assigned nucleic acids are specific for genomic DNA restriction fragments obtainable by step (a), (b) and (c);

f) detecting the label of fragment amplificates hybridized to assigned nucleic acids using a suitable detection method;

g) obtaining at least one value, each value for an assigned nucleic acid, said value being represented by $$\frac{I^M_{test} - I^M_{0\%}}{I^M_{100\%} - I^M_{0\%}}$$

wherein $I^M_{test}$ represents the signal intensity obtained for a fragment amplificate of the test sample, $I^M_{0\%}$ represents the signal intensity obtained for a respective fragment amplificate of the 0% methylated reference sample, and $I^M_{100\%}$ represents the signal intensity obtained for a respective fragment amplificate of the 100% methylated reference; and (h) deducing for each of the values obtained in step (g), if the value for an assigned nucleic acid is i) "0," that all analyzed cytosines in the corresponding genomic DNA region of the test sample are unmethylated, or deducing, if the value for an assigned nucleic acid is ii) in the range between "0" and "1," that the value multiplied by 100 represents the percentage of methylated cytosines in the corresponding genomic DNA region of the test sample, or deducing, if the value for an assigned nucleic acid is iii) "1," that all analyzed cytosines in the corresponding genomic DNA region of the test sample are methylated, and wherein a DNA methylation pattern is determined.

5. A method for determining a DNA methylation pattern, comprising:

a) generating, by enrichment of unmethylated DNA, a sized-biased amplified mixture of genomic DNA restriction fragments from a test sample, wherein the composition of said mixture depends on the methylation pattern of the genomic DNA of the test sample;

b) generating, by enrichment of unmethylated DNA, a sized-biased amplified mixture of genomic DNA restriction fragments from a completely methylated aliquot of a reference sample, wherein the composition of said mixture depends on the methylation pattern of the genomic DNA of the completely methylated aliquot;

c) generating, by enrichment of unmethylated DNA, a sized-biased amplified mixture of genomic DNA restriction fragments from a completely unmethylated aliquot of said reference sample, wherein the composition of said mixture depends on the methylation pattern of the genomic DNA of the completely unmethylated aliquot;

d) labeling the fragments of each of the mixtures of step (a)-(c) to provide labeled fragment amplificates;

e) contacting the labeled fragment amplificates of step (d) with at least one DNA microarray having a plurality of different nucleic acids assigned to different respective array locations, wherein hybridization of amplificates with the corresponding assigned nucleic acids takes place under definable stringency, and wherein the assigned nucleic acids are specific for genomic DNA restriction fragments obtainable by step (a), (b) and (c);

f) detecting the label of fragment amplificates hybridized to assigned nucleic acids using a suitable detection method;

g) obtaining at least one value, each value for an assigned nucleic acid, said value being represented by $$1 - \frac{I^{UM}_{test} - I^{UM}_{100\%}}{I^{UM}_{0\%} - I^{UM}_{100\%}}$$

wherein $I^{UM}_{test}$ represents the signal intensity obtained for the test sample by means of unmethylated DNA enrichment, $I^{UM}_{100\%}$ represents the signal intensity obtained for the 100% methylated reference sample by means of unmethylated DNA enrichment, and $I^{UM}_{0\%}$ represents the signal intensity obtained for the 0% methylated reference sample by means of unmethylated DNA enrichment; and h) deducing for each of the values obtained in step (g), if the value for an assigned nucleic acid is i) "0," that all analyzed cytosines in the corresponding genomic DNA region of the test sample are unmethylated, or deducing, if the value for an assigned nucleic acid is ii) in the range between "0" and "1," that the value multiplied by 100 represents the percentage of methylated cytosines in the corresponding genomic DNA region of the test sample, or deducing, if the value for an assigned nucleic acid is iii) "1," that all analyzed cytosines in the corresponding genomic DNA region of the test sample are methylated, and wherein a DNA methylation pattern is determined.

6. A method for determining at least one of the percentage of methylation and the relative copy-number of positions of a test sample DNA, comprising:

a) generating, by enrichment of methylated and/or unmethylated DNA, a sized-biased amplified mixture of genomic DNA restriction fragments from DNA derived from a test sample, wherein the composition of said mixture depends on the methylation pattern of the genomic DNA of the test sample;

b) generating, by enrichment of at least one of methylated and unmethylated DNA, a sized-biased amplified mixture of genomic DNA restriction fragments from DNA derived from a reference sample, wherein the composition of said mixture depends on the methylation pattern of the genomic DNA of the reference sample;

c) labeling the fragments of the mixtures of step (a) and (b) identically or differentially with one or more detectable labels;

d) contacting the labeled fragment amplificates of step (c) with at least one DNA microarray having a plurality of different oligonucleotides assigned to different respective array locations, wherein hybridization of amplificates with the corresponding assigned oligonucleotides takes place under definable stringency, and wherein the assigned oligonucleotides are specific for genomic DNA restriction fragments obtainable by step (a) and (b), wherein labeled amplificates are hybridized onto assigned oligonucleotides of the DNA microarray;

e) detecting the spatially resolved signal intensities of oligonucleotide array locations; and f) comparing the detected signal intensities derived for the amplificates of the test sample with those derived for the amplificates of the reference sample, wherein the percentage of methylation and/or the relative copy-number of positions of the test sample DNA is deduced.

7. A method for determining a DNA methylation pattern, comprising:
   a) obtaining a solution comprising a sized-biased amplified mixture of genomic DNA restriction fragments, wherein the composition of the restriction fragment mixture depends on the methylation pattern of the genomic DNA;
   b) coupling the amplified fragments with a detectable label to provide a labeled fragment amplificate;
   c) contacting the labeled fragment amplificate with at least one DNA microarray having a plurality of different nucleic acids assigned to different respective array locations, wherein hybridization of amplificate fragments with the corresponding assigned nucleic acids takes place under definable stringency, and wherein the assigned nucleic acids are specific for genomic fragments obtainable by cutting with the restriction enzymes used in a);
   d) detecting the signal intensities derived from hybridized labeled amplificate fragments using a suitable detection method; and
   e) preprocessing of the detected signal intensities, wherein the preprocessing comprises Log-Transformation, and further comprises at least one selected from the group consisting of: Quantile Normalization; Baseline Shift; and
   f) generating a representative value for the signal intensity values of a set of nucleic acids immobilized on the DNA microarray, wherein determining a DNA methylation pattern is provided.

8. A method for determining a DNA methylation pattern, comprising:
   a) obtaining a solution comprising a sized-biased amplified mixture of genomic DNA restriction fragments, wherein the composition of the restriction fragment mixture depends on the methylation pattern of the genomic DNA;
   b) coupling the amplified fragments with a detectable label to provide a labeled fragment amplificate;
   c) contacting the labeled fragment amplificate with at least one DNA microarray having a plurality of different nucleic acids assigned to different respective array locations, wherein hybridization of amplificate fragments with the corresponding assigned nucleic acids takes place under definable stringency, wherein the assigned nucleic acids are specific for genomic fragments obtainable by cutting with the restriction enzymes used in a), and wherein the array exclusively comprises oligonucleotide sequences which hybridize in constant to each other defined distances on the corresponding analyzed complementary DNA, providing a tiling array; and
   d) detecting the label of the hybridized fragment amplificate using a suitable detection method, wherein determination of a hybridization pattern of the assigned array locations is afforded to further afford determination of the genomic DNA methylation pattern.

9. The method of any one of claims 1 through 8, wherein defining the sequences of the assigned oligonucleotides comprises:
   a) testing a genome for first partial sequences that are bordered by restriction sites of non-methylation-specific restriction enzymes, and that have a length of about 100 to about 1,200 base pairs, and thereby selecting said first partial sequences;
   b) excluding from the selected first partial sequences, sequences that comprise more than about 50% repeat sequences, or more than about 20% repeat sequences, thereby selecting second partial sequences; and
   c) selecting, arbitrarily or otherwise, oligonucleotide sequences from the second partial sequences, the corresponding oligonucleotides to be immobilized on the microarray.

10. The method of any one of claims 1 through 8, wherein at least one methylation-specific restriction enzyme is used for generating a size-biased amplified mixture of genomic DNA restriction fragments, and wherein defining the sequences of the assigned oligonucleotides comprises:
   a) testing a genome for first partial sequences that are bordered by restriction sites of non-methylation-specific restriction enzymes, and that have a length of about 100 to about 1,200 base pairs, and thereby selecting said first partial sequences;
   b) excluding from the selected first partial sequences, sequences that comprise more than about 50% repeat sequences, or more than about 20% repeat sequences, thereby selecting second partial sequences;
   c) testing the selected second partial sequences for the presence of at least one restriction site of at least one methylation-specific restriction enzyme, and selecting third partial sequences having such sites; and
   d) selecting, arbitrarily or otherwise, oligonucleotide sequences from the third partial sequences, the corresponding oligonucleotides to be immobilized on the microarray.

11. The method of any one of claims 1 through 8, wherein defining the sequences of the assigned oligonucleotides comprises:
   a) testing a genome for first partial sequences that are bordered by restriction sites of methylation-specific restriction enzymes, and that have a length of about 100 to about 1,200 base pairs, and thereby selecting said first partial sequences;
   b) excluding from the selected first partial sequences, sequences that comprise more than about 50% repeat sequences, or more than about 20% repeat sequences, thereby selecting second partial sequences sequences; and
   c) selecting, arbitrarily or otherwise, oligonucleotide sequences from the second partial sequences, the corresponding oligonucleotides to be immobilized on the microarray.

12. The method of any one of claims 1 through 8, wherein defining the sequences of the assigned oligonucleotides comprises:
   a) testing a genome for first partial sequences that are bordered by restriction sites of at least one first restriction enzyme used for fragmentation, and that have a length of about 100 to about 1,200 base pairs, and thereby selecting said first partial sequences;
   b) excluding from the selected first partial sequences, sequences that comprise more than about 50% repeat sequences, or more than about 20% repeat sequences, thereby selecting second partial sequences;
   c) testing the selected second partial sequences for the presence of restriction sites of at least one second restriction enzyme used for fragmentation and thereby selecting third partial sequences that comprise such restriction sites; and
   d) selecting, arbitrarily or otherwise, oligonucleotide sequences from the third partial sequences, the corresponding oligonucleotides to be immobilized on the microarray.

13. The method of any one of claims 1 through 8, comprising:
   a) digesting the DNA with at least one non-methylation-specific restriction enzyme, wherein the DNA is cut at corresponding restriction sites;
   b) selectively depleting DNA fragments less than about 50 bases in length from the digested DNA);
   c) ligating adaptors to the depleted DNA;
   d) digesting the depleted DNA with at least one methylation-specific restriction enzyme, wherein the depleted DNA is cut at corresponding unmethylated restriction sites to provide a further digested DNA; and
   e) amplifying the further digested DNA, using primer mediated-amplification of adapter-ligated fragments to provide a size biased fragment amplificate;
   or comprising:
   a) digesting the DNA with at least one non-methylation-specific restriction enzyme, wherein the DNA is cut at corresponding restriction sites;
   b) selectively depleting DNA fragments less than about 50 bases in length from the digested DNA);
   c) ligating adaptors to the depleted DNA; and
   d) amplifying the adapter-ligated DNA, using primer mediated-amplification of adaptor-ligated fragments to provide a size biased fragment amplificate.

14. The method of claim 1, wherein the enrichment comprises use of
   a) at least one of MeCP2, MBD1, MBD2, MBD4, Kaiso, or suitable domains of these proteins;
   b) MBD-column chromatography, comprising a combination of enrichment of non-methylated DNA by binding to a column specific for non-methylated DNA, with enrichment of methylated DNA by binding to a column specific for methylated DNA; and at least one of
   c) antibodies specific for at least one of MeCP2, MBD1, MBD2, MBD4, Kaiso or one or more domains thereof; and
   d) methylation-specific antibodies.

15. The method of claim 6, comprising,
   generating two corresponding types of DNA samples from each of a test sample and a reference sample, wherein generating the first type of sample comprises a complexity reduction of genomic DNA that is independent of the genomic DNA methylation pattern, wherein generating the second type of sample comprises a first methylation-unspecific restriction enzyme digestion and a second methylation-specific restriction enzyme digestion;
   deducing copy-number variations by comparison of detected signal intensities of the first type of DNA fragment samples of the test sample with the detected signal intensities of the first type of DNA fragment samples of the reference sample; and
   deducing methylation changes by comparison of detected signal intensities of the second type of DNA fragment samples of the test sample with the detected signal intensities of the second type of DNA fragment samples of the reference sample.

16. The method of claim 6, comprising:
   generating two corresponding types of DNA fragment samples from each of a test sample and a reference sample, wherein generating the first type of sample comprises a first methylation-unspecific restriction enzyme digestion and a second methylation-specific restriction enzyme digestion, and wherein generating the second type of sample comprises a methylation-specific restriction enzyme digestion;
   deducing an alteration in DNA methylation by comparison of hybridization signal intensities of the first type of DNA fragments of the test sample with those of a reference sample, or by comparison of hybridization signal intensities of the second type of DNA fragments of the test sample with those of the reference sample, or both; and
   deducing a copy-number variation by comparison of hybridization signal intensity of the first type of DNA fragments of a test sample with those derived from the reference sample, and by comparison of hybridization signal intensity of the second type of DNA fragments of the test samples with those of the reference sample.

17. The method of claim 6, comprising:
   generating, by enrichment of methylated DNA, DNA fragments from a test sample, from a completely methylated aliquot of a reference sample, and from a completely unmethylated aliquot of said reference sample; and
   obtaining a value represented by the quotient of the difference of the hybridization signal intensity of the test sample and the hybridization signal intensity of the completely unmethylated reference sample to the signal difference of the completely methylated reference sample and the completely unmethylated reference sample; wherein an increase of the copy-number of the analyzed genomic region in the test sample is deduced where quotient values are larger than 1.

18. The method of claim 6, comprising:
   generating, by enrichment of unmethylated DNA, DNA fragments from a test sample, from a completely methylated aliquot of a reference sample, and from a completely unmethylated aliquot of said reference sample; and
   obtaining a value represented by the quotient of the difference of the signal intensity of the test sample and the signal intensity of the completely methylated reference sample to the signal difference of the completely unmethylated reference sample and the completely methylated reference sample, wherein an increase of the copy-number of the analyzed genomic region in the test sample is deduced where quotient values are larger than 1.

19. The method of claim 6, wherein generation of the sized-biased amplified mixture comprises an enrichment step using proteins that bind methylation-specifically to the DNA.

20. The method of claim 6, wherein generation of the sized-biased amplified mixture comprises the use of a triplex-forming molecule, which when brought in contact with the DNA, distinguishes between methylated and non-methylated DNA.

21. The method of claim 6, wherein generation of the sized-biased amplified mixture comprises use of the MS AP-PCR method.

* * * * *